United States Patent
Barberis et al.

(10) Patent No.: US 7,595,320 B2
(45) Date of Patent: Sep. 29, 2009

(54) HYDRAZINOCARBONYL-THIENO [2,3-C]PYRAZOLES, PROCESS FOR PREPARING THEM, COMPOSITIONS CONTAINING THEM AND USE THEREOF

(75) Inventors: Claude Barberis, Hillsborough, NJ (US); Jean-Christophe Carry, Saint Maur des Fosses (FR); Gilles Doerflinger, Les Ulis (FR); Dominique Barbalat-Damour, Orly (FR); Francois Clerc, Antony (FR); Herve Minoux, Thiais (FR)

(73) Assignee: Aventis Pharma S.A., Antony (FR)

( * ) Notice: Subject to any disclaimer, the term of this patent is extended or adjusted under 35 U.S.C. 154(b) by 53 days.

(21) Appl. No.: 11/846,669

(22) Filed: Aug. 29, 2007

(65) Prior Publication Data

US 2008/0146542 A1 Jun. 19, 2008

Related U.S. Application Data

(63) Continuation of application No. PCT/FR2006/000480, filed on Mar. 3, 2006.

(30) Foreign Application Priority Data

Mar. 4, 2005 (FR) ................... 05 02199

(51) Int. Cl.
- *A61K 31/496* (2006.01)
- *A61K 31/4162* (2006.01)
- *C07D 231/54* (2006.01)
- *C07D 409/14* (2006.01)

(52) U.S. Cl. .................. 514/254.01; 544/358; 544/359; 544/366; 544/371; 548/356.1; 548/358.1; 548/360.1; 548/360.5; 514/252.12; 514/252.13; 514/406

(58) Field of Classification Search ................. 544/358, 544/359, 366, 371; 548/356.1, 358.1, 360.1, 548/360.5; 514/252.12, 252.13, 254.01, 514/403, 406
See application file for complete search history.

(56) References Cited

U.S. PATENT DOCUMENTS

| | | |
|---|---|---|
| 2005/0026984 A1 | 2/2005 | Bigot et al. |
| 2005/0208582 A1 | 9/2005 | Ohi et al. |
| 2005/0261339 A1 | 11/2005 | Ohi et al. |

FOREIGN PATENT DOCUMENTS

| | | |
|---|---|---|
| WO | WO 03/101968 A1 | 12/2003 |
| WO | WO 2004/007504 A1 | 1/2004 |
| WO | WO 2004/013146 A1 | 2/2004 |

OTHER PUBLICATIONS

U.S. Appl. No. 11/752,612, filed May 23, 2007, Carry et al.

*Primary Examiner*—Golam M Shameem
(74) *Attorney, Agent, or Firm*—Kelly L. Bender

(57) ABSTRACT

The present invention concerns hydrazinocarbonyl-thieno[2, 3-*c*]pyrazoles of formula (I):

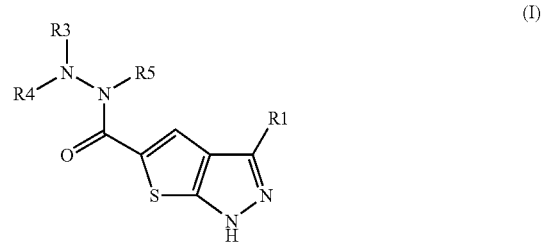

wherein R1, R3, R4, are R5 are as defined in the disclosure; their preparation method, compositions containing the same and their use for the treatment of pathological conditions, in particular as anticancer agents.

15 Claims, No Drawings

HYDRAZINOCARBONYL-THIENO [2,3-C]PYRAZOLES, PROCESS FOR PREPARING THEM, COMPOSITIONS CONTAINING THEM AND USE THEREOF

The present invention relates especially to substituted hydrazinocarbonyl-thieno[2,3-c]pyrazoles, to a process for preparing them, to compositions containing them and to their use as medicaments.

More particularly, and according to a first aspect, the invention relates to substituted hydrazinocarbonyl-thieno[2,3-c] pyrazoles that are useful as anticancer agents.

1H-Thieno[2,3-c]pyrazoles are known from WO 04/013 146 and WO 03/101 968. These products are presented as inhibitors of numerous protein kinases. However, the administration of such products to patients may induce considerable side effects, on account of their broad spectrum of action. Thus, the production of specific inhibitors of a selection of proteins, especially of kinases, is desired.

Against all expectation, it has been found that it is possible to obtain inhibitors of the kinase Aurora2 (Aurora A) and of certain other kinases that are useful in oncology, with substituted hydrazinocarbonyl-1H-thieno[2,3-c]pyrazoles.

These products correspond to the general formula (I) below:

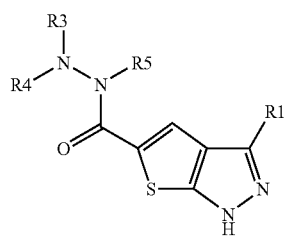

in which:
(i) R1 is independently selected from the group consisting of —NHCO(R2), —NHCONH(R2) and —NHCOO(R2), in which R2 is independently selected from the group consisting of —H, —($C_1$-$C_{24}$)alkyl, —($C_3$-$C_9$)cycloalkyl, —($C_3$—($C_3$-$C_9$)cycloalkylene, heterocycloalkyl, heterocycloalkylene, aryl, heteroaryl, —($C_1$-$C_6$)alkyl-aryl, —($C_1$-$C_6$)alkyl-heteroaryl, -aryl-($C_1$-$C_6$)alkyl and -heteroaryl-($C_1$-$C_6$)alkyl, optionally substituted;
(ii) each of the R3, R4 and R5 is independently selected from the group consisting of H, —($C_1$-$C_6$)alkyl, —($C_1$-$C_6$) alkyl-aryl, —($C_1$-$C_6$)alkyl-heteroaryl, -aryl and -heteroaryl, optionally substituted, or alternatively [(R3 and R4) or (R3 and R5)] are linked together to form a saturated or unsaturated, 2- to 10-membered monocyclic or bicyclic carbon heterocycle containing from 1 to 5 heteroatoms chosen from N, O and S, optionally substituted, or to form a group N=CH-aryl, said aryl being optionally substituted.

In the context of the invention, and unless otherwise mentioned in the text, the following definitions apply:
halogen: a fluorine, a chlorine, a bromine or an iodine.
alkyl: a linear or branched saturated aliphatic substituent containing from 1 to 12 carbon atoms. Examples that may be mentioned include methyl, ethyl, propyl, isopropyl, butyl, isobutyl, tert-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, etc. groups;
alkylene: an alkyl substituent as defined above, which is divalent. Examples that may be mentioned include methylene (—$CH_2$—) or dimethylene (—$CH_2$—$CH_2$—), ethylenyl, 1-methylethylenyl, prop-1-enyl, prop-2-enyl, Z-1-methylprop-1-enyl, E-1-methylprop-1-enyl, Z-1,2-dimethyl-prop-1-enyl, E-1,2-dimethyl-prop-1-enyl, but-1,3-dienyl, 1-methylidenyl-prop-2-enyl, Z-2-methylbut-1,3-dienyl, E-2-methylbut-1,3-dienyl, 2-methyl-1-methylidenylprop-2-enyl, undec-1-enyl and undec-10-enyl, etc. groups;
aryl: a monocyclic or polycyclic aromatic substituent containing from 6 to 14 carbon atoms. Examples that may be mentioned include phenyl, naphth-1-yl, naphth-2-yl, anthracen-9-yl, 1,2,3,4-tetrahydronaphth-5-yl, 1,2,3,4-tetrahydronaphth-6-yl, etc. groups;
cycloalkyl: an alkyl substituent as defined above, which contains from 3 to 12 carbon atoms and which is cyclic. Examples that may be mentioned include cyclopropyl, cyclobutyl, cyclopentyl, cyclopentenyl, cyclopentadienyl, cyclohexyl, cyclohexenyl, cycloheptyl; bicyclo [2.2.1]heptyl, cyclooctyl, bicyclo[2.2.2]octyl, adamantyl, perhydronapthyl, etc. substituents;
heteroatom: a nitrogen, oxygen or sulfur atom;
heteroaryl: a 5- to 12-membered monocyclic or polycyclic aromatic substituent comprising from 1 to 4 heteroatoms as defined above. Examples that may be mentioned include pyrrol-1-yl, pyrrol-2-yl, pyrrol-3-yl, furyl, thienyl, imidazolyl, pyrazolyl, oxazolyl, thiazolyl, isoxazolyl, isothiazolyl, 1,2,4-triazolyl, oxadiazolyl, thiadiazolyl, tetrazolyl, pyridyl, pyrimidyl, pyrazinyl, 1,3,5-triazinyl, indolyl, benzo[b]furyl, benzo[b]thienyl, indazolyl, benzimidazolyl, azaindolyl, quinolyl, isoquinolyl, carbazolyl, acridyl, etc.;
heterocyclyl: a saturated or partially unsaturated 5- to 13-membered cyclic hydrocarbon-based substituent comprising 1 to 4 heteroatoms as defined above. Preferably, the saturated or partially unsaturated cyclic hydrocarbon-based substituent will be monocyclic and will contain 4 or 5 carbon atoms and 1 to 3 heteroatoms. Examples that may be mentioned include piperidyl, azetidinyl, piperazinyl, morpholinyl, oxazepinyl, pyrrolidinyl, diazepinyl, etc. substituents;
alkoxy: a substituent of formula —O-alkyl in which the alkyl group is as defined above;
substituted: a substituent other than H, for example halogen, alkyl, aryl; heteroaryl, cycloalkyl, heterocyclyl, alkylene, alkynyl, OH, O-alkyl, O-alkylene, O-aryl, O-heteroaryl, SH, S-alkyl, S-aryl, $S(O_2)$H, $S(O_2)$-alkyl, $S(O_2)$-aryl, $SO_3$H, $SO_3$-alkyl, $SO_3$-aryl, CHO, C(O)-alkyl, C(O)-aryl, C(O)OH, C(O)O-alkyl, C(O)O-aryl, OC(O)-alkyl, OC(O)-aryl, $C(O)NH_2$, C(O)NH-aryl, C(O)NHR7, C(O)NR7R8, —($C_1$-$C_3$)alkyl-aryl, —($C_1$-$C_3$)alkyl-heteroaryl, —($C_1$-$C_3$)alkyl-heterocyclyl, —($C_1$-$C_3$)alkyl-cycloalkyl and NR7R8, in which the rings are optionally substituted with one or more substituents from the group halogen, ($C_1$-$C_3$)alkyl and alkoxy, and in which R7 and R8 are independently selected from the group consisting of H, alkyl, aryl, heteroaryl, cycloalkyl, heterocyclyl, alkyl-N[($C_1$-$C_6$) alkyl]$_2$, —C(O)-alkyl and —C(O)-aryl. Preferably, in the group R2, the term "substituted" denotes a substituent from among halogen, ($C_1$-$C_6$)alkyl, aryl, heteroaryl, cycloalkyl, heterocyclyl, alkylene, alkynyl, OH, O-alkyl, O-alkylene and NR7R8, in which the rings are optionally substituted with one or more substituents from the group halogen, $(C_1\text{-}C_3)$alkyl and alkoxy, and in which R7 and R8 are independently selected from the group consisting of hydrogen, $(C_0\text{-}C_3)$alkyl, phenyl, heteroaryl, cycloalkyl, heterocyclyl and $(C_1\text{-}C_3)$alkyl-N $[(C_0\text{-}C_3)$alkyl$]_2$. Preferably, when [(R3 and R4) or (R3 and R5)] are linked together to form a ring or a group N=CH-aryl, the term "substituted" denotes one or more substituents from the group halogen, —$(C_1\text{-}C_6)$alkyl and —(CO—$C_6$)alkyl-alkoxy;

$C_0$: a covalent bond or —H;

by convention for —$(C_1\text{-}C_6)$alkyl-aryl: attachment to the rest of the molecule takes place on the alkyl group. Conversely, for -Aryl-$(C_1\text{-}C_6)$-alkyl, attachment takes place on the aryl group.

the term JNK proteins means the proteins JNK1, 2 and 3.

Among the preferred values of R1, NHCO(R2) is chosen; in which R2 is preferably chosen from aryl, heteroaryl and -aryl-$(C_1\text{-}C_6)$alkyl, optionally substituted.

A subject of the invention is most particularly the products of formula (I) corresponding to formula (I'):

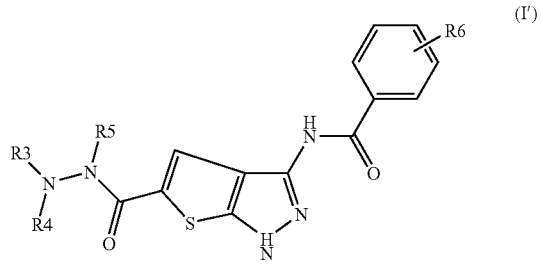

in which:
each of the groups R3, R4 and R5 is as defined above, and R6 is chosen from the group consisting of halogen, $(C_1\text{-}C_3)$alkyl-NR7R8, $(C_1\text{-}C_6)$alkoxy, $(C_0\text{-}C_3)$alkyl-heterocycle, $(C_0\text{-}C_3)$alkyl-aryl, $(C_0\text{-}C_3)$alkyl-heteroaryl and $(C_0\text{-}C_3)$alkyl-cycloalkyl, in which the rings are optionally substituted with one or more substituents $(C_1\text{-}C_3)$ alkyl, halogen or alkoxy, and in which R7 and R8 are independently selected from the group consisting of —H, $(C_0\text{-}C_3)$alkyl, aryl and $(C_1\text{-}C_3)$alkyl-N—$[(C_0\text{-}C_3)$ alkyl$]_2$.

More particularly, the group R6 is in position 3 or 4 on the phenyl to which it is attached.

More particularly, R6 according to the present invention is —$(C_0\text{-}C_3)$alkyl-heterocycle, said heterocycle itself being optionally substituted with one or more substituents $(C_1\text{-}C_3)$ alkyl, halogen or alkoxy.

More particularly, R3 is advantageously chosen from aryl, heteroaryl, —$(C_1\text{-}C_6)$alkyl-aryl and —$(C_1\text{-}C_6)$alkyl-heteroaryl, optionally substituted, preferably from phenyl, pyridyl, indolyl, benzimidazolyl, pyrazolyl and pyrrolyl, optionally substituted.

More particularly, R4 is advantageously chosen from H and alkyl, especially —$(C_1\text{-}C_6)$alkyl. Most particularly, R4 is H, methyl or ethyl.

More particularly, R5 is advantageously chosen from H and alkyl, especially —$(C_1\text{-}C_6)$alkyl.

More particularly, R3 and R4 form, with the nitrogen to which they are attached, a 5- or 6-membered heterocycle also containing, where appropriate, an N, O or S atom, optionally substituted, most particularly piperidine or pyrrolidine, optionally substituted.

More generally, and in the context of the invention, a preferred aryl is phenyl, and a preferred heteroaryl is chosen from pyridyl, indolyl, benzimidazolyl, pyrazolyl, thienyl and pyrrolyl, optionally substituted.

Illustrative products of the invention according to its first aspect may be chosen from:

5-(N'-Phenylhydrazinocarbonyl)-1H-thieno[2,3-c]pyrazol-3-yl]-4-methoxybenzamide, 5-(N'-Methyl-N'-phenylhydrazinocarbonyl)-1H-thieno[2,3-c]pyrazol-3-yl]-4-methoxybenzamide, N-[5-(N'-Cyclohexylhydrazinocarbonyl)-1H-thieno[2,3-c]pyrazol-3-yl]-4-methoxybenzamide, N-[5-(N'-Benzyl-N'-phenylhydrazinocarbonyl)-1H-thieno[2,3-c]pyrazol-3-yl]-4-methoxybenzamide, N-{5-[N'-(2-Ethylphenyl)hydrazinocarbonyl]-1H-thieno[2,3-c]pyrazol-3-yl}-4-methoxybenzamide, N-{5-[N'-(2-Fluorophenyl)hydrazinocarbonyl]-1H-thieno[2,3-c]pyrazol-3-yl}-4-methoxybenzamide, 4-Methoxy-N-[5-(N'-o-tolylhydrazinocarbonyl)-1H-thieno[2,3-c]pyrazol-3-yl]benzamide, N-[5-(N'-Methyl-N'-phenylhydrazinocarbonyl)-1H-thieno[2,3-c]pyrazol-3-yl]-4-morpholin-4-ylmethylbenzamide, 4-Bromo-N-[5-(N'-methyl-N'-phenylhydrazinocarbonyl)-1H-thieno[2,3-c]pyrazol-3-yl]benzamide, N-[5-(N'-Methyl-N'-phenylhydrazinocarbonyl)-1H-thieno[2,3-c]pyrazol-3-yl]-4-(4-methylpiperazin-1-ylmethyl)benzamide, 4-(3,5-Dimethylpiperazin-1-ylmethyl)-N-[5-(N'-methyl-N'-phenylhydrazinocarbonyl)-1H-thieno[2,3-c]pyrazol-3-yl]benzamide, 4-(3,5-Dimethylpiperazin-1-ylmethyl)-N-[5-(N'-(4-chlorophenyl)-N'-methylhydrazinocarbonyl)-1H-thieno[2,3-c]pyrazol-3-yl]benzamide, 4-(4-Methylperhydro-1,4-diazepin-1-ylmethyl)-N-[5-(N'-methyl-N'-phenylhydrazinocarbonyl)-1H-thieno[2,3-c]pyrazol-3-yl]benzamide, 4-(4-Methylperhydro-1,4-diazepin-1-ylmethyl)-N-[5-(N'-(4-chlorophenyl)-N'-methylhydrazinocarbonyl)-1H-thieno[2,3-c]pyrazol-3-yl]benzamide, N-[5-(N'-Methyl-N'-phenylhydrazinocarbonyl)-1H-thieno[2,3-c]pyrazol-3-yl]-4-piperazin-1-ylmethylbenzamide, N-{5-[N'-(4-Chlorophenyl)-N'-methylhydrazinocarbonyl]-1H-thieno[2,3-c]pyrazol-3-yl}-4-piperazin-1-ylmethylbenzamide, N-[5-(N'-Methyl-N'-phenylhydrazinocarbonyl)-1H-thieno[2,3-c]pyrazol-3-yl]-4-(3-methylpiperazin-1-ylmethyl)benzamide, N-{5-[N'-(4-Chlorophenyl)-N'-methylhydrazinocarbonyl]-1H-thieno[2,3-c]pyrazol-3-yl}-4-(3-methylpiperazin-1-ylmethyl)benzamide, 4-Diethylaminomethyl-N-[5-(N'-methyl-N'-phenylhydrazinocarbonyl)-1H-thieno[2,3-c]pyrazol-3-yl]benzamide trifluoroacetate, N-{5-[N'-(4-Chlorophenyl)-N'-methylhydrazinocarbonyl]-1H-thieno[2,3-c]pyrazol-3-yl}-4-diethylaminomethylbenzamide, N-[5-(N'-Methyl-N'-phenylhydrazinocarbonyl)-1H-thieno[2,3-c]pyrazol-3-yl]-3-(4-methylpiperazin-1-ylmethyl)benzamide, N-[5-(N'-(4-Chlorophenyl)-N'-methylhydrazinocarbonyl)-1H-thieno[2,3-c]pyrazol-3-yl]-3-(4-methylpiperazin-1-ylmethyl)benzamide, N-[5-(N'-Methyl-N'-phenylhydrazinocarbonyl)-1H-thieno[2,3-c]pyrazol-3-yl]-4-piperid-1-ylmethylbenzamide, N-[5-(N'-(4-Chlorophenyl)-N'-methylhydrazinocarbonyl)-1H-thieno[2,3-c]pyrazol-3-yl]-4-piperid-1-ylmethylbenzamide, N-[5-(N'-Methyl-N'-phenylhydrazinocarbonyl)-1H-thieno[2,3-c]pyrazol-3-yl]-4-pyrrolidin-1-ylmethylbenzamide,
N-[5-(N'-(4-Chlorophenyl)-N'-methylhydrazinocarbonyl)-1H-thieno[2,3-c]pyrazol-3-yl]-4-pyrrolidin-1-ylmethylbenzamide,
4-Azetidin-1-ylmethyl-N-[5-(N'-methyl-N'-phenylhydrazinocarbonyl)-1H-thieno[2,3-c]pyrazol-3-yl]benzamide,
4-{[(2-Dimethylaminoethyl)methylamino]methyl}-N-[5-(N'-methyl-N'-phenylhydrazinocarbonyl)-1H-thieno[2,3-c]pyrazol-3-yl]benzamide,
N-{5-[N'-(4-Chlorophenyl)-N'-methylhydrazinocarbonyl]-1H-thieno[2,3-c]pyrazol-3-yl}-4-{[(2-dimethylaminoethyl)methylamino]methyl}benzamide,
N-[5-(N'-Methyl-N'-phenylhydrazinocarbonyl)-1H-thieno[2,3-c]pyrazol-3-yl]-4-perhydro-1,4-oxazepin-4-ylmethylbenzamide,
N-{5-[N'-(4-Chlorophenyl)-N'-methylhydrazinocarbonyl]-1H-thieno[2,3-c]pyrazol-3-yl}-4-perhydro-1,4-oxazepin-4-ylmethylbenzamide,
N-[5-(N'-Methyl-N'-phenylhydrazinocarbonyl)-1H-thieno[2,3-c]pyrazol-3-yl]-3-morpholin-4-ylmethylbenzamide,
N-{5-[N'-(4-Chlorophenyl)-N'-methylhydrazinocarbonyl]-1H-thieno[2,3-c]pyrazol-3-yl}-3-morpholin-4-ylmethylbenzamide,
4-[(2-Diethylaminoethylamino)methyl]-N-[5-(N'-methyl-N'-phenylhydrazinocarbonyl)-1H-thieno[2,3-c]pyrazol-3-yl]benzamide,
N-{5-[N'-(4-Chlorophenyl)-N'-methylhydrazinocarbonyl]-1H-thieno[2,3-c]pyrazol-3-yl}-4-[(2-diethylaminoethylamino)methyl]benzamide,
4-[(Methylphenylamino)methyl]-N-[5-(N'-methyl-N'-phenylhydrazinocarbonyl)-1H-thieno[2,3-c]pyrazol-3-yl]benzamide,
4-[(Diisopropylamino)methyl]-N-[5-(N'-methyl-N'-phenylhydrazinocarbonyl)-1H-thieno[2,3-c]pyrazol-3-yl]benzamide trifluoroacetate,
N-[5-(N'-Benzylhydrazinocarbonyl)-1H-thieno[2,3-c]pyrazol-3-yl]-4-methoxybenzamide,
4-Methoxy-N-[5-(N'-pyrid-2-ylhydrazinocarbonyl)-1H-thieno[2,3-c]pyrazol-3-yl]benzamide,
N-{5-[N'-(4-Chlorophenyl)-N'-methylhydrazinocarbonyl]-1H-thieno[2,3-c]pyrazol-3-yl}-4-(4-methylpiperazin-1-yl)benzamide,
N-[5-(N'-Benzyl-N'-methylhydrazinocarbonyl)-1H-thieno[2,3-c]pyrazol-3-yl]-4-(4-methylpiperazin-1-yl)benzamide,
N-(Piperid-1-yl)-3-[4-(4-methylpiperazin-1-yl)benzoylamino]-1H-thieno[2,3-c]-pyrazole-5-carboxamide,
N-[5-(N'-Benzylhydrazinocarbonyl)-1H-thieno[2,3-c]pyrazol-3-yl]-4-(4-methylpiperazin-1-yl)benzamide,
N-[5-(N'-Ethyl-N'-phenylhydrazinocarbonyl)-1H-thieno[2,3-c]pyrazol-3-yl]-4-(4-methylpiperazin-1-yl)benzamide,
N-[5-(N'-Benzyl-N'-phenylhydrazinocarbonyl)-1H-thieno[2,3-c]pyrazol-3-yl]-4-(4-methylpiperazin-1-yl)benzamide,
N-[5-(N'-Methyl-N'-phenylhydrazinocarbonyl)-1H-thieno[2,3-c]pyrazol-3-yl]-4-(4-methylpiperazin-1-yl)benzamide,
N-{5-[N'-(4-Chlorophenyl)-N'-cyclobutylmethylhydrazinocarbonyl]-1H-thieno[2,3-c]pyrazol-3-yl}-4-(4-methylpiperazin-1-yl)benzamide,
N-{5-[N'-Ethyl-N'-(4-fluorophenyl)hydrazinocarbonyl]-1H-thieno[2,3-c]pyrazol-3-yl}-4-(4-methylpiperazin-1-yl)benzamide,
N-{5-[N'-(4-Fluorophenyl)-N'-(2-methoxyethyl)hydrazinocarbonyl]-1H-thieno[2,3-c]pyrazol-3-yl}-4-(4-methylpiperazin-1-yl)benzamide,
N-[5-(N'-Ethyl-N'-o-tolylhydrazinocarbonyl)-1H-thieno[2,3-c]pyrazol-3-yl]-4-(4-methylpiperazin-1-yl)benzamide,
N-[5-(N'-Ethyl-N'-m-tolylhydrazinocarbonyl)-1H-thieno[2,3-c]pyrazol-3-yl]-4-(4-methylpiperazin-1-yl)benzamide,
N-[5-(N'-Ethyl-N'-m-tolylhydrazinocarbonyl)-1H-thieno[2,3-c]pyrazol-3-yl]-4-(4-methylpiperazin-1-yl)benzamide,
N-{5-[N'-(4-Fluorophenyl)-N'-isobutylhydrazinocarbonyl]-1H-thieno[2,3-c]pyrazol-3-yl}-4-(4-methylpiperazin-1-yl)benzamide,
N-{5-[N'-(3-Bromophenyl)-N'-ethylhydrazinocarbonyl]-1H-thieno[2,3-c]pyrazol-3-yl}-4-(4-methylpiperazin-1-yl)benzamide,
6-(4-Methyl[1,4]diazepan-1-yl)-N-[5-(N'-methyl-N'-phenylhydrazinocarbonyl)-1H-thieno[2,3-c]pyrazol-3-yl]nicotinamide,
N-[5-(Benzylidenehydrazinocarbonyl)-1H-thieno[2,3-c]pyrazol-3-yl]-4-(4-methylpiperazin-1-yl)benzamide,
N-[5-(N'-Methyl-N'-phenylhydrazinocarbonyl)-1H-thieno[2,3-c]pyrazol-3-yl]-4-(2-morpholin-4-ylethoxy)benzamide,
4-(4-Methyl[1,4]diazepan-1-yl)-N-[5-(N'-methyl-N'-phenylhydrazinocarbonyl)-1H-thieno[2,3-c]pyrazol-3-yl]benzamide.

The products in accordance with the invention may be in achiral form, or racemic form, or in a form enriched in one stereoisomer, or enriched in one enantiomer; and are optionally salified.

According to a second aspect, a subject of the invention is a process for preparing the products according to its first aspect.

In particular, the invention relates to a process for preparing a product of general formula (I) below:

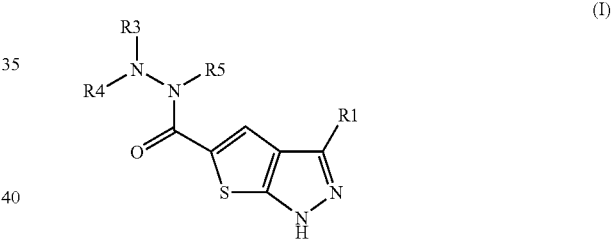

(I)

in which R1 is NHCO(R2), and in which R3, R4 and R5 are as defined above, said product of general formula (I) being obtained by:

(i) coupling between (i-a) an acid of general formula (X) below:

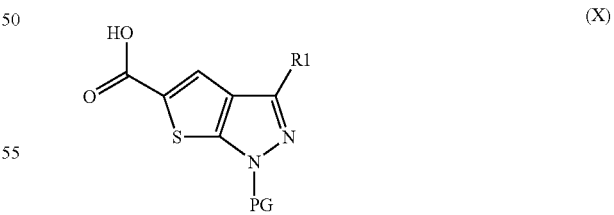

(X)

in which R1 is as defined above, and in which PG is a protecting group for the free endocyclic NH function of the thieno[2,3-c]pyrazole nucleus, and (i-b) a hydrazine (R3)(R4)N—NH(R5) in which R3, R4 and R5 are as defined above, in the presence of a coupling agent and in the presence of a base such as a tertiary amine or an alkali metal carbonate; followed by (ii) cleavage of PG.

The product of general formula (X) may be obtained by saponification of the ester function of the thiophene nucleus of a product of general formula (IX):

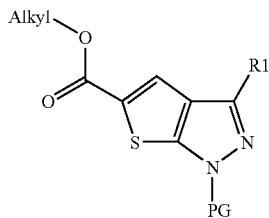
(IX)

in which R1 is as defined above.

The product of general formula (IX) may be obtained by coupling between:

(i) a product of general formula (IIa) below:

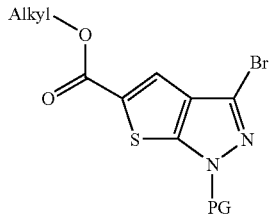
(IIa)

in which Alkyl is as defined above, and in which PG is a protecting group for the free endocyclic NH function of the thieno[2,3-c]pyrazole nucleus, and (ii) a product of general formula (R2)CONH$_2$, in the presence of:
- a catalyst such as copper(I)iodide,
- an amine such as trans-1,2-diaminocyclohexane, trans-1,2-bis(methylamino)cyclohexane or, preferably, N,N'-dimethyl-1,2-diaminoethane, and
- a base such as tripotassium phosphate or cesium carbonate.

The product of general formula (IIa) may be obtained by reaction between an alkyl mercaptoacetate Alkyl-OCO—CH$_2$—SH, in the presence of a base such as sodium carbonate and a compound (IIIa):

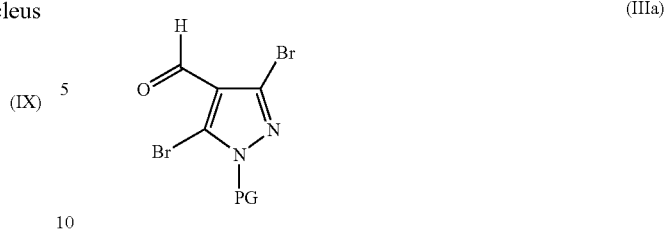
(IIIa)

in which PG is as defined above.

The product of general formula (IIIa) may be obtained by (i) formylation of 3,4,5-tribromopyrazole to obtain 3,5-dibromo-4-formylpyrazole(III), followed by (ii) protection of the endocyclic amine function of (III) via introduction of the protecting group PG.

The protecting group PG may be introduced via:

(i) reaction with ethyl vinyl ether in the presence of an acid such as hydrochloric acid, to obtain a group PG=1-ethoxyethyl, in an inert solvent such as toluene, or;

(ii) reaction with di-tert-butyl dicarbonate in the presence of a base such as triethylamine, pyridine or N,N-dimethylaminopyridine to obtain a group PG=tert-butyloxycarbonyl, in an inert solvent such as dichloromethane.

According to a third aspect, the invention relates to a pharmaceutical composition comprising a product according to its first aspect, in combination with a pharmaceutically acceptable excipient.

According to a fourth aspect, a subject of the invention is the use of a product according to its first aspect, as inhibitor of a protein kinase, preferably chosen from Aurora1, Aurora2, CDK1, CDK2, CDK4, FAK, KDR and Tie2. A particularly preferred kinase is Aurora2.

According to a fifth aspect, a subject of the invention is the use of a product according to its first aspect, for the manufacture of a medicament that is useful for treating a pathological condition, in particular cancer.

According to one variant of the fifth aspect, a subject of the invention is the use of a product according to its first aspect, for the manufacture of a medicament that is useful for treating a pathological condition chosen from psoriasis, glaucoma, leukemias, diseases associated with the central nervous system, inflammations, and diseases associated with deregulation of the JNK proteins.

The compounds of formula (I) may be prepared from the compounds of general formula (II), according to the following general synthetic scheme:

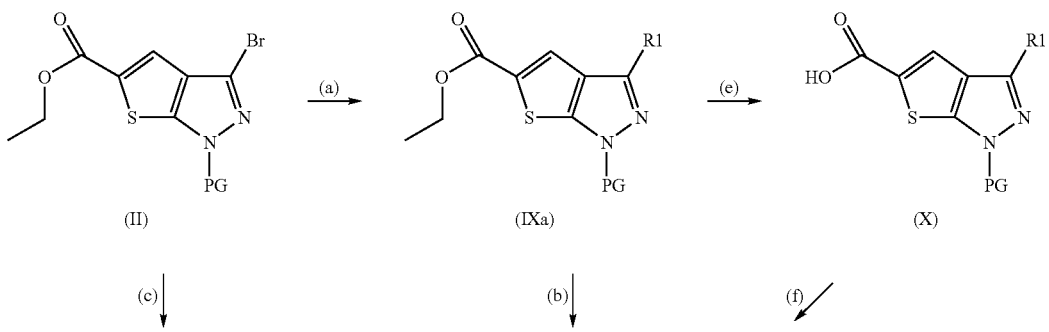

-continued

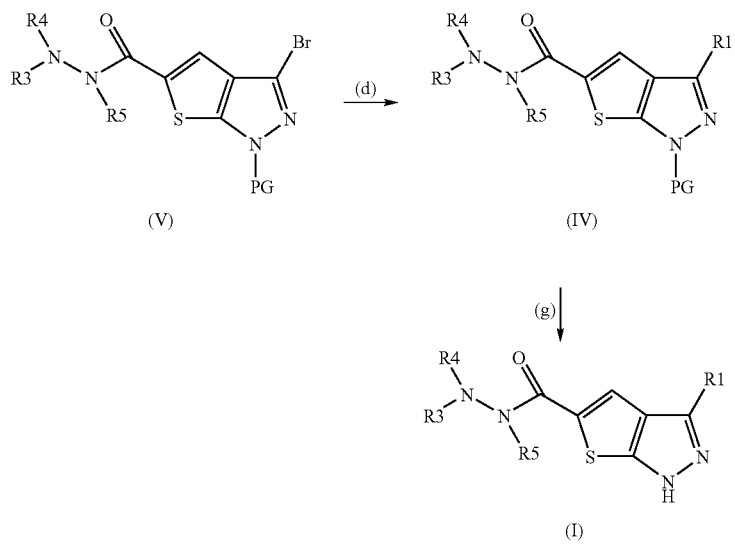

Reactions (a) and (d) may be performed when R1 represents NHCO(R2) in which R2 has the same meaning as above, in the presence of an amide of the type (R2)CONH$_2$, copper(I)iodide, an amine such as trans-1,2-diaminocyclohexane, trans-1,2-bis(methylamino)cyclohexane or, —and this is one of the aspects of the invention—, N,N'-dimethyl-1,2-diaminoethane, and of a base such as tripotassium phosphate or cesium carbonate in an inert solvent such as dioxane, at a temperature of between 20° C. and the boiling point of the reaction medium, according to the general methods described by S. L. Buchwald et al., J. Am. Chem. Soc., 2002, 124, 7421; J. Am. Chem. Soc., 2001, 123, 7727.

Reactions (b) and (c) may be performed in the presence of a derivative of the type (R3)(R4)NN(R5)H in which R3, R4 and R5 have the same meaning as above, and of trimethylaluminum in a solvent such as toluene or dimethylformamide, at a temperature of between 0° C. and the boiling point of the reaction medium.

Reaction (e) is generally performed according to the usual methods that do not affect the rest of the molecule, especially by applying the methods described by T. W. Greene and P. G. M. Wuts, Protective Groups in Organic Synthesis (2nd edition), A. Wiley—Interscience Publication (1991), or by McOmie, Protective Groups in Organic Chemistry, Plenum Press (1973) or by Bradford P. Mundy and Michael G. Ellerd, Name Reactions and Reagents in Organic Synthesis, A. Wiley—Interscience Publication (1988). Reaction (e) may be performed, for example, in basic medium, in the presence of potassium hydroxide or sodium hydroxide, in an inert solvent, such as a mixture of tetrahydrofuran, water and an alcohol (preferably ethanol or methanol), or alternatively of an alcohol alone (preferably ethanol or methanol), at a temperature of between 20° C. and the boiling point of the reaction medium, preferably at the reflux temperature of the reaction medium.

Reaction (f) is preferably performed in the presence of a derivative of the type R3R4NNR5H in which R3, R4 and R5 have the same meaning as above, and of an activating agent of the type such as O-(1H-benzotriazol-1-yl)-N,N,N',N'-tetramethyluronium tetrafluoroborate (TBTU), in the presence of a base (for example triethylamine or diisopropylethylamine), in an inert solvent (for example acetonitrile or dimethylformamide), at a temperature of between 0° C. and the boiling point of the medium, or according to the well-known coupling methods of peptide chemistry (M. Bodanszky et al., Principles of Peptide Synthesis, Springer-Verlag, New York, N.Y., 1984, 9-58) or methods for formation of an amide. Alternatively, reaction (f) may generally be performed according to the usual methods that do not affect the rest of the molecule, especially by applying the methods described by Bradford P. Mundy and Michael G. Ellerd, Name Reactions and Reagents in Organic Synthesis, A. Wiley—Interscience Publication (1988). For example, reaction (f) may be performed under an inert atmosphere (for example under nitrogen or under argon) in the presence of oxalyl chloride, in an inert solvent such as dichloromethane, at a temperature of between 20° C. and the boiling point of the reaction medium, preferably at a temperature in the region of 20° C., or alternatively in the presence of sulfinyl chloride, in an inert solvent such as chloroform, at a temperature of between 20° C. and the boiling point of the reaction medium, preferably at the reflux temperature of the reaction medium, followed by a reaction in the presence of a derivative of the type R3R4NNR5H in which R3, R4 and R5 have the same meaning as above and of a base such as triethylamine or pyridine, in an inert solvent such as dimethylformamide, at a temperature of between 20° C. and the boiling point of the reaction medium.

The deprotection reaction (g) may be performed (when PG represents a 1-ethoxyethyl group) in the presence of a mineral acid such as hydrochloric acid, in a solvent such as tetrahydrofuran or water, at a temperature of between 20° C. and the boiling point of the reaction medium, or alternatively according to the well-known methods for deprotection of the amine function (T. W. Greene et al. in Protective Groups in Organic Synthesis, 3rd edition, 1999, Wiley Interscience).

The compounds of general formula (IIa) may be prepared from 3,4,5-tribromopyrazole, according to the following general synthetic scheme:

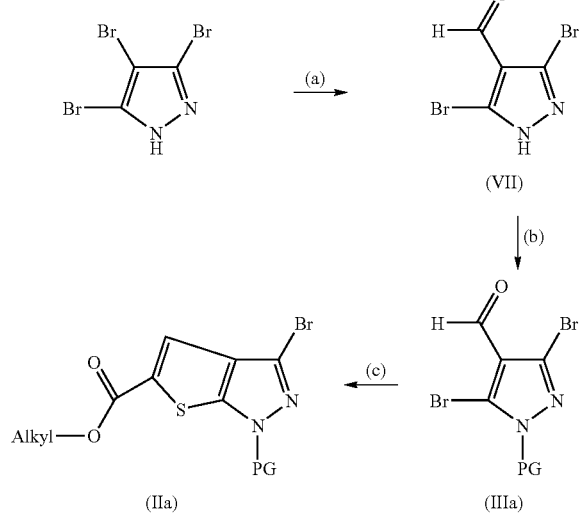

Reaction (a) may be performed in the presence of an organolithium reagent such as n-butyllithium, in the presence of dimethylformamide, in an inert solvent such as diethyl ether or tetrahydrofuran, at a temperature of between −78° C. and room temperature.

The protection reaction (b) may be performed in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting an amine function (T. W. Greene et al. in Protective Groups in Organic Synthesis, third edition, 1999, Wiley—Interscience).

Reaction (c) may be performed in the presence of ethyl mercaptoacetate, in the presence of a base such as sodium carbonate, in an inert solvent such as an alcohol (preferably ethanol), at a temperature of between 20° C. and the boiling point of the reaction medium.

Alternatively, when R1 represents NHCO(R2) in which R2 has the same meaning as above, the compounds of formula (I) may be prepared from the compounds of general formula (XIV), according to the following general synthetic scheme:

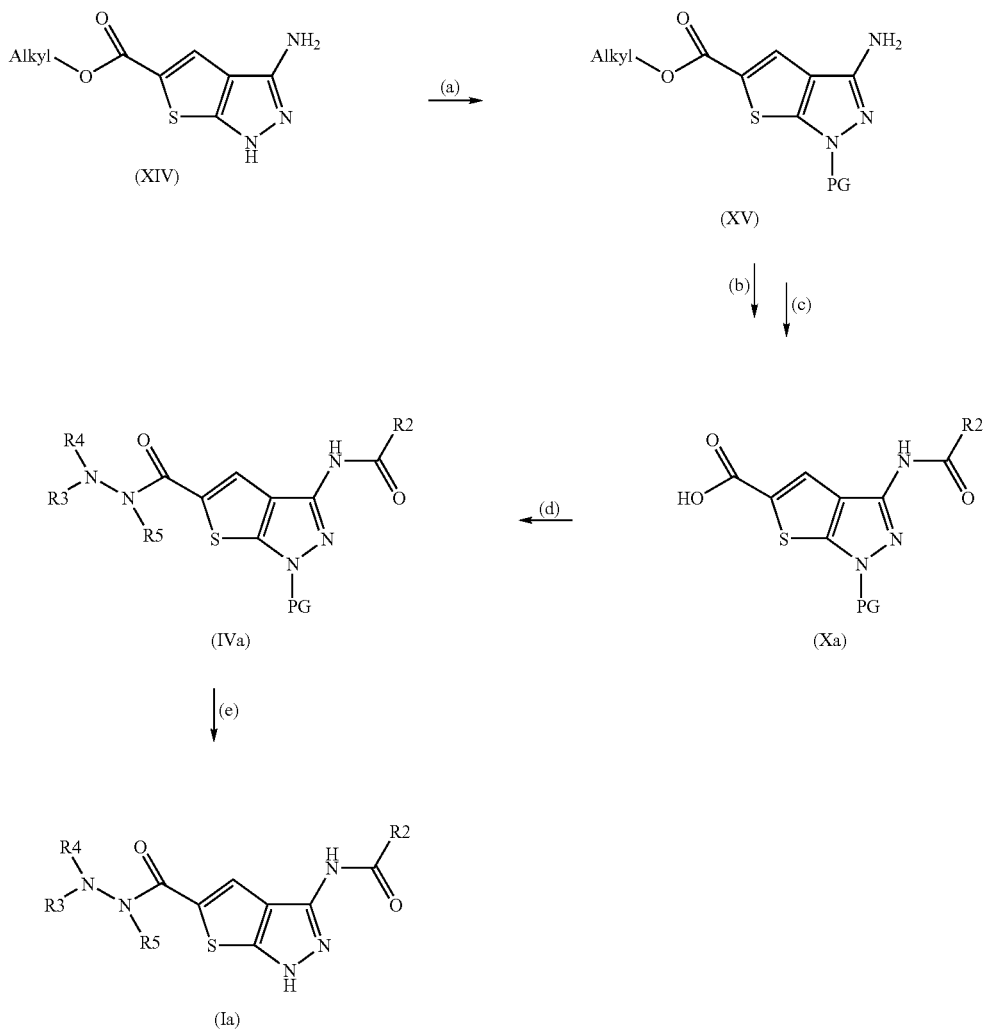

The protection reaction (a) may be performed (when P represents a tert-butyloxycarbonyl group) using di-tert-butyl dicarbonate in the presence of a base such as triethylamine or pyridine and optionally in the presence of N,N-dimethylaminopyridine, in an inert solvent (for example dichloromethane), at a temperature of between −10° C. and the boiling point of the reaction medium, or alternatively (when P represents a 1-ethoxyethyl group) in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting an amine function (T. W. Greene et al. in Protective Groups in Organic Synthesis, third edition, 1999, Wiley—Interscience).

Reaction (b) may be performed:

using an acid chloride (R2)C(O)Cl in which R2 has the same meaning as above, in the presence of a base, for instance triethylamine, pyridine, diisopropylethylamine, potassium carbonate or sodium carbonate, in an inert solvent (for example dimethylformamide or tetrahydrofuran) or in the organic base itself, at a temperature of between 0° C. and the boiling point of the reaction medium (G. Daidone et al., Heterocycles, 1996, 43(11), 2385);

using an anhydride ((R2)CO)$_2$O in which R2 has the same meaning as above, in an inert solvent (for example dimethylformamide, tetrahydrofuran or dichloromethane) or in the anhydride itself, at a temperature of between 0° C. and the boiling point of the reaction medium (F. Albericio, Synth. Commun., 2001, 31(2), 225, G. Procter, Tetrahedron, 1995, 51(47), 12837);

using an acid (R2)C(O)OH in which R2 has the same meaning as above, in the presence of an activating agent such as O-(7-azabenzotriazol-1-yl)-N,N,N',N'-tetramethyluronium hexafluorophosphate (HATU), in the presence of a base (for example pyridine, diisopropylethylamine or triethylamine), in an inert solvent (for example dimethylformamide), at a temperature of between 0° C. and the boiling point of the reaction medium, or according to the well-known coupling methods of peptide chemistry (M. Bodanszky et al., Principles of Peptide Synthesis, Springer-Verlag, New York, N.Y., 1984, 9-58) or methods for the formation of an amide.

Reaction (c) is generally performed according to the usual methods that do not affect the rest of the molecule, especially by application of the methods described by T. W. Greene and P. G. M. Wuts, Protective Groups in Organic Synthesis (2nd edition), A. Wiley—Interscience Publication (1991), or by McOmie, Protective Groups in Organic Chemistry, Plenum Press (1973) or by Bradford P. Mundy et Michael G. Ellerd, Name Reactions and Reagents in Organic Synthesis, A. Wiley—Interscience Publication (1988). Reaction (c) may be performed, for example, in basic medium, in the presence of potassium hydroxide or sodium hydroxide, in an inert solvent such as a mixture of tetrahydrofuran, water and an alcohol (preferably ethanol or methanol) or of an alcohol alone (preferably ethanol or methanol), at a temperature of between 20° C. and the boiling point of the reaction medium, preferably at the reflux temperature of the reaction medium.

Reaction (d) is preferably performed in the presence of a derivative of the type R3R4NNR5H, in which R3, R4 and R5 have the same meaning as above, and of an activating agent of the type such as O-(1H-benzotriazol-1-yl)-N,N,N',N'-tetramethyluronium tetrafluoroborate (TBTU), for instance, in the presence of a base (for example triethylamine or diisopropylethylamine) in an inert solvent (for example acetonitrile or dimethylformamide), at a temperature of between 0° C. and the boiling point of the medium, or according to the well-known coupling methods of peptide chemistry (M. Bodanszky et al., Principles of Peptide Synthesis, Springer-Verlag, New York, N.Y., 1984, 9-58) or methods for the formation of an amide. Alternatively, reaction (d) may generally be performed according to the usual methods that do not affect the rest of the molecule, especially by application of the methods described by Bradford P. Mundy and Michael G. Ellerd, Name Reactions and Reagents in Organic Synthesis, A. Wiley-Interscience Publication (1988). For example, reaction (d) may be performed under an inert atmosphere (for example under nitrogen or under argon) in the presence of oxalyl chloride, in an inert solvent such as dichloromethane, at a temperature of between 20° C. and the boiling point of the reaction medium, preferably at a temperature in the region of 20° C., or alternatively in the presence of sulfinyl chloride, in an inert solvent such as chloroform, at a temperature of between 20° C. and the boiling point of the reaction medium, preferably at the reflux temperature of the reaction medium, followed by a reaction in the presence of a derivative of the type R3R4NNR5H, in which R3, R4 and R5 have the same meaning as above, and of a base such as triethylamine or pyridine, in an inert solvent such as dimethylformamide, at a temperature of between 20° C. and the boiling point of the reaction medium.

The deprotection reaction (e) may be performed (when PG represents a tert-butyloxycarbonyl group) in the presence of iodotrimethylsilane, or in acidic medium (for example trifluoroacetic acid, or hydrochloric acid in a solvent such as dichloromethane or dioxane) at a temperature of between 0° C. and the boiling point of the reaction medium, or in basic medium (potassium carbonate in a solvent such as an alcohol (preferably methanol) at a temperature of between 0° C. and the boiling point of the reaction medium and optionally with microwave irradiation), or in neutral medium in a solvent such as an alcohol (preferably methanol) with microwave irradiation, or alternatively (when PG represents a 1-ethoxyethyl group) in the presence of a mineral acid such as hydrochloric acid, in a solvent such as tetrahydrofuran or water, at a temperature of between 20° C. and the boiling point of the reaction medium, or alternatively according to the well-known methods for deprotecting an amine function (T. W. Greene at al. in Protective Groups in Organic Synthesis, third edition, 1999, Wiley-Interscience).

The compounds of general formula (XVa) may be prepared from ethyl 3-amino-4-cyano-5-methylsulfanylthiophene-2-carboxylate, according to the following general synthetic scheme:

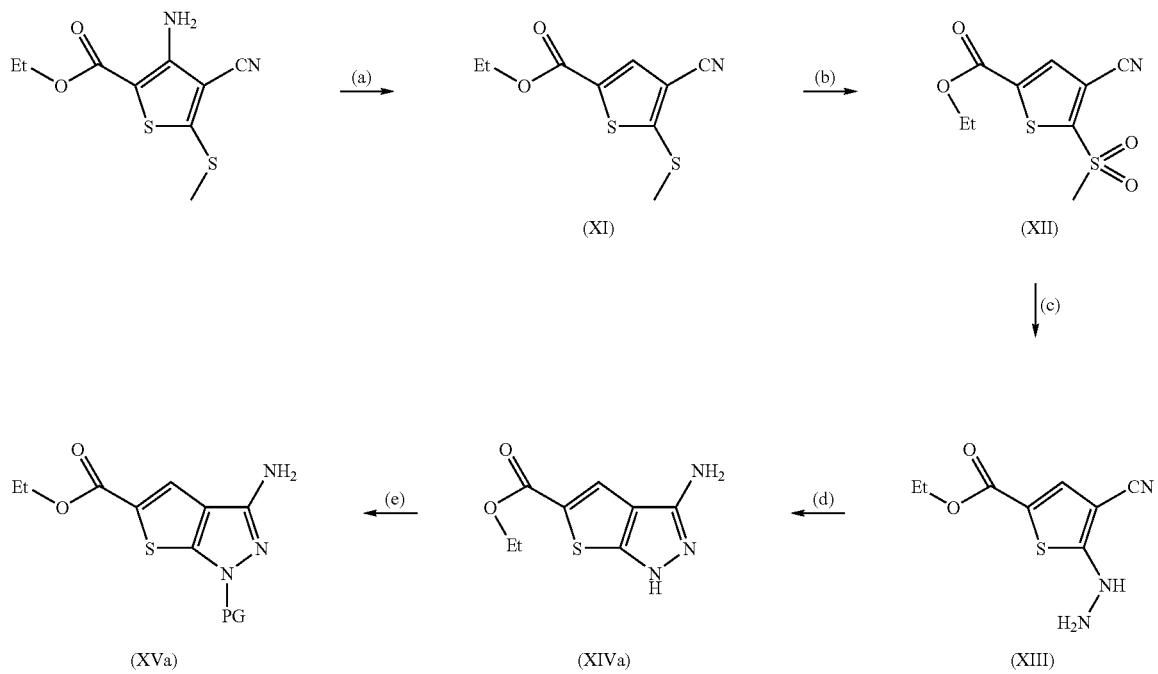

Reaction (a) may be performed in the presence of isopentyl nitrite and Cu(II), in an inert solvent such as dimethylformamide, at a temperature of between 20° C. and the boiling point of the reaction medium.

The oxidation reaction (b) may be performed in the presence of 3-chloroperoxybenzoic acid, in an inert solvent such as dichloromethane, at a temperature of between −20° C. and room temperature.

Reaction (c) may be performed in the presence of hydrazine, in an inert solvent such as an alcohol (preferably ethanol), at a temperature of between 20° C. and the boiling point of the reaction medium.

The cyclization reaction (d) may be performed in the presence of a mineral acid such as concentrated hydrochloric acid or concentrated sulfuric acid, in an inert solvent such as an alcohol (preferably ethanol), at a temperature of between 20° C. and the boiling point of the reaction medium.

The protection reaction (e) may be performed (when PG represents a tert-butyloxycarbonyl group) using di-tert-butyl dicarbonate in the presence of a base such as triethylamine or pyridine and optionally in the presence of N,N-dimethylaminopyridine, in an inert solvent (for example dichloromethane) at a temperature of between −10° C. and the boiling point of the reaction medium, or alternatively (when PG represents a 1-ethoxyethyl group) in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting the amine function (T. W. Greene et al. in Protective Groups in Organic Synthesis, 3rd edition, 1999, Wiley-Interscience).

The synthesis of ethyl 3-amino-4-cyano-5-methylsulfanylthiophene-2-carboxylate is described in Synthesis 2003, 735.

Alternatively, when R1 represents NHCO(R2) in which R2 has the same meaning as above, the compounds of formula (I) may be prepared from the compounds of general formula (XIV), according to the following general synthetic scheme:

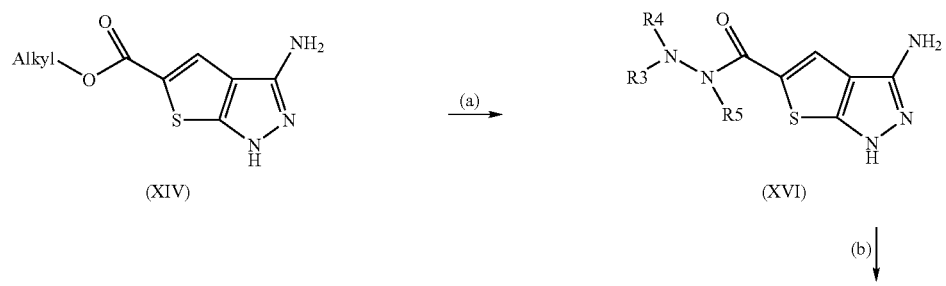

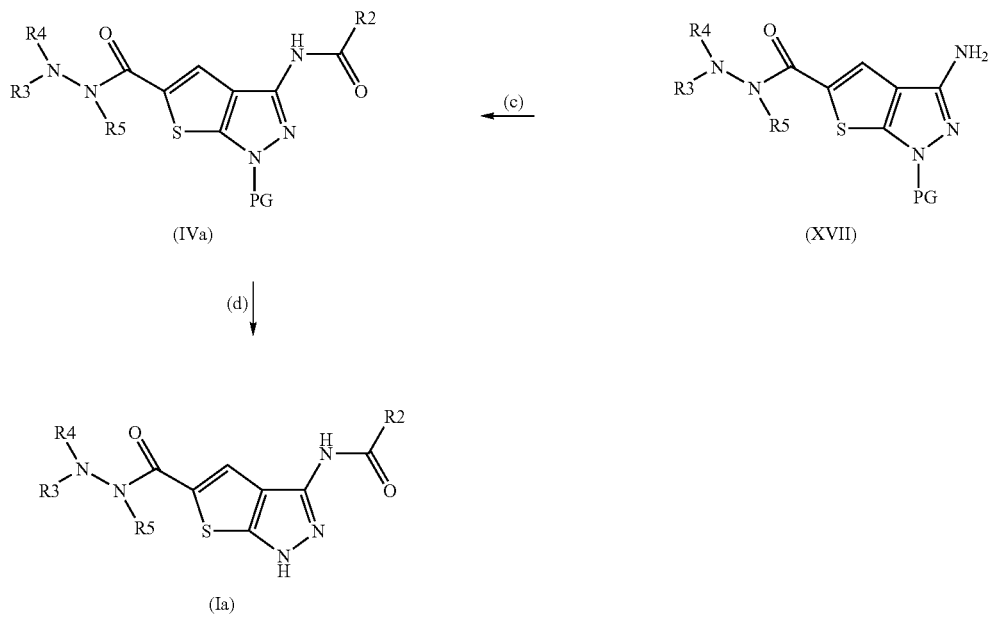

(IVa)

(d) ↓

(Ia)

Reaction (a) may be performed in the presence of a derivative of the type (R3)(R4)NN(R5)H, in which R3, R4 and R5 have the same meaning as above, and of trimethylaluminum in a solvent such as toluene or dimethylformamide, at a temperature of between 0° C. and the boiling point of the reaction medium.

The protection reaction (b) may be performed (when PG represents a tert-butyloxycarbonyl group) using di-tert-butyl dicarbonate in the presence of a base such as triethylamine or pyridine and optionally in the presence of N,N-dimethylaminopyridine, in an inert solvent (for example dichloromethane) at a temperature of between −10° C. and the boiling point of the reaction medium, or alternatively (when PG represents a 1-ethoxyethyl group) in the presence of ethyl vinyl ether, in the presence of a catalytic amount of an acid such as hydrochloric acid, in an inert solvent such as toluene, at a temperature of between 20° C. and the boiling point of the reaction medium, or according to the well-known methods for protecting the amine function (T. W. Greene et al. in Protective Groups in Organic Synthesis, 3rd edition, 1999, Wiley-Interscience).

Reaction (c) may be performed:

using an acid chloride (R2)C(O)Cl in which R2 has the same meaning as above, in the presence of a base, for instance triethylamine, pyridine, diisopropylethylamine, potassium carbonate or sodium carbonate, in an inert solvent (for example dimethylformamide or tetrahydrofuran) or in the organic base itself, at a temperature of between 0° C. and the boiling point of the reaction medium (G. Daidone et al., Heterocycles, 1996, 43(11), 2385);

using an anhydride ((R2)CO)₂O in which R2 has the same meaning as above, in an inert solvent (for example dimethylformamide, tetrahydrofuran or dichloromethane) or in the anhydride itself, at a temperature of between 0° C. and the boiling point of the reaction medium (F. Albericio, Synth. Commun., 2001, 31(2), 225, G. Procter, Tetrahedron, 1995, 51(47), 12837);

using an acid (R2)C(O)OH in which R2 has the same meaning as above, in the presence of an activating agent such as O-(7-azabenzotriazol-1-yl)-N,N,N',N'-tetramethyluronium hexafluorophosphate (HATU) in the presence of a base (for example pyridine, diisopropylethylamine or triethylamine) in an inert solvent (for example dimethylformamide), at a temperature of between 0° C. and the boiling point of the reaction medium, or according to the well-known coupling methods of peptide chemistry (M. Bodanszky et al., Principles of Peptide Synthesis, Springer-Verlag, New York, N.Y., 1984, 9-58) or methods for the formation of an amide.

The deprotection reaction (d) may be performed (when PG represents a tert-butyloxycarbonyl group) in the presence of iodotrimethylsilane, or in acidic medium (for example trifluoroacetic acid, or hydrochloric acid in a solvent such as dichloromethane or dioxane), at a temperature of between 0° C. and the boiling point of the reaction medium, or in basic medium (potassium carbonate in a solvent such as an alcohol (preferably methanol) at a temperature of between 0° C. and the boiling point of the reaction medium and optionally with microwave irradiation), or in neutral medium in a solvent such as an alcohol (preferably methanol) with microwave irradiation; or alternatively (when PG represents a 1-ethoxyethyl group) in the presence of a mineral acid such as hydrochloric acid, in a solvent such as tetrahydrofuran or water, at a temperature of between 20° C. and the boiling point of the reaction medium, or alternatively according to the well-known methods for deprotecting the amine function (T. W. Greene et al. in Protective Groups in Organic Synthesis, 3rd edition, 1999, Wiley-Interscience).

Alternatively, when R1 represents NHCO(R2) in which R2 has the same meaning as above, the compounds of formula (XVI) may be prepared from the compounds of general formula (XI), according to the following general synthetic scheme:

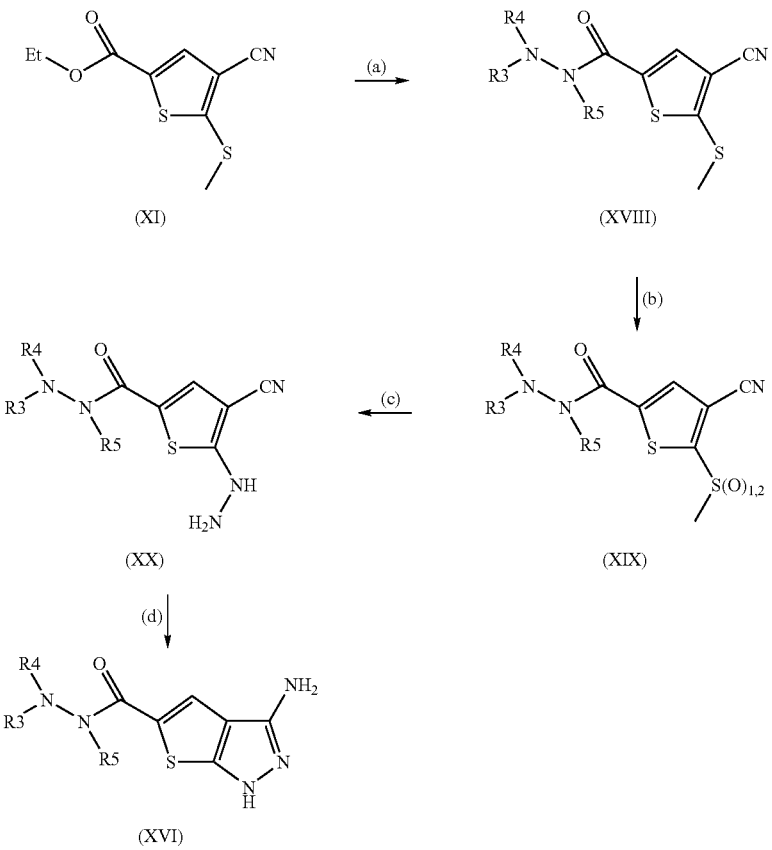

Reaction (a) may be performed in the presence of a derivative of the type (R3)(R4)NN(R5)H, in which R3, R4 and R5 have the same meaning as above, and of trimethylaluminum in a solvent such as toluene or dimethylformamide, at a temperature of between 0° C. and the boiling point of the reaction medium.

The oxidation reaction (b) may be performed in the presence of oxone® (potassium peroxymonosulfate) or 3-chloroperoxybenzoic acid, in an inert solvent such as a mixture of tetrahydrofuran or dimethylformamide and water in the first case or dichloromethane in the second case, at a temperature of between −20° C. and room temperature.

Reaction (c) may be performed in the presence of hydrazine, in an inert solvent such as an alcohol (preferably ethanol) at a temperature of between 20° C. and the boiling point of the reaction medium.

The cyclization reaction (d) may be performed in the presence of a mineral acid such as concentrated hydrochloric acid or concentrated sulfuric acid, in an inert solvent such as an alcohol (preferably ethanol), at a temperature of between 20° C. and the boiling point of the reaction medium.

The compounds of formula (Ib) in which R1 represents NHCO(R2) in which R2 represents a phenyl group substituted with a group of the type —CH2NR6R7, R6 and R7 being independently selected from the group consisting of —H, ($C_1$-$C_6$)alkyl, aryl, heteroaryl, —($C_1$-$C_6$)alkyl-aryl and —($C_1$-$C_6$)alkyl-heteroaryl, optionally substituted, or alternatively (R6 and R7) being linked together to form a saturated or unsaturated, 2- to 10-membered monocyclic or bicyclic heterocycle containing from 1 to 5 heteroatoms chosen from N, O and S, may be prepared from the compounds of general formula (IVb), according to the following general synthetic scheme:

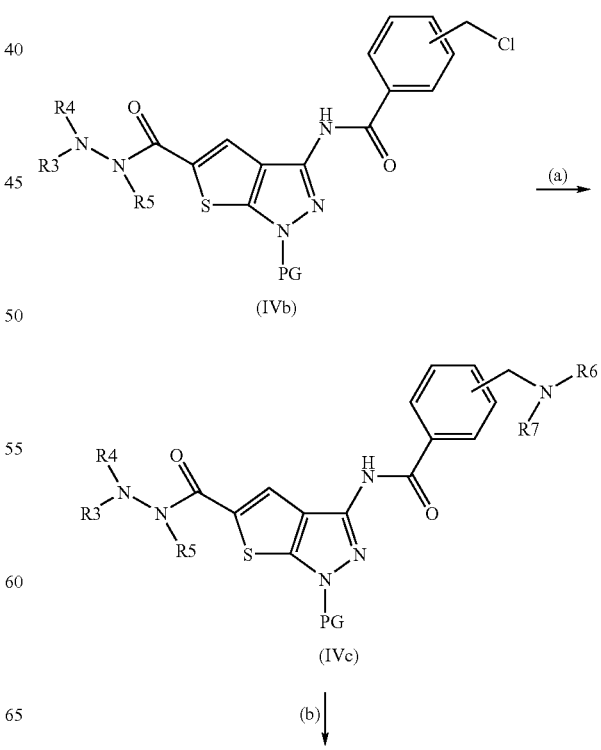

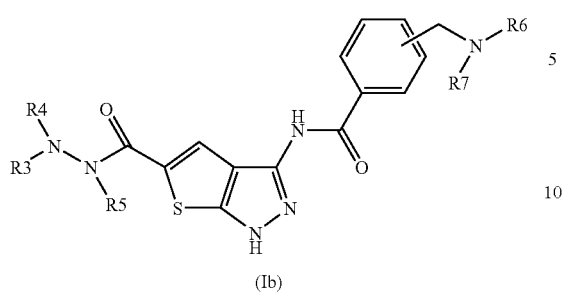

(Ib)

Reaction (a) may be performed in the presence of an amine of the type HNR6R7, in the presence of a salt such as tetrabutylammonium iodide in an inert solvent such as dimethylformamide, at a temperature of between 20° C. and the boiling point of the reaction medium.

The deprotection reaction (b) may be performed (when PG represents a tert-butyloxycarbonyl group) in the presence of iodotrimethylsilane, or in acidic medium (for example trifluoroacetic acid, or hydrochloric acid in a solvent such as dichloromethane or dioxane), at a temperature of between 0° C. and the boiling point of the reaction medium, or in basic medium (potassium carbonate in a solvent such as an alcohol (preferably methanol) at a temperature of between 0° C. and the boiling point of the reaction medium and optionally with microwave irradiation), or in neutral medium in a solvent such as an alcohol (preferably methanol) with microwave irradiation; or alternatively (when PG represents a 1-ethoxyethyl group) in the presence of a mineral acid such as hydrochloric acid, in a solvent such as tetrahydrofuran or water, at a temperature of between 20° C. and the boiling point of the reaction medium, or alternatively according to the well-known methods for deprotecting the amine function (T. W. Greene et al. in Protective Groups in Organic Synthesis, 3rd edition, 1999, Wiley-Interscience).

The derivatives of the type (R3)(R4)NN(R5)H, in which R3 represents an Aryl group and more particularly a substituted phenyl group, R4 represents an alkyl group and R5 represents a hydrogen atom, may be prepared from the compounds of general formula (XXI), according to the following general synthetic scheme:

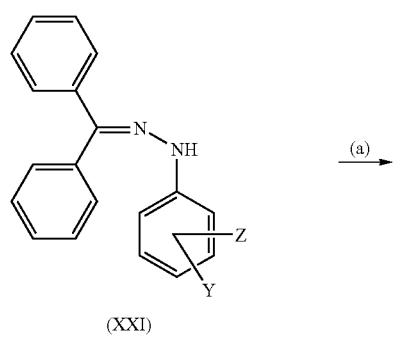

(XXI)

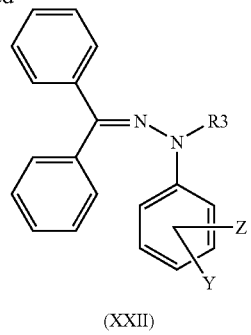

(XXII)

(b)↓

H₂N group with R3

Reaction (a) may be performed in the presence of a base such as an organolithium reagent, in the presence of an alkyl halide, in an inert solvent such as tetrahydrofuran, at a temperature of between −80° C. and 25° C.

The cleavage reaction (b) may be performed in the presence of a mineral acid such as hydrochloric acid, in an inert solvent such as tetrahydrofuran, at a temperature of between 25° C. and the boiling point of the reaction medium.

The compounds of general formula (XXI) in which Y and Z represent, independently and more particularly, a hydrogen atom, or a halogen or alkyl group, may be prepared from the compounds of general formula (XXIII), according to the following general synthetic scheme:

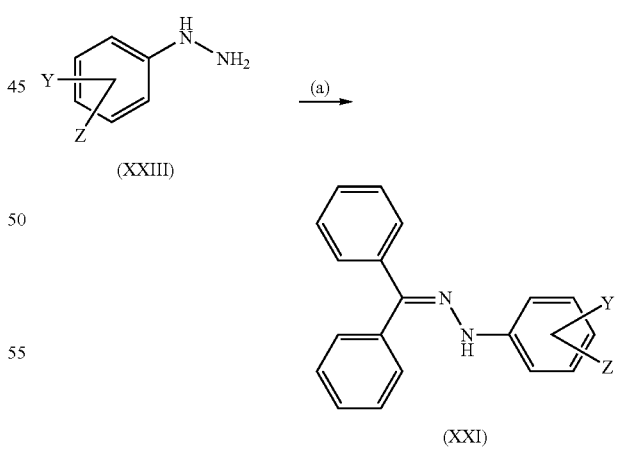

(XXIII)

(XXI)

Reaction (a) may be performed in the presence of benzophenone, in the presence of a mineral acid such as sulfuric acid or hydrochloric acid, in an inert solvent such as an alcohol, preferably ethanol, at a temperature of between 25° C. and the boiling point of the reaction medium.

Alternatively, the compounds of general formula (XXI) in which Y and Z represent, independently and more particularly, a hydrogen atom, or a halogen or alkyl group, may be prepared from the compounds of general formula (XXIV), according to the following general synthetic scheme:

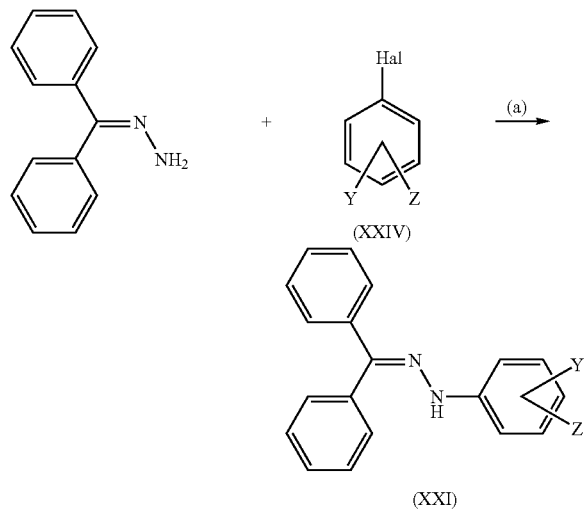

Reaction (a) may be performed in the presence of benzyhydrylidenehydrazine, of a compound of general formula (XXIV) in which Y and Z represent, independently and more particularly, a hydrogen atom, or a halogen or alkyl group and in which Hal more particularly represents a bromine or chlorine atom, of a palladium(II) derivative such as palladium(II) diacetate, of a phosphine ligand and of a base such as sodium hydroxide, in an inert solvent such as an alcohol (preferably tert-amyl alcohol), at a temperature of between 20° C. and the boiling point of the reaction medium, according to the general methods described by J.-M. Campagne et al., Tetrahedron, 2002, 58, 2041.

It is understood to those skilled in the art that, in order to perform the processes according to the invention described previously, it may be necessary to introduce protecting groups for the amine and carboxyl functions in order to avoid side reactions. These groups are those that can be removed without affecting the rest of the molecule. Examples of protecting groups for the amine function that may be mentioned include 1-ethoxyethyl, which may be removed in the presence of a mineral acid such as hydrochloric acid (in a solvent such as, for example, tetrahydrofuran or water), tert-butylcarbamate, which may be removed using iodotrimethylsilane or in acidic medium (for example trifluoroacetic acid, or hydrochloric acid in a solvent such as dichloromethane or dioxane), benzyl carbamate, which may be removed in the presence of hydrogen or in the presence of a mixture of a thiol (for example benzenethiol) and a Lewis acid (for example boron trifluoride etherate), acetyl, which may be removed in acidic medium (for example hydrochloric acid), benzoyl, which may be removed in acidic medium (for example hydrochloric acid), 2-trimethylsilanylethoxymethyl, which may be removed, for example, in the presence of tetrabutylammonium fluoride or in acidic medium (for example hydrochloric acid). Protecting groups for the carboxyl function that may be mentioned include esters (for example methoxymethyl ester, benzyl ester or methyl ester), which may be removed via the methods described in T. W. Greene et al. in Protective Groups in Organic Synthesis, third edition, 1999, Wiley-Interscience.

The compounds of formula (I) are isolated and may be purified via the usual known methods, for example by crystallization, chromatography or extraction.

The enantiomers and diastereoisomers of the compounds of formula (I) also form part of the invention.

The compounds of formula (I) comprising a basic residue may be optionally converted into addition salts with a mineral or organic acid via the action of such an acid in an organic solvent such as an alcohol, a ketone, an ether or a chlorinated solvent.

The compounds of formula (I) comprising an acid residue may be optionally converted into metal salts or into addition salts with nitrogenous bases according to the methods that are known per se. These salts may be obtained via the action of a metallic base (for example alkali metal or alkaline-earth metal base), ammonia, an amine or an amine salt on a compound of formula (I), in a solvent. The salt formed is separated out by the usual methods.

These salts also form part of the invention.

When a product according to the invention contains at least one free basic function, pharmaceutically acceptable salts may be prepared by reaction between said product and a mineral or organic acid. Pharmaceutically acceptable salts include the chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, propanesulfonates, xylenesulfonates, salicylates, cinnamates, glutamates, aspartates, glucuronates and galacturonates.

When a product according to the invention contains at least one free acid function, pharmaceutically acceptable salts may be prepared by reaction between said product and a mineral or organic base. Pharmaceutically acceptable bases include hydroxides of cations of alkali metals or alkaline-earth metals such as Li, Na, K, Mg or Ca, and basic amine compounds such as ammonia, arginine, lysine, histidine, piperidine, morpholine, piperazine or triethylamine.

The invention is also described by the examples that follow, which are given as illustrations of the invention.

EXAMPLE 1

Preparation of 5-(N'-phenylhydrazinocarbonyl)-1H-thieno[2,3-c]pyrazol-3-yl]-4-methoxybenzamide

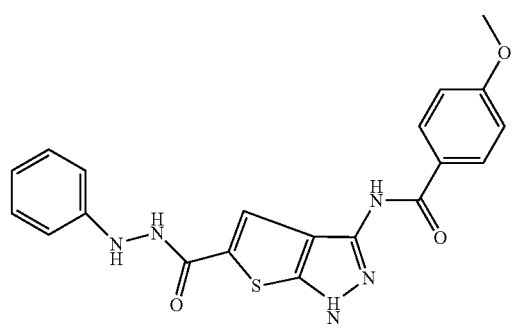

1-(1-Ethoxyethyl)-3-(4-methoxybenzoylamino)-1H-thieno[2,3-c]pyrazole-5-carboxylic acid (0.3 g, 0.77 mmol), O-(1H-benzotriazol-1-yl)-N,N,N',N'-tetramethyluronium tetrafluoroborate (TBTU) (0.247 g, 0.77 mmol, 1 eq.), dimethylformamide (3.85 mL) and phenylhydrazine (0.151 mL, 1.54 mmol, 2 eq.) are successively introduced into a 20 mL round-bottomed flask under argon. Triethylamine (0.322 mL, 2.31 mmol, 3 eq.) is added to the reaction mixture. The mixture is stirred at a temperature in the region of 60° C. for 15 hours. The solvent is then evaporated off under vacuum and the residual oil is diluted with 15 mL of ethyl acetate and 10 mL of water. The aqueous phase is isolated and then acidified to pH 4-5, after which it is extracted with ethyl acetate (3×15 mL). The combined organic phases are dried over magnesium sulfate and concentrated to dryness under reduced pressure. The residue is purified by flash chromatography on silica gel, eluting with a 1:1 ethyl acetate/heptane mixture. The product obtained in oil form (0.310 g, 84%, Rf=0.47 (1:9 MeOH/dichloromethane)) is placed without further purification in 5 mL of tetrahydrofuran and 2.5 mL of 2.5 N hydrochloric acid. The reaction mixture is then heated at a temperature in the region of 50° C. for 2 hours and is then cooled to room temperature. 15 mL of water are then added to the mixture. A precipitate forms. The tetrahydrofuran evaporated off and the aqueous phase is neutralized with 5 N NaOH. The precipitate formed is filtered off and then washed with water. The beige-colored solid is dried in an oven at a temperature in the region of 60° C. under vacuum. The dry solid is then dissolved in acetone and precipitated from heptane. The 5-(N'-phenylhydrazinocarbonyl)-1H-thieno[2,3-c]pyrazol-3-yl]-4-methoxybenzamide thus obtained (86 mg, 33%) has a purity of 95%. Overall yield=28%. $^1$H NMR (400 MHz, (CD$_3$)$_2$SO-d$_6$, δ in ppm): 3.85 (s, 3H); 6.72 (broad t, J=7.5 Hz, 1H); 6.76 (broad d, J=8.0 Hz, 2H); 7.05 (broad d, J=8.0 Hz, 2H); 7.15 (broad t, J=7.5 Hz, 2H); 7.85 (broad s, 1H); 8.09 (broad d, J=8.0 Hz, 2H); 8.19 (broad s, 1H); 10.45 (broad m, 1H); 11.0 (broad m, 1H); 12.9 (broad m, 1H). LC/MS: m=407. ES m/z=408 MH$^+$ 1-(1-Ethoxyethyl)-3-(4-methoxybenzoylamino)-1H-thieno[2,3-c]pyrazol-5-carboxylic acid

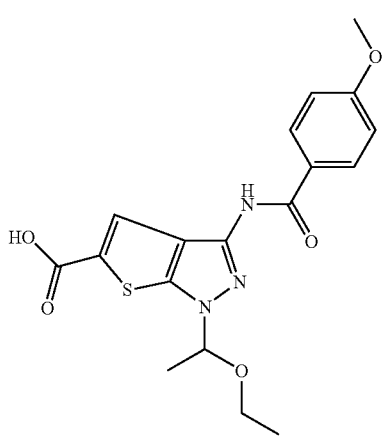

Ethyl 3-bromo-1-(1-ethoxyethyl)-1H-thieno[2,3-c]pyrazole-5-carboxylate (10 g, 28 mmol), 4-methoxybenzamide (7.39 g, 48 mmol, 1.7 eq.), copper(I)iodide (0.548 g, 2.88 mmol, 0.1 eq.), preground tripotassium phosphate (18.34 g, 86 mmol, 3 eq.) and 180 mL of anhydrous dioxane degassed beforehand with argon are introduced into a 500 mL round-bottomed flask under argon. 0.306 mL (2.88 mmol, 0.1 eq.) of N,N'-dimethylethylenediamine is added to this suspension by syringe. The reaction mixture is then heated to a temperature in the region of 110° C. for a period of 24 hours. The dioxane is then evaporated off under vacuum and the residue is diluted with ethyl acetate (300 mL) and 150 mL of water. The organic phase is washed once with 100 mL of water and is then dried over magnesium sulfate and concentrated to dryness under reduced pressure. The residue is purified by chromatography on silica gel, eluting with an ethyl acetate/heptane mixture (1:1). The pale yellow oil obtained after purification corresponds to ethyl 1-(1-ethoxyethyl)-3-(4-methoxybenzoylamino)-1H-thieno[2,3-c]pyrazole-5-carboxylate (7.41 g, 64%). The combined aqueous phases are acidified with 5 N hydrochloric acid to pH 5-6. A thick precipitate appears, which is extracted with (2×100 mL) of ethyl acetate. The organic phase is in turn dried over magnesium sulfate and concentrated to dryness under reduced pressure. The white solid obtained after evaporation is triturated in a heptane/dimethyl ether mixture (1:1). After filtration, 1-(1-ethoxyethyl)-3-(4-methoxybenzoylamino)-1H-thieno[2,3-c]pyrazole-5-carboxylic acid is obtained in the form of a white solid (1.27 g, 11%). The ethyl 1-(1-ethoxyethyl)-3-(4-methoxybenzoylamino)-1H-thieno[2,3-c]pyrazole-5-carboxylate is subjected to saponification using 50 mL of tetrahydrofuran and 20 mL of 5 N sodium hydroxide at a temperature in the region of 50° C. for 5 hours. The tetrahydrofuran is then evaporated off, the aqueous phase is diluted with 150 mL of water and the pH is adjusted to 3-4 with 5 N hydrochloric acid. The white precipitate obtained is filtered off and washed with water, and then dried under vacuum at a temperature in the region of 60° C. 7.04 g of 1-(1-ethoxyethyl)-3-(4-methoxybenzoylamino)-1H-thieno[2,3-c]pyrazole-5-carboxylic acid are thus obtained, i.e. 98%, which product is used directly in the following step.

Ethyl 3-bromo-1-(1-ethoxyethyl)-1H-thieno[2,3-c]pyrazole-5-carboxylate

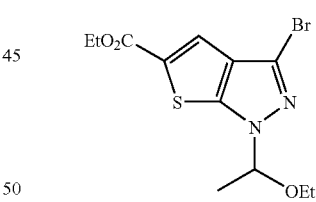

1.19 g (3.81 mmol) of 3,5-dibromo-1-(1-ethoxyethyl)-1H-pyrazole-4-carboxaldehyde are introduced with stirring into 50 mL of ethanol under an argon atmosphere at a temperature in the region of 20° C., followed by addition of 0.4 g (3.81 mmol) of sodium carbonate and 0.42 mL (3.81 mmol) of ethyl 2-mercaptoacetate. The reaction mixture is then refluxed for 2 hours, and then concentrated to dryness under reduced pressure (2.7 kPa). The residue is taken up in 60 mL of water and 60 mL of dichloromethane, and the phases are separated by settling. The organic phase is dried over magnesium sulfate and then concentrated to dryness under reduced pressure (2.7 kPa). 1.17 g of ethyl 3-bromo-1-(1-ethoxyethyl)-1H-thieno[2,3-c]pyrazole-5-carboxylate are thus obtained in the form of a pale yellow oil that crystallizes to give cream-colored crystals melting at 69° C.

3,5-Dibromo-1-(1-ethoxyethyl)-1H-pyrazole-4-carboxaldehyde

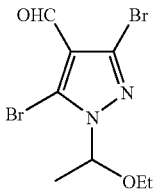

1 g (3.94 mmol) of 3,5-dibromo-1H-pyrazole-4-carboxaldehyde, 1.5 mL (16 mmol) of ethyl vinyl ether and 3 drops of concentrated 12 N hydrochloric acid are introduced with stirring into 30 mL of toluene at a temperature in the region of 20° C. The reaction mixture is stirred for 15 hours at a temperature in the region of 20° C., followed by addition of 1.5 mL (16 mmol) of ethyl vinyl ether, and stirring is continued for 15 hours at a temperature in the region of 20° C. The reaction mixture is then diluted with 20 mL of toluene and washed with twice 30 mL of saturated sodium hydrogen carbonate solution. The organic phase is dried over magnesium sulfate and concentrated to dryness under reduced pressure (2.7 kPa) to give 1.19 g of 3,5-dibromo-1-(1-ethoxyethyl)-1H-pyrazole-4-carboxaldehyde in the form of a yellow oil. $^1$H NMR spectrum (300 MHz, $(CD_3)_2SO$-$d_6$, δ in ppm): 1.10 (t, J=7.5 Hz: 3H); 1.64 (d, J=6.5 Hz: 3H); 3.31 (mt: 1H); 3.51 (mt: 1H); 5.88 (q, J=6.5 Hz: 1H); 9.73 (s: 1H).

3,5-Dibromo-1H-pyrazole-4-carboxaldehyde

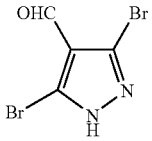

81.7 g (0.268 mol) of 3,4,5-tribromopyrazole are introduced with stirring into 1500 mL of diethyl ether at a temperature in the region of 20° C. and under an argon atmosphere. The mixture is cooled to a temperature in the region of −78° C., followed by dropwise addition of 335 mL (0.536 mol) of a 1.6 M solution of n-butyllithium in hexane over 3 hours 15 minutes. The reaction mixture is stirred for 1.5 hours at a temperature in the region of −75° C., followed by dropwise addition of 100 mL (1.34 mol) of dimethylformamide, while keeping the temperature below −70° C. The mixture is stirred for a further 2 hours at a temperature in the region of −75° C., and then for 15 hours at a temperature in the region of 20° C. The reaction medium is then cooled in an ice-water bath and 1000 mL of water are added. After separation of the phases by settling, the aqueous phase is extracted with 500 mL of diethyl ether and with three times 500 mL of ethyl acetate. The aqueous phase is then acidified with citric acid solution to pH 3 (formation of a precipitate is observed) and extracted with twice 1000 mL of diethyl ether. The organic phase is dried over magnesium sulfate and concentrated to dryness under reduced pressure (2.7 kPa), and the yellow solid obtained is taken up in 300 mL of water and stirred for 2 hours at a temperature in the region of 20° C. The mixture is then filtered and the solid is washed with twice 50 mL of water, dried in a fume cupboard and then dried under reduced pressure (2.7 kPa) at a temperature in the region of 40° C. 51.3 g of 3,5-dibromo-1H-pyrazole-4-carboxaldehyde are thus obtained in the form of a yellow powder melting at 173° C.

EXAMPLE 2

Preparation of 5-(N'-methyl-N'-phenylhydrazinocarbonyl)-1H-thieno[2,3-c]pyrazol-3-yl]-4-methoxybenzamide

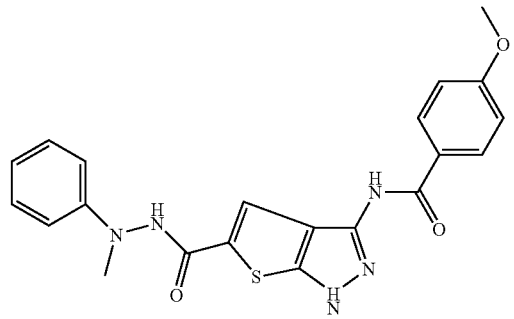

5-(N'-Methyl-N'-phenylhydrazinocarbonyl)-1H-thieno[2,3-c]pyrazol-3-yl]-4-methoxybenzamide is prepared according to example 1. Yield=36%; $^1$H NMR (300 MHz, $(CD_3)_2SO$-$d_6$, δ in ppm): 3.17 (s, 3H); 3.85 (s, 3H); 6.77 (broad t, J=7.5 Hz, 1H); 6.82 (broad d, J=8.5 Hz, 2H); 7.07 (broad d, J=8.0 Hz, 2H); 7.22 (broad t, J=8.0 Hz, 2H); 8.07 (broad d, J=8.5 Hz, 2H); 8.17 (broad s, 1H); 10.75 (broad m, 1H); 11.0 (broad multiplet, 1H); 12.9 (broad multiplet, 1H). LC/MS m=421. EI m/z=421 M$^+$, m/z=300 (M−$C_8H_7O_2$)$^+$, m/z=135 $C_8H_7O_2^+$

EXAMPLE 3

Preparation of N-[5-(N'-cyclohexylhydrazinocarbonyl)-1H-thieno-[2,3-c]pyrazol-3-yl]-4-methoxybenzamide

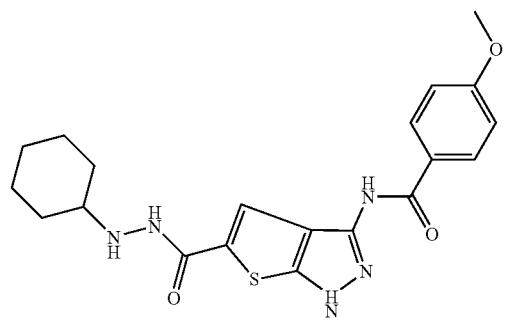

N-[5-(N'-Cyclohexylhydrazinocarbonyl)-1H-thieno[2,3-c]pyrazol-3-yl]-4-methoxybenzamide is prepared according to example 1. Yield=11%. $^1$H NMR (400 MHz, $(CD_3)_2SO$-$d_6$, δ in ppm): 1.01 to 1.26 (m, 5H); 1.55 (m, 1H); from 1.63 to 1.90 (m, 4H); 2.73 (m, 1H); 3.85 (s, 3H); 4.84 (m, 1H); 7.06 (broad d, J=8.5 Hz, 2H); 8.02 (broad s, 1H); 8.07 (broad d, J=8.5 Hz, 2H); 10.05 (broad s, 1H); 10.9 (broad s, 1H); 12.85 (broad s, 1H). LC/MS: m=413; ES m/z=414 MH+

EXAMPLE 4

Preparation of N-[5-(N'-benzyl-N'-phenylhydrazinocarbonyl)-1H-thieno[2,3-c]pyrazol-3-yl]-4-methoxybenzamide

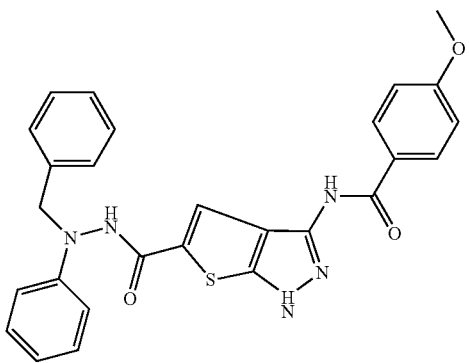

N-[5-(N'-Benzyl-N'-phenylhydrazinocarbonyl)-1H-thieno[2,3-c]pyrazol-3-yl]-4-methoxybenzamide is prepared according to example 1. Yield=7%. MS: ES m/z=498 MH+. $^1$H NMR (400 MHz, (CD$_3$)$_2$SO-d$_6$, δ in ppm): 3.85 (s, 3H); 4.75 (broad s, 2H); 6.75 (broad t, J=7.5 Hz, 1H); 6.92 (broad d, J=8.5 Hz, 2H); 7.07 (broad d, J=8.5 Hz, 2H); from 7.15 to 7.28 (m, 3H); 7.34 (broad t, J=7.5 Hz, 2H); 7.49 (broad d, J=7.5 Hz, 2H); 8.07 (broad d, J=8.5 Hz, 2H); 8.17 (broad s, 1H); 10.85 (broad s, 1H); 11.05 (broad multiplet, 1H); from 12.75 to 13.1 (very broad m, 1H). LC/MS: m=497; ES m/z=498 MH+

EXAMPLE 5

Preparation of N-{5-[N'-(2-ethylphenyl)hydrazinocarbonyl]-1H-thieno[2,3-c]pyrazol-3-yl}-4-methoxybenzamide

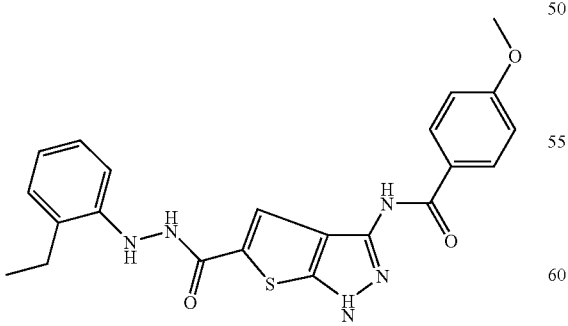

N-{5-[N'-(2-Ethylphenyl)hydrazinocarbonyl]-1H-thieno[2,3-c]pyrazol-3-yl}-4-methoxybenzamide is prepared according to example 1. Yield=60%. MS: ES m/z=436 MH+. $^1$H NMR (400 MHz, (CD$_3$)$_2$SO-d$_6$, δ in ppm): 1.19 (t, J=7.5 Hz, 3H); 2.59 (q, J=7.5 Hz, 2H); 3.85 (s, 3H); from 6.68 to 6.77 (m, 2H); from 6.98 to 7.11 (m, 4H); 7.26 (broad s, 1H); 8.08 (broad d, J=8.5 Hz, 2H); 8.19 (broad s, 1H); 10.5 (broad multiplet, 1H); from 10.7 to 11.3 (very broad m, 1H); from 12.5 to 13.2 (very broad m, 1H). LC/MS: m=435. ES m/z=436 MH+

EXAMPLE 6

Preparation of N-{5-[N'-(2-fluorophenyl)hydrazinocarbonyl]-1H-thieno[2,3-c]pyrazol-3-yl}-4-methoxybenzamide

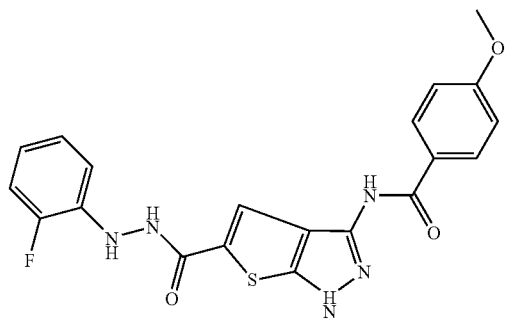

N-{5-[N'-(2-Fluorophenyl)hydrazinocarbonyl]-1H-thieno[2,3-c]pyrazol-3-yl}-4-methoxybenzamide is prepared according to example 1. Yield=65%. $^1$H NMR (400 MHz, (CD$_3$)$_2$SO-d$_6$, δ in ppm): 3.85 (s, 3H); 6.73 (m, 1H); 6.82 (broad t, J=8.0 Hz, 1H); from 6.96 to 7.13 (m, 4H); 7.78 (broad s, 1H); 8.09 (broad d, J=8.5 Hz, 2H); 8.21 (broad s, 1H); 10.5 (broad s, 1H); 11.0 (broad s, 1H); 12.9 (broad s, 1H). LC/MS: m=425. CI m/z=426 MH+

EXAMPLE 7

Preparation of 4-methoxy-N-[5-(N'-o-tolylhydrazinocarbonyl)-1H-thieno[2,3-c]pyrazol-3-yl]benzamide

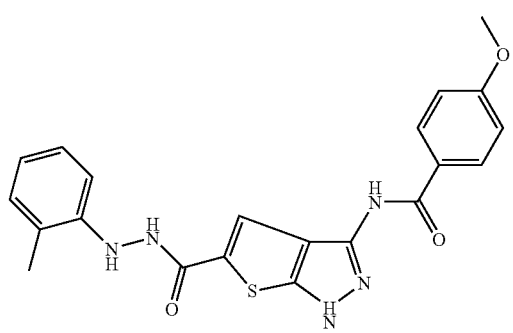

4-Methoxy-N-[5-(N'-o-tolylhydrazinocarbonyl)-1H-thieno[2,3-c]pyrazol-3-yl]-benzamide is prepared according to example 1. Yield=70%. $^1$H NMR (400 MHz, (CD$_3$)$_2$SO-d$_6$, δ in ppm): 2.19 (s, 3H); 3.85 (s, 3H); from 6.63 to 6.74 (m, 2H); 7.02 (broad m, 2H); 7.08 (broad d, J=8.5 Hz, 2H); 7.25 (broad s, 1H); 8.08 (broad d, J=8.5 Hz, 2H); 8.19 (broad s, 1H); 10.5 (broad multiplet, 1H); from 10.7 to 11.5 (very broad m, 1H); from 12.3 to 13.3 (very broad m, 1H). LC/MS: m=421. ES m/z=422 MH$^+$

EXAMPLE 8

Preparation of N-[5-(N'-methyl-N'-phenylhydrazinocarbonyl)-1H-thieno[2,3-c]pyrazol-3-yl]-4-morpholin-4-ylmethylbenzamide

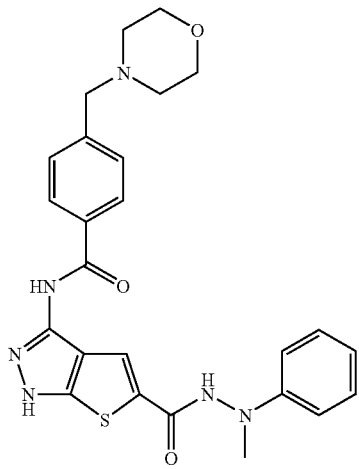

21 mg (154 μmol) of potassium carbonate are added to a solution of 0.09 g (154 μmol) of tert-butyl 5-(N'-methyl-N'-phenylhydrazinocarbonyl)-3-(4-morpholin-4-ylmethylbenzoylamino)thieno[2,3-c]pyrazole-1-carboxylate in 5 mL of methanol in a microwave oven tube. The tube is stoppered and the reaction mixture is irradiated at a temperature in the region of 180° C. for 3 minutes. The reaction mixture is then concentrated to dryness under vacuum (0.6 kPa) at a temperature in the region of 30° C. The residue is purified by chromatography on a cartridge of 25 g of silica gel (0.015-0.040 mm), eluting with a dichloromethane/methanol mixture (99/1 by volume, then 98/2 and finally 97/3) at a flow rate of 10 mL/min. The fractions containing the expected product are combined and then concentrated to dryness under reduced pressure (1.0 kPa) at a temperature in the region of 30° C. The residue is taken up in 10 mL of diisopropyl ether, triturated and then reconcentrated to dryness. The solid obtained is dried in an oven under vacuum (0.01 kPa) at a temperature in the region of 60° C. 40 mg of N-[5-(N'-methyl-N'-phenylhydrazinocarbonyl)-1H-thieno[2,3-c]pyrazol-3-yl]-4-morpholin-4-ylmethylbenzamide are thus obtained in the form of an off-white solid melting at 242° C. MS-EI: 490(+)=M(+).

tert-Butyl 5-(N'-methyl-N'-phenylhydrazinocarbonyl)-3-(4-morpholin-4-ylmethylbenzoylamino)thieno[2,3-c]pyrazole-1-carboxylate

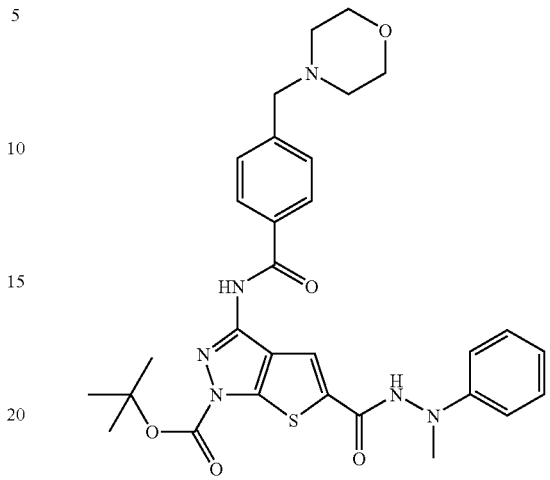

193 mg (1.39 mmol) of potassium carbonate, followed by 240 mg (0.87 mmol) of 4-morpholin-4-ylmethylbenzoyl chloride hydrochloride, are added to a solution of 0.27 g (0.70 mmol) of tert-butyl 3-amino-5-(N'-methyl-N'-phenylhydrazinocarbonyl)-thieno[2,3-c]pyrazole-1-carboxylate in 20 mL of tetrahydrofuran under argon. The reaction mixture is stirred at a temperature in the region of 25° C. for 2 hours, and then refluxed for 4 hours. The reaction mixture is then cooled to a temperature in the region of 25° C., and then treated with 40 mL of ice-cold water. The mixture is extracted successively with 60 mL, and then with twice 40 mL of ethyl acetate. The organic phases are combined, washed twice with 40 mL of saturated brine, dried over magnesium sulfate, filtered and then concentrated to dryness under vacuum (2 kPa) at a temperature in the region of 40° C. The residue is purified by chromatography on a cartridge of 25 g of silica gel (0.015-0.040 mm), eluting successively with pure dichloromethane, and then with dichloromethane/methanol mixtures (99/1 by volume, and then 98.5/1.5, 98/2 and finally 97/3) at a flow rate of 10 mL/min. The fractions containing the expected product are combined and then concentrated to dryness under reduced pressure (0.6 kPa) at a temperature in the region of 30° C. 0.1 g of N-[5-(N'-methyl-N'-phenylhydrazinocarbonyl)-1H-thieno[2,3-c]pyrazol-3-yl]-4-morpholin-4-ylmethylbenzamide is thus obtained in the form of an off-white solid melting at 190° C.

4-Morpholin-4-ylmethylbenzoyl chloride hydrochloride may be prepared according to patents U.S. Pat. No. 4,623,486 A (1986) and WO 90/08128 A1.

tert-Butyl 3-amino-5-(N'-methyl-N'-phenylhydrazinocarbonyl)thieno[2,3-c]-pyrazole-1-carboxylate

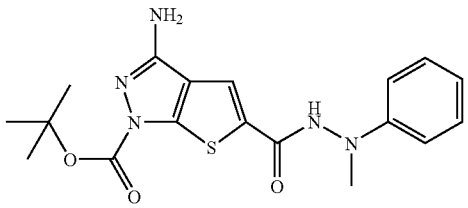

0.58 mL (4.14 mmol) of triethylamine is added to a suspension of 1.19 g (4.14 mmol) of N'-methyl-N'-phenyl(3- amino-1H-thieno[2,3-c]pyrazole)-5-carbohydrazide in 35 mL of dichloromethane under argon. The reaction mixture is stirred at a temperature in the region of 25° C. for 15 minutes, and then 61 mg (0.50 mmol) of 4-dimethylaminopyridine are added. The reaction mixture is then cooled to a temperature in the region of 0° C., and a solution of 0.90 g (4.14 mmol) of di-tert-butyl dicarbonate in 15 mL of dichloromethane is added dropwise. The reaction mixture is then stirred at a temperature in the region of 0° C. for one hour, and then at a temperature in the region of 25° C. for 3 hours. It is then treated with 50 mL of water and stirred at a temperature in the region of 25° C., and the phases are then separated by settling. The aqueous phase is extracted twice with 30 mL of dichloromethane. The organic phases are combined, washed with water to neutral pH (twice 50 mL), dried over magnesium sulfate, filtered and then concentrated to dryness under vacuum (2 kPa) at a temperature in the region of 30° C. The residue is purified by chromatography on a cartridge of 70 g of silica gel (0.015-0.040 mm), eluting with a dichloromethane/methanol mixture (98/2 by volume), at a flow rate of 20 mL/min. The fractions containing the expected product are combined and then concentrated to dryness under reduced pressure (2 kPa) at a temperature in the region of 30° C. 0.38 g of tert-butyl 3-amino-5-(N'-methyl-N'-phenylhydrazinocarbonyl)thieno[2,3-c]pyrazole-1-carboxylate is thus obtained in the form of a beige-colored solid melting at 195° C.

N'-Methyl-N'-phenyl(3-amino-1H-thieno[2,3-c]pyrazole)-5-carbohydrazide

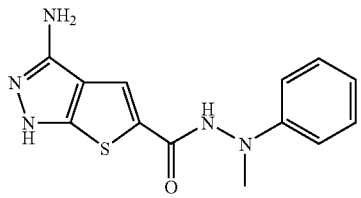

17.3 mL (34.5 mmol) of a 2 M solution of trimethylaluminum in toluene are added dropwise to a solution of 3.9 mL (32.0 mmol) of 1-methyl-1-phenylhydrazine in 180 mL of toluene at a temperature in the region of 25° C. and under argon, while keeping the temperature below or equal to 25° C. The reaction mixture is stirred at a temperature in the region of 25° C. for one hour, and then 2.7 g (11.8 mmol) of ethyl 3-amino-1H-thieno[2,3-c]pyrazole)-5-carboxylate are added by spatula. The reaction mixture is refluxed for 16 hours, and then cooled to a temperature in the region of 25° C. and treated with 200 mL of 10% citric acid solution. The mixture is stirred at a temperature in the region of 25° C. for 30 minutes, and then 200 mL of ethyl acetate are added and the phases of the mixture are separated by settling. The aqueous phase is extracted twice with 150 mL of ethyl acetate. The organic extracts are combined, washed with water to a pH in the region of 6, dried over magnesium sulfate, filtered and then concentrated to dryness under vacuum (2 kPa) at a temperature in the region of 30° C. The residue is purified by chromatography on a column of 200 g of silica gel (0.020-0.040 mm) preneutralized by eluting with a mixture of dichloromethane and triethylamine (1 void volume), followed by eluting with pure dichloromethane (4 void volumes). The products are eluted successively with dichloromethane/methanol mixtures (95/5 and then 90/10 by volume). The fractions containing the expected product are combined and then concentrated to dryness under reduced pressure (2 kPa) at a temperature in the region of 40° C. The residue is taken up in 40 mL of diisopropyl ether, triturated and then filtered on a sinter funnel. The solid obtained is dried under vacuum. 1.5 g of N'-methyl-N'-phenyl(3-amino-1H-thieno[2,3-c]pyrazole)-5-carbohydrazide are thus obtained in the form of a beige-colored powder melting at 186° C.

Ethyl 3-amino-1H-thieno[2,3-c]pyrazole)-5-carboxylate

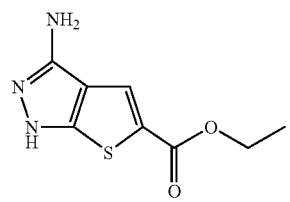

A suspension of 16.4 g (0.063 mol) of ethyl 4-cyano-5-methylsulfonylthiophene-2-carboxylate in 160 mL of absolute ethanol is refluxed until the product has dissolved, and a solution of 6.2 mL (0.126 mol) of hydrazine hydrate in 40 mL of absolute ethanol is then added dropwise. The reaction mixture is stirred at reflux for 2 hours, and 4.6 mL (0.094 mol) of hydrazine hydrate are then added dropwise and stirring at reflux is continued for two hours. After cooling to a temperature in the region of 25° C., the mixture is concentrated to dryness under vacuum (2 kPa) at a temperature in the region of 40° C. The residue is taken up in 200 mL of ethanol and a solution of 13.2 mL (0.158 mol) of 12 N hydrochloric acid is added with stirring at a temperature in the region of 25° C. The reaction mixture is stirred at a temperature in the region of 25° C. for 4 hours, and then poured slowly into 500 mL of saturated sodium hydrogen carbonate solution precooled to 10° C. After stirring for 30 minutes, the mixture is extracted three times with 600 mL of ethyl acetate. The organic extracts are combined, washed twice with 300 mL of saturated brine, dried over magnesium sulfate, filtered and concentrated to dryness under vacuum (2 kPa) at a temperature in the region of 40° C. The residue is purified by chromatography on a column of 500 g of silica gel (0.020-0.045 mm), eluting with pure ethyl acetate. The fractions containing the expected product are combined and then concentrated to dryness under reduced pressure (2 kPa) at a temperature in the region of 40° C. 3.4 g of ethyl 3-amino-1H-thieno[2,3-c]pyrazole)-5-carboxylate are thus obtained in the form of a brown-colored powder, which product is used directly in the following step. MS-EI: 211 (+)=M(+).

Ethyl 4-cyano-5-methylsulfonylthiophene-2-carboxylate

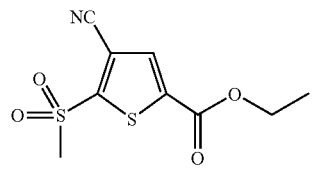

A solution of 92.3 g (0.374 mol) of 3-chloroperoxybenzoic acid in 1 L of dichloromethane maintained at a temperature in the region of −5° C. is added dropwise over 2 hours to a solution of 42.5 g (0.187 mol) of ethyl 4-cyano-5-methylsulfanylthiophene-2-carboxylate in 500 mL of dichloromethane, while maintaining a temperature in the region of −5° C. The reaction mixture is stirred at a temperature in the region of −5° C. for one hour, and then stirred a temperature in the region of 25° C. for 18 hours. It is then cooled in an ice bath and treated with 750 mL of saturated sodium hydrogen carbonate solution and 250 mL of dichloromethane. After stirring for 30 minutes, the mixture is filtered on a sinter funnel and the solid is washed twice with 100 mL of dichloromethane. After separation of the phases of the filtrate by settling, the aqueous phase is extracted with 500 mL of dichloromethane. The organic extracts are combined, washed twice with 1 L of saturated brine, dried over sodium sulfate, filtered and then concentrated to dryness under vacuum (1.5 kPa) at a temperature in the region of 45° C. The residue is recrystallized from 200 mL of ethanol. The precipitate is filtered on a sinter funnel, washed with 100 mL of ethanol, suction-filtered and then dried in a desiccator under vacuum (2 kPa). 37 g of ethyl 4-cyano-5-methylsulfonylthiophene-2-carboxylate are thus obtained in the form of a pale yellow crystalline powder melting at 110° C.

Ethyl 4-cyano-5-methylsulfanylthiophene-2-carboxylate

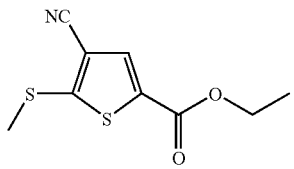

A solution of 50 g (0.21 mol) of ethyl 3-amino-4-cyano-5-methylsulfanylthiophene-2-carboxylate in 500 mL of dimethylformamide under an argon atmosphere is heated to a temperature in the region of 60° C., and a solution of 71.1 mL (0.45 mol) of isopentyl nitrite in 100 mL of dimethylformamide is then introduced with stirring, while maintaining the temperature between 65 and 70° C. The reaction mixture is then stirred at a temperature in the region of 60° C. for 2.5 hours, and then cooled to a temperature in the region of 25° C. and stirred for one hour. The mixture is then treated with 1 L of ice-cold water and then stirred at a temperature in the region of 0° C. for one hour. The precipitate obtained is filtered off and then washed successively three times with 200 mL of water and three times with 200 mL of petroleum ether. 40.5 g (86%) of ethyl 4-cyano-5-methylsulfanylthiophene-2-carboxylate are thus obtained, after drying under reduced pressure, in the form of a yellow crystalline powder melting at 100° C. MS-CI (NH$_3$): 245(+)=(M+NH$_4$)(+).

Ethyl 3-amino-4-cyano-5-methylsulfanylthiophene-2-carboxylate

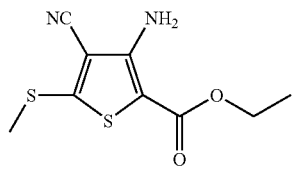

Ethyl 3-amino-4-cyano-5-methylsulfanylthiophene-2-carboxylate may be prepared by adaptation of the method described in Synthesis 2003, 735, starting with 89.5 g of 2-[bis(methylsulfanyl)methylene]malononitrile and replacing the potassium carbonate with triethylamine. 120.5 g (95%) of crude ethyl 3-amino-4-cyano-5-methylsulfanylthiophene-2-carboxylate are obtained after drying, in the form of a pink powder melting at 149° C.

2-[Bis(methylsulfanyl)methylene]malononitrile

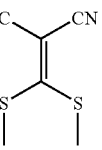

2-[Bis(methylsulfanyl)methylene]malononitrile may be prepared according to *J. Med. Chem.* 2003. 46. 1229 or alternatively according to *Synth. Commun.* 2003. 33. 3989.

EXAMPLE 9

Preparation of 4-bromo-N-[5-(N'-methyl-N'-phenylhydrazinocarbonyl)-1H-thieno[2,3-c]pyrazol-3-yl]benzamide

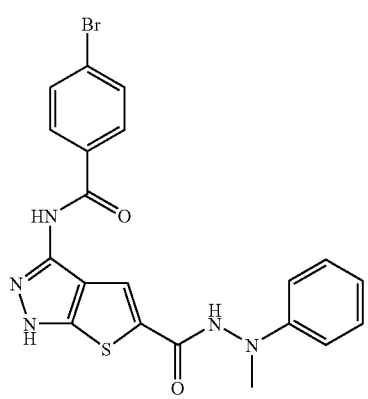

14.5 mg (105 μmol) of potassium carbonate are added to a solution of 0.04 g (70 μmol) of tert-butyl 3-(4-bromobenzoylamino)-5-(N'-methyl-N'-phenylhydrazinocarbonyl)thieno[2,3-c]pyrazole-1-carboxylate in 3 mL of methanol in a microwave oven tube. The tube is stoppered and the reaction mixture is irradiated at a temperature in the region of 180° C. for 3 minutes. The reaction mixture is then concentrated to dryness under vacuum (2 kPa) at a temperature in the region of 35° C. The residue is taken up in dichloromethane, and then in a mixture of 1 mL of methanol, 4 mL of water and 10 mL of ethyl acetate. After separation of the phases by settling, the organic phase is washed twice with 3 mL of water, dried over magnesium sulfate, filtered and then concentrated to dryness under vacuum (2 kPa) at a temperature in the region of 35° C. The residue is taken up in diisopropyl ether, filtered on a sinter funnel, suction-filtered and then dried in an oven under vacuum (0.01 kPa) at a temperature in the region of 40° C. The residue is purified by chromatography on a column of 15 g of silica gel (0.015-0.040 mm), eluting with a dichloromethane/methanol mixture (99/1 by volume, then 98/2 and finally 97/3) at a flow rate of 20 mL/min. The fractions containing the expected product are combined and then concentrated to dryness under reduced pressure (2 kPa) at a temperature in the region of 35° C. 18 mg of 4-bromo-N-[5-(N'-methyl-N'-phenylhydrazinocarbonyl)-1H-thieno[2,3-c]pyrazol-3-yl]benzamide are thus obtained in the form of a pale yellow solid melting at 172° C. LC-MS-DAD-ELSD: 468(−)/ ... =(M−H)(−)/ ... ; 470(+)/ ... =(M+H)(+)/ ... (1 Br present).

tert-Butyl 3-(4-bromobenzoylamino)-5-(N'-methyl-N'-phenylhydrazinocarbonyl)thieno[2,3-c]pyrazole-1-carboxylate

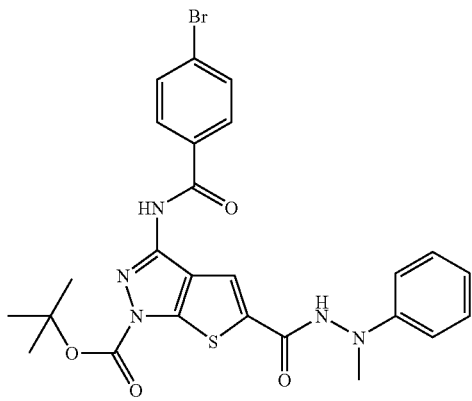

169 mg (1.22 mmol) of potassium carbonate, followed by 191 mg (0.87 mmol) of 4-bromobenzoyl chloride, are added to a solution of 0.27 g (0.70 mmol) of tert-butyl 3-amino-5-(N'-methyl-N'-phenylhydrazinocarbonyl)thieno[2,3-c]pyrazole-1-carboxylate in 20 mL of tetrahydrofuran under argon. The reaction mixture is stirred at reflux for 2 hours. The reaction mixture is then cooled to a temperature in the region of 25° C. and treated with 40 mL of ice-cold water. The mixture is extracted successively with 60 mL and then with twice 40 mL of ethyl acetate. The organic phases are combined, washed twice with 40 mL of saturated brine, dried over magnesium sulfate, filtered and then concentrated to dryness under vacuum (2 kPa) at a temperature in the region of 35° C. The residue is purified by chromatography on a cartridge of 25 g of silica gel (0.015-0.040 mm), eluting successively with dichloromethane/methanol mixtures (99/1 by volume, and then 98/2) at a flow rate of 13 mL/min. The fractions containing the expected product are combined and then concentrated to dryness under reduced pressure (2 kPa) at a temperature in the region of 35° C. 0.04 g of tert-butyl 3-(4-bromobenzoylamino)-5-(N'-methyl-N'-phenylhydrazinocarbonyl)thieno[2,3-c]pyrazole-1-carboxylate is thus obtained in the form of a white solid melting at 192° C.

tert-Butyl 3-amino-5-(N'-methyl-N'-phenylhydrazinocarbonyl)thieno[2,3-c]pyrazole-1-carboxylate is described in example 8.

EXAMPLE 10

Preparation of N-[5-(N'-methyl-N'-phenylhydrazinocarbonyl)-1H-thieno[2,3-c]pyrazol-3-yl]-4-(4-methylpiperazin-1-ylmethyl)benzamide

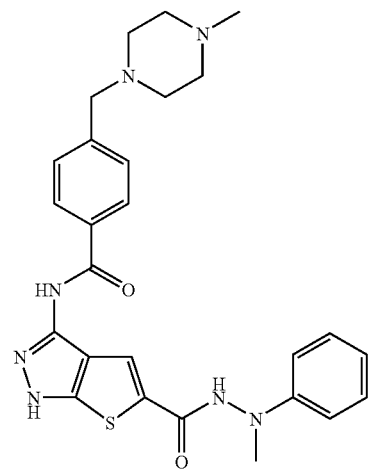

A solution of 0.14 g (232 µmol) of tert-butyl 5-(N'-methyl-N'-phenylhydrazinocarbonyl)-3-[4-(4-methylpiperazin-1-ylmethyl)benzoylamino]-thieno[2,3-c]pyrazole-1-carboxylate in 8 mL of methanol is introduced into a microwave oven tube. The tube is stoppered and the reaction mixture is irradiated at a temperature in the region of 100° C. for 20 minutes, and then for two further periods of 15 minutes. The reaction mixture is then concentrated to dryness under vacuum (2 kPa) at a temperature in the region of 35° C. The residue is taken up in 15 mL of diisopropyl ether, triturated, filtered on a sinter funnel, washed twice with 5 mL of diisopropyl ether, suction-filtered and then dried in an oven under vacuum (0.01 kPa) at a temperature in the region of 60° C. 78 mg of N-[5-(N'-methyl-N'-phenylhydrazinocarbonyl)-1H-thieno[2,3-c]pyrazol-3-yl]-4-(4-methylpiperazin-1-ylmethyl)benzamide are thus obtained in the form of an off-white solid melting at 246° C. LC-MS-DAD-ELSD: 504(+)=(M+H)(+); 502(−)=(M−H)(−).

tert-Butyl 5-(N'-methyl-N'-phenylhydrazinocarbonyl)-3-[4-(4-methylpiperazin-1-ylmethyl)benzoylamino]thieno[2,3-c]pyrazole-1-carboxylate

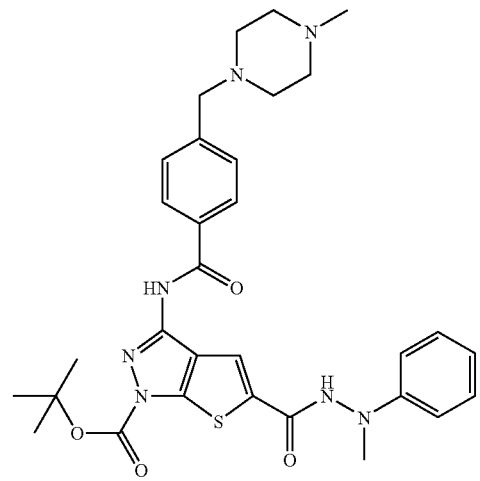

391 mg (1.55 mmol) of 4-(4-methylpiperazin-1-ylmethyl) benzoyl chloride hydrochloride are added to a solution of 0.30 g (0.77 mmol) of tert-butyl 3-amino-5-(N'-methyl-N'-phenylhydrazinocarbonyl)thieno[2,3-c]pyrazole-1-carboxylate in 16 mL of pyridine under argon. The reaction mixture is stirred at a temperature in the region of 25° C. for 16 hours, a further 294 mg (1.16 mmol) of 4-(4-methylpiperazin-1-ylmethyl)benzoyl chloride are then added and stirring is continued for 5 hours. The reaction mixture is then cooled to a temperature in the region of 10° C. and then treated with 50 mL of water. The mixture is extracted twice with 100 mL of ethyl acetate. The organic phases are combined, washed with water to neutral pH, dried over magnesium sulfate, filtered and then concentrated to dryness under vacuum (3 kPa) at a temperature in the region of 30° C. The residue is purified by chromatography on a cartridge of 25 g of silica gel (0.015-0.040 mm), eluting successively with dichloromethane/methanol mixtures (98/2 by volume, and then 97/3, then 96/4 and finally 95/5) at a flow rate of 15 mL/min. The fractions containing the expected product are combined and then concentrated to dryness under reduced pressure (3 kPa) at a temperature in the region of 30° C. 0.14 g of tert-butyl 5-(N'-methyl-N'-phenylhydrazinocarbonyl)-3-[4-(4-methylpiperazin-1-ylmethyl)benzoylamino]thieno[2,3-c]pyrazole-1-carboxylate is thus obtained in the form of an off-white solid melting at 218° C. tert-Butyl 3-amino-5-(N'-methyl-N'-phenylhydrazinocarbonyl)thieno[2,3-c]pyrazole-1-carboxylate is described in example 8. 4-(4-Methylpiperazin-1-ylmethyl)benzoyl chloride may be prepared according to patent WO 03/066 613 A1.

EXAMPLES 11a AND 11b

Preparation of 4-(3,5-dimethylpiperazin-1-ylmethyl)-N-[5-(N'-methyl-N'-phenylhydrazinocarbonyl)-1H-thieno[2,3-c]pyrazol-3-yl]benzamide and 4-(3,5-dimethylpiperazin-1-ylmethyl)-N-[5-(N'-(4-chlorophenyl)-N'-methylhydrazinocarbonyl)-1H-thieno[2,3-c]pyrazol-3-yl]-benzamide 40 mg (108 µmol) of tetrabutylammonium iodide, followed by 184 mg (1.61 mmol) of cis-2,6-dimethylpiperazine, are added to a solution of 290 mg (0.54 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 6 mL of dimethylformamide under argon. The reaction mixture is stirred at a temperature in the region of 25° C. for 3 hours, and then poured into a mixture of ice, ethyl acetate and n-heptane. The mixture is filtered on a sinter funnel, suction-filtered and air-dried. The solid obtained is dissolved in 5 mL of methanol and the solution is introduced into a microwave oven tube. The tube is stoppered and the reaction mixture is irradiated at a temperature in the region of 100° C. for three times 10 minutes. The reaction mixture is then concentrated to dryness under vacuum (2 kPa) at a temperature in the region of 40° C. The residue is purified by preparative LC/MS (condition B'). 130 mg of 4-(3,5-dimethylpiperazin-1-ylmethyl)-N-[5-(N'-methyl-N'-phenylhydrazinocarbonyl)-1H-thieno[2,3-c]pyrazol-3-yl]benzamide are thus obtained in the form of a yellow powder melting between 192 and 202° C. LC-MS-DAD-ELSD: 518(+)=(M+H)(+).

49 mg of 4-(3,5-dimethylpiperazin-1-ylmethyl)-N-[5-(N'-(4-chlorophenyl)-N'-methylhydrazinocarbonyl)-1H-thieno[2,3-c]pyrazol-3-yl]benzamide are isolated in the same manner, in the form of a pale yellow powder melting at 212° C. $^1$H NMR (300 MHz, (CD$_3$)$_2$SO-d$_6$, δ in ppm): This is the salt of the expected structure, with 1.18 (d, J=6.5 Hz, 6H); 2.11 (broad t, J=12.5 Hz, 2H); 3.00 (broad d, J=12.5 Hz, 2H); 3.17 (s, 3H); 3.33 (broad m, 2H); 3.73 (partially masked m, 2H); 6.82 (d, J=9.0 Hz, 2H); 7.25 (d, J=9.0 Hz, 2H); 7.50 (d, J=8.0 Hz, 2H); 8.08 (d, J=8.0 Hz, 2H); 8.16 (s, 1H); 8.20 (partially masked broad multiplet, 2H); 8.92 (broad multiplet, 1H); 10.8 (s, 1H); 11.2 (s, 1H).

tert-Butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate

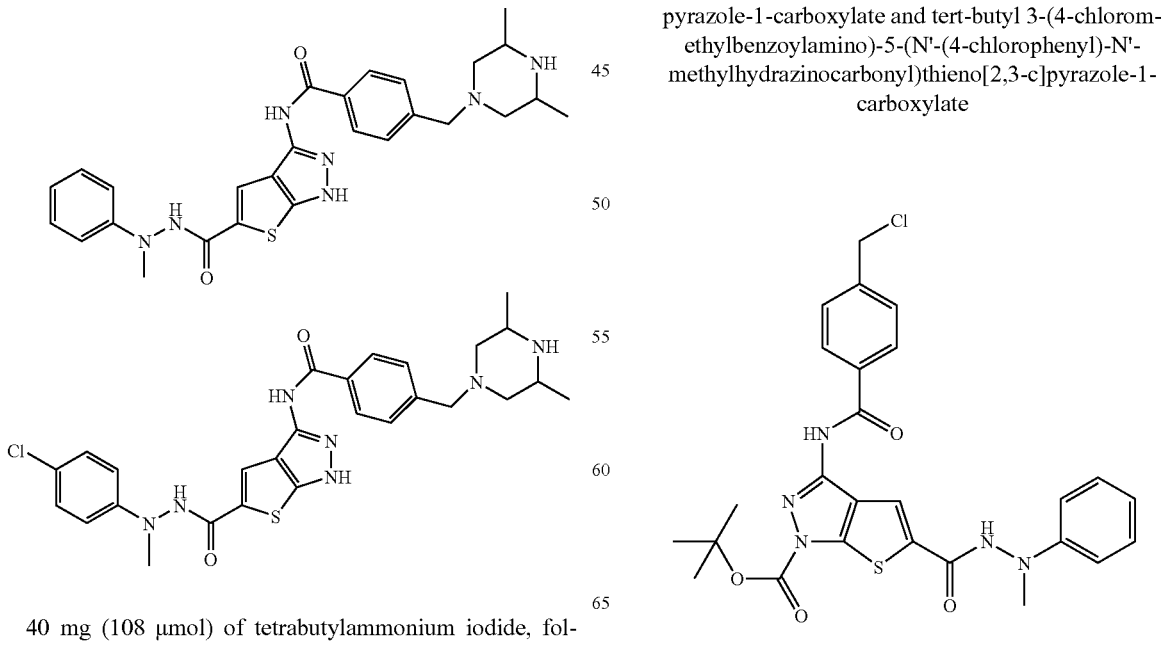

-continued

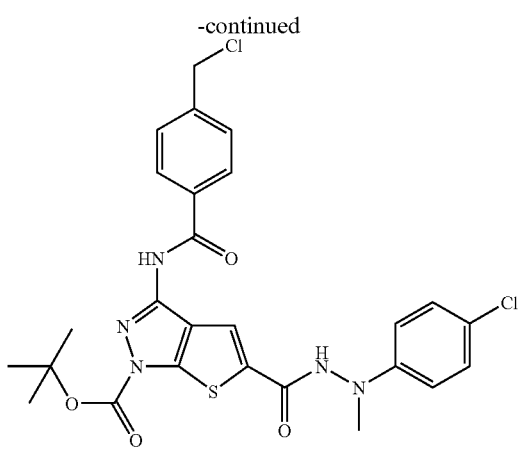

276 mg (2.0 mmol) of potassium carbonate, followed by 2.0 mL (2.0 mmol) of a 1 M solution of 4-(chloromethyl)benzoyl chloride in tetrahydrofuran, are added to a solution of 0.39 g (1.0 mmol) of an approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate in 25 mL of tetrahydrofuran under argon. The reaction mixture is stirred at reflux for 2 hours, and then cooled to a temperature in the region of 25° C. and stirred for 16 hours. It is then poured into ice-cold water and extracted twice with 25 mL of ethyl acetate. The organic phases are combined, washed with saturated brine, dried over magnesium sulfate, filtered and then concentrated to dryness under vacuum (2 kPa) at a temperature in the region of 40° C. The residue is purified by chromatography on a cartridge of 25 g of silica gel (0.015-0.040 mm), eluting with a dichloromethane/methanol mixture (98/2 by volume) at a flow rate of 10 mL/min. The fractions containing the expected product are combined and then concentrated to dryness under reduced pressure (2 kPa) at a temperature in the region of 40° C. The residue is repurified by chromatography on a cartridge of 90 g of silica gel (0.015-0.040 mm), eluting with a dichloromethane/methanol mixture (98/2 by volume) at a flow rate of 10 mL/min. The fractions containing the expected product are combined and then concentrated to dryness under reduced pressure (2 kPa) at a temperature in the region of 40° C. 422 mg of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate are thus obtained in the form of an orange-colored foam. LC-MS-DAD-ELSD and MS-EI-CI: mixture of expected structure (about 70%; MW=539/ . . . ) and expected dichloro analog (about 30%; MW=573/ . . . ). $^1$H NMR (400 MHz, (CD$_3$)$_2$SO-d$_6$, δ in ppm): approximately 80%-20% mixture of conformers, with 1.55 (s, 1.8H); 1.64 (s, 7.2H); 3.18 (s, 2.4H); 3.20 (s, 0.6H); 4.85 (s, 2H); 6.78 (t, J=7.5 Hz, 0.8H); 6.83 (d, J=8.0 Hz, 1.6H); 6.97 (t, J=8.0 Hz, 0.2H); 7.03 (d, J=8.0 Hz, 0.4H); 7.22 (t, J=8.0 Hz, 1.6H); 7.32 (t, J=8.0 Hz, 0.4H); 7.60 (d, J=8.0 Hz, 2H); 8.11 (d, J=8.0 Hz, 2H); 8.27 (s, 0.2H); 8.32 (s, 0.8H); 9.90 (s, 0.2H); 10.95 (s, 0.8H); 11.7 (s, 0.2H); 11.8 (s, 0.8H).

tert-Butyl 3-amino-5-(N'-methyl-N'-phenylhydrazinocarbonyl)thieno[2,3-c]-pyrazole-1-carboxylate and tert-butyl 3-amino-5-(N'-(4-chlorophenyl)-N'-methylhydrazinocarbonyl)thieno[2,3-c]pyrazole-1-carboxylate

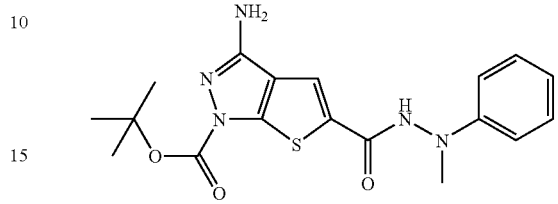

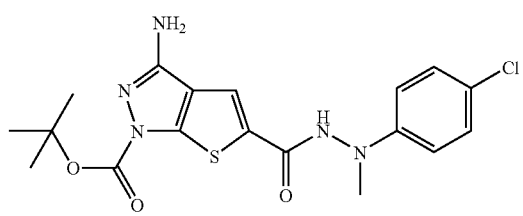

1.19 g (9.74 mmol) of 4-(dimethylamino)pyridine and then 7.4 mL (53.6 mmol) of triethylamine are added to a suspension of 14 g (48.7 mmol) of a mixture of N'-methyl-N'-phenyl (3-amino-1H-thieno[2,3-c]pyrazole)-5-carbohydrazide (major) and tert-butyl 3-amino-5-(N'-(4-chlorophenyl)-N'-methylhydrazinocarbonyl)thieno[2,3-c]pyrazole-1-carboxylate (minor) in 500 mL of dichloromethane under argon. The reaction mixture is then cooled to a temperature in the region of 0° C., and a solution of 8.5 g (39.0 mmol) of di-tert-butyl dicarbonate in 200 mL of dichloromethane is then added dropwise over one hour. The reaction mixture is then stirred at a temperature in the region of 0° C. for one hour, and then heated to a temperature in the region of 25° C. and concentrated to dryness under vacuum (2 kPa) at a temperature in the region of 40° C. The residue is purified by chromatography on a column of 500 g of silica gel (0.020-0.040 mm), eluting with pure dichloromethane, and then with a dichloromethane/methanol mixture (99/1 by volume). The fractions containing the expected product are combined and then concentrated to dryness under reduced pressure (2 kPa) at a temperature in the region of 40° C. The residue is repurified by chromatography on a cartridge of 400 g of silica gel (0.020-0.040 mm), eluting with a dichloromethane/tetrahydrofuran mixture (98/2 by volume). The fractions containing the expected product are combined and then concentrated to dryness under reduced pressure (2 kPa) at a temperature in the region of 40° C. 7.0 g of an approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate are thus obtained in the form of a beige-colored solid. LC-MS-DAD-ELSD: mixture containing the expected structure (estimated purity 70%): 388(+)=(M+H)(+).

N'-Methyl-N'-phenyl(3-amino-1H-thieno[2,3-c]pyrazole)-5-carbohydrazide

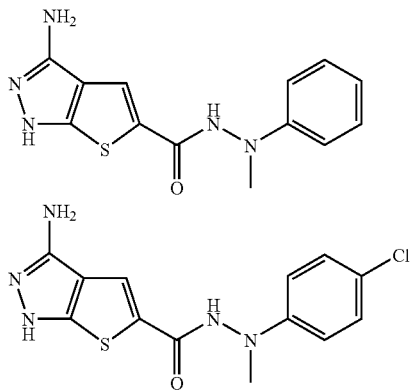

650 mL (650 mmol) of a 1 M solution of hydrazine in tetrahydrofuran are added over 20 minutes to a solution of 29.6 g (45.2 mmol) of a mixture of N'-methyl-N'-phenyl(4-cyano-5-methanesulfinylthiophene)-2-carbohydrazide (major), N'-methyl-N'-phenyl(4-cyano-5-methanesulfonylthiophene)-2-carbohydrazide (minor), N'-(4-chlorophenyl)-N'-methyl(4-cyano-5-methanesulfinylthiophene)-2-carbohydrazide (minor) and N'-(4-chlorophenyl)-N'-methyl(4-cyano-5-methanesulfonylthiophene)-2-carbohydrazide (minor) in 900 mL of ethanol under argon. The reaction mixture is heated at a temperature in the region of 50° C. for 16 hours, and then cooled to a temperature in the region of 25° C. and concentrated to dryness under vacuum (2 kPa) at a temperature in the region of 40° C. The residue is taken up in 1 L of ethanol and a solution of 20 mL (240 mmol) of 12 N hydrochloric acid is added with stirring at a temperature in the region of 25° C. The reaction mixture is stirred at a temperature in the region of 25° C. for 1.75 hours, and 20 mL (240 mmol) of 12 N hydrochloric acid are then added. The reaction mixture is stirred at a temperature in the region of 25° C. for 1.5 hours and then filtered, and the solid is washed twice with 200 mL of ethanol. The filtrate is concentrated to dryness under vacuum (2 kPa) at a temperature in the region of 40° C. The residue is purified by chromatography on a column of 500 g of silica gel (0.020-0.040 mm), eluting with a dichloromethane/methanol mixture (90/10 by volume), and then with a dichloromethane/methanol/28% aqueous ammonia mixture (77/20/3 by volume). The fractions containing the expected product are combined and then concentrated to dryness under reduced pressure (2 kPa) at a temperature in the region of 40° C. The residue is taken up in 200 mL of ethyl acetate and recrystallized. The solid obtained is filtered off, suction-filtered and dried in a desiccator under vacuum. The mother liquors are concentrated to dryness under vacuum (2 kPa) at a temperature in the region of 40° C. The residue is purified by chromatography on a column of silica gel (0.020-0.040 mm), eluting with a dichloromethane/methanol/28% aqueous ammonia mixture (77/20/3 by volume). The fractions containing the expected product are combined and then concentrated to dryness under reduced pressure (2 kPa) at a temperature in the region of 40° C. The residue is taken up in ethyl acetate, triturated and then reconcentrated to dryness under the same conditions. 14 g of N'-methyl-N'-phenyl(3-amino-1H-thieno[2,3-c]pyrazole)-5-carbohydrazide (major) and N'-(4-chlorophenyl)-N'-methyl(3-amino-1H-thieno[2,3-c]pyrazole)-5-carbohydrazide (minor) are thus obtained in total, in the form of a brown foam, which product is used directly in the following step.

N'-Methyl-N'-phenyl(4-cyano-5-methanesulfinylthiophene)-2-carbohydrazide; N'-methyl-N'-phenyl(4-cyano-5-methanesulfonylthiophene)-2-carbohydrazide; N'-(4-chlorophenyl)-N'-methyl(4-cyano-5-methanesulfinylthiophene)-2-carbohydrazide; N'-(4-chlorophenyl)-N'-methyl(4-cyano-5-methanesulfonylthiophene)-2-carbohydrazide

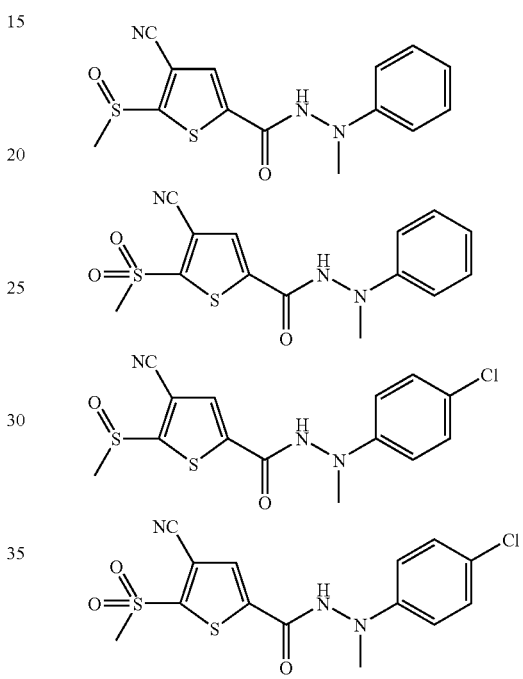

83.3 g (135.5 mmol) of Oxone (potassium peroxymonosulfate) are added over 5 minutes to a solution of 27.4 g (90.3 mmol) of N'-methyl-N'-phenyl(4-cyano-5-methylsulfanylthiophene)-2-carbohydrazide in 1.0 L of tetrahydrofuran under argon, followed by addition of 100 mL of water. The reaction mixture is stirred at a temperature in the region of 25° C. for 2.5 hours, and then filtered through magnesium sulfate. The solid is washed twice with tetrahydrofuran and the filtrate is concentrated to dryness under vacuum (2 kPa) at a temperature in the region of 40° C. The residue is taken up in 500 mL of ethyl acetate, the phases are separated by settling and the aqueous phase is extracted with 500 mL of ethyl acetate. The organic phases are combined, dried over magnesium sulfate, filtered and then concentrated to dryness under vacuum (2 kPa) at a temperature in the region of 40° C. 29.4 g of a mixture of N'-methyl-N'-phenyl(4-cyano-5-methanesulfinylthiophene)-2-carbohydrazide (major), N'-methyl-N'-phenyl(4-cyano-5-methanesulfonylthiophene)-2-carbohydrazide (minor), N'-(4-chlorophenyl)-N'-methyl(4-cyano-5-methanesulfinylthiophene)-2-carbohydrazide (minor) and N'-(4-chlorophenyl)-N'-methyl(4-cyano-5-methanesulfonylthiophene)-2-carbohydrazide (minor) are thus obtained in the form of a brown foam, which product is used directly in the following step. LC/MS: 4 peaks RT=3.11 min. M+H$^+$: 320.06; RT=3.33 min. M+H$^+$: 353.99 (1 Cl); RT=3.53 min. M+H$^+$: 336.04; RT=3.88 min. M+H$^+$: 369.97 (1 Cl).

N'-Methyl-N'-phenyl(4-cyano-5-methylsulfanylthiophene)-2-carbohydrazide

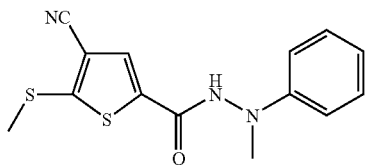

100.3 mL (200.6 mmol) of a 2 M solution of trimethylaluminum in toluene, diluted in 600 mL of toluene, are added to a solution of 24.6 mL (200.6 mmol) of 1-methyl-1-phenylhydrazine in 300 mL of toluene at a temperature in the region of 25° C. and under argon, while keeping the temperature below or equal to 25° C. The reaction mixture is stirred at a temperature in the region of 25° C., and 39.3 g (172.9 mmol) of ethyl 4-cyano-5-methylsulfanylthiophene-2-carboxylate are then added by spatula. The reaction mixture is heated at a temperature in the region of 80° C. for 4 hours, and then cooled to a temperature in the region of 25° C. and stirred for 16 hours. It is then cooled to a temperature in the region of 0° C. and 1 L of 1 N hydrochloric acid is added. The resulting suspension is stirred at a temperature in the region of 10° C. for one hour and then filtered. The precipitate is filtered off by suction, dried in a fume cupboard for 2.5 days, and then dried in a desiccator under vacuum (2 kPa) for 4 hours. The phases of the filtrate are separated by settling and the aqueous phase is extracted with 500 mL of ethyl acetate. The organic phases are combined, washed with 500 mL of saturated brine, dried over magnesium sulfate, filtered and then concentrated to dryness under vacuum (2 kPa) at a temperature in the region of 40° C. 29.1 g of N'-methyl-N'-phenyl(4-cyano-5-methylsulfanylthiophene)-2-carbohydrazide are thus obtained in the form of an ochre-colored powder. MS-EI: 303(+)=M(+).

Ethyl 4-cyano-5-methylsulfanylthiophene-2-carboxylate is described in example 8.

EXAMPLES 12a AND 12b

Preparation of 4-(4-methylperhydro-1,4-diazepin-1-ylmethyl)-N-[5-(N'-methyl-N'-phenylhydrazinocarbonyl)-1H-thieno[2,3-c]-pyrazol-3-yl]benzamide and 4-(4-methylperhydro-1,4-diazepin-1-ylmethyl)-N-[5-(N'-(4-chlorophenyl)-N'-methylhydrazinocarbonyl)-1H-thieno[2,3-c]pyrazol-3-yl]benzamide

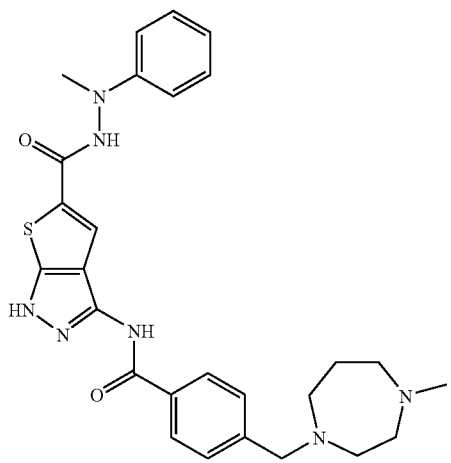

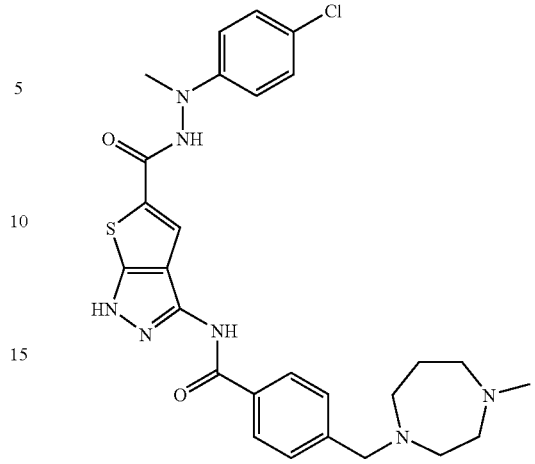

27 mg (74 μmol) of tetrabutylammonium iodide, followed by 138 μL (1.11 mmol) of N-methyl-homopiperazine, are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno [2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 6 mL of dimethylformamide under argon. The reaction mixture is stirred at a temperature in the region of 25° C. for 16 hours, and then treated with ice. It is then extracted with ethyl acetate and twice with dichloromethane. The organic extracts are combined and then concentrated to dryness under vacuum (2 kPa) at a temperature in the region of 40° C. The residue is dissolved in 3 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (1 injection: conditions B'; 3 injections: conditions B). 53 mg of 4-(4-methylperhydro-1,4-diazepin-1-ylmethyl)-N-[5-(N'-methyl-N'-phenylhydrazinocarbonyl)-1H-thieno[2,3-c]pyrazol-3-yl]benzamide are thus obtained in the form of a yellow powder. LC-MS-DAD-ELSD: 516(−)=(M−H)(−); 518(+)=(M+H)(+).

20 mg of 4-(4-methylperhydro-1,4-diazepin-1-ylmethyl)-N-[5-(N'-(4-chlorophenyl)-N'-methylhydrazinocarbonyl)-1H-thieno[2,3-c]pyrazol-3-yl]benzamide are isolated in the same manner, in the form of a pale yellow powder melting at 162° C. $^1$H NMR (300 MHz, $(CD_3)_2SO$-$d_6$, δ in ppm): This is the salt of the expected structure, with 2.08 (broad m, 2H); 2.84 (s, 3H); 3.18 (s, 3H); from 2.93 to 4.51 (partially masked m, 10H); 6.82 (d, J=9.0 Hz, 2H); 7.24 (d, J=9.0 Hz, 2H); 7.63 (broad d, J=8.0 Hz, 2H); 8.14 (d, J=8.0 Hz, 2H); 8.17 (s, 1H); 8.22 (partially masked broad multiplet, 1H); 10.0 (very broad m, 1H); 10.8 (s, 1H); 11.3 (s, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c] pyrazole-1-carboxylate is described in example 11.

EXAMPLES 13a AND 13b

Preparation of N-[5-(N'-methyl-N'-phenylhydrazinocarbonyl)-1H-thieno[2,3-c]pyrazol-3-yl]-4-piperazin-1-ylmethylbenzamide and N-{5-[N'-(4-chlorophenyl)-N'-methylhydrazinocarbonyl]-1H-thieno[2,3-c]pyrazol-3-yl}-4-piperazin-1-ylmethylbenzamide

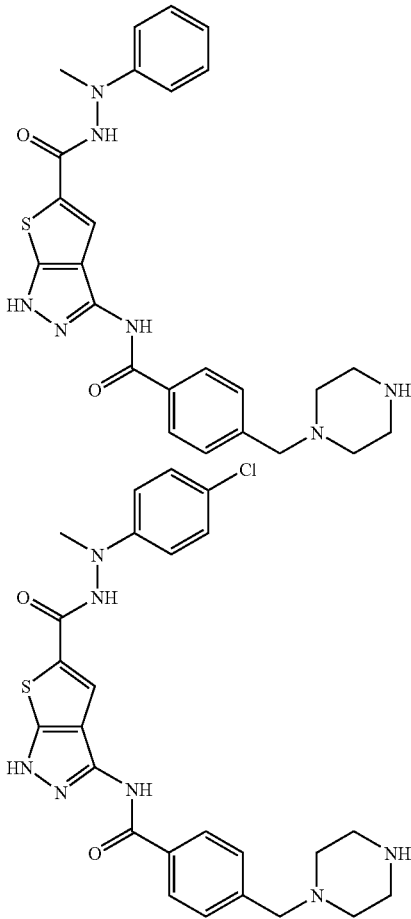

27 mg (74 µmol) of tetrabutylammonium iodide, followed by 96 mg (1.11 mmol) of piperazine, are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then treated with ice. It is then extracted with ethyl acetate and then twice with dichloromethane. The organic extracts are combined and then concentrated to dryness under vacuum (2 kPa) at a temperature in the region of 40° C. The residue is dissolved in 3 mL of methanol and the solution is introduced into a microwave oven tube. The tube is stoppered and the reaction mixture is irradiated at a temperature in the region of 100° C. for twice 30 minutes. The reaction mixture is then concentrated to dryness under vacuum (2 kPa) at a temperature in the region of 40° C. The residue is purified by preparative LC/MS (conditions B). 83 mg of N-[5-(N'-methyl-N'-phenylhydrazinocarbonyl)-1H-thieno[2,3-c]pyrazol-3-yl]-4-piperazin-1-ylmethylbenzamide are thus obtained in the form of a yellow powder melting at 176° C. LC-MS-DAD-ELSD: 490(+)=M(+H)(+).

34 mg of N-{5-[N'-(4-chlorophenyl)-N'-methylhydrazinocarbonyl]-1H-thieno[2,3-c]-pyrazol-3-yl}-4-piperazin-1-ylmethylbenzamide are isolated in the same manner, in the form of an orange-colored powder melting at 180° C. LC-MS-DAD-ELSD: 524(+)/ . . . =(M+H)(+)/ . . . (1 Cl)

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 14a AND 14b

Preparation of N-[5-(N'-methyl-N'-phenylhydrazinocarbonyl)-1H-thieno[2,3-c]pyrazol-3-yl]-4-(3-methylpiperazin-1-ylmethyl)benzamide and N-{5-[N'-(4-chlorophenyl)-N'-methylhydrazinocarbonyl]-1H-thieno[2,3-c]pyrazol-3-yl}-4-(3-methylpiperazin-1-ylmethyl)benzamide

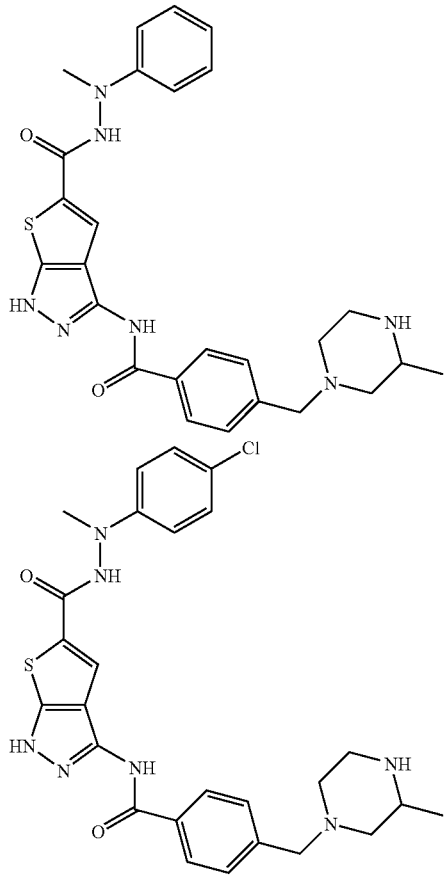

27 mg (74 µmol) of tetrabutylammonium iodide, followed by 111 mg (1.11 mmol) of 2-methylpiperazine, are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1- carboxylate in 6 mL of dimethylformamide under argon. The reaction mixture is stirred at a temperature in the region of 25° C. for 16 hours, and then treated with ice. It is then extracted with ethyl acetate and then twice with dichloromethane. The organic extracts are combined and then concentrated to dryness under vacuum (2 kPa) at a temperature in the region of 40° C. The residue is dissolved in 3 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by chromatography on a cartridge of 12 g of silica gel (0.035-0.060 mm), eluting first with a gradient of a dichloromethane/methanol mixture (100/0 to 98/2 by volume), and then with a dichloromethane/methanol/28% aqueous ammonia mixture (12/3/0.5 by volume) at a flow rate of 20 mL/min. The fractions containing the expected product are combined and then concentrated to dryness under reduced pressure (2 kPa) at a temperature in the region of 40° C. The residue is purified by preparative LC/MS (conditions B). 85 mg of N-[5-(N'-methyl-N'-phenylhydrazinocarbonyl)-1H-thieno[2,3-c]pyrazol-3-yl]-4-(3-methylpiperazin-1-ylmethyl)benzamide are thus obtained in the form of a yellow powder melting from 176 to 186° C. LC-MS-DAD-ELSD: 504(+)=(M+H)(+).

8 mg of N-{5-[N'-(4-chlorophenyl)-N'-methylhydrazinocarbonyl]-1H-thieno[2,3-c]pyrazol-3-yl}-4-(3-methylpiperazin-1-ylmethyl)benzamide are isolated in the same manner, in the form of a pale yellow solid melting from 189 to 195° C. LC-MS-DAD-ELSD: 538(+)/ . . . =(M+H)(+)/ . . . (1 Cl)

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 15a AND 15b

Preparation of 4-diethylaminomethyl-N-[5-(N'-methyl-N'-phenylhydrazinocarbonyl)-1H-thieno[2,3-c]pyrazol-3-yl]benzamide trifluoroacetate and N-{5-[N'-(4-chlorophenyl)-N'-methylhydrazinocarbonyl]-1H-thieno[2,3-c]pyrazol-3-yl}-4-diethylaminomethylbenzamide

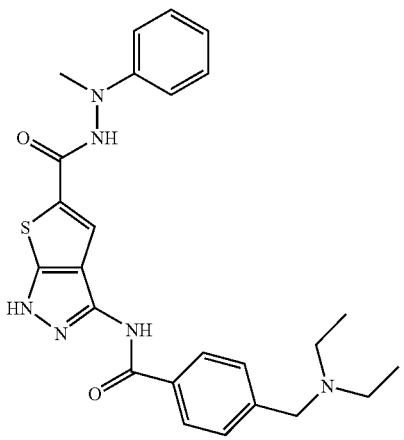

-continued

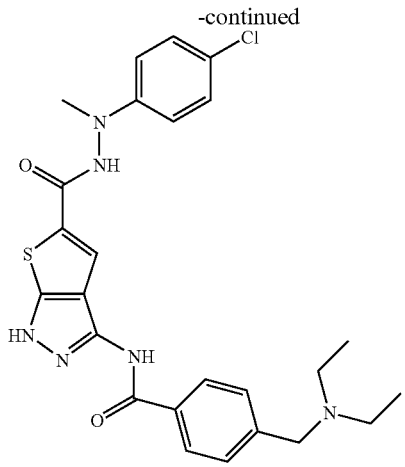

14 mg (37 μmol) of tetrabutylammonium iodide and then a suspension of 61 mg (0.56 mmol) of diethylamine hydrochloride and 77 mg (0.56 mmol) of potassium carbonate in 1.5 mL of dimethylformamide are added to a solution of 100 mg (0.19 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 1.5 mL of dimethylformamide under argon. The reaction mixture is stirred at a temperature in the region of 25° C. for 80 hours, and then treated with ice. It is then extracted twice with a 50/50 mixture (v/v) of ethyl acetate and heptane. The organic extracts are combined, dried over magnesium sulfate and then concentrated to dryness under vacuum (2 kPa) at a temperature in the region of 40° C. The residue is dissolved in 5 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 40 mg of 4-diethylaminomethyl-N-[5-(N'-methyl-N'-phenylhydrazinocarbonyl)-1H-thieno[2,3-c]pyrazol-3-yl]benzamide trifluoroacetate are thus obtained in the form of a yellow powder melting from 158 to 170° C. $^1$H NMR (300 MHz, (CD$_3$)$_2$SO-d$_6$, δ in ppm): observation of an 80%-20% mixture of conformers, with 1.25 (t, J=7.0 Hz, 6H); 3.11 (m, 4H); 3.18 (s, 3H); 4.41 (d, J=5.5 Hz, 2H); 6.77 (t, J=7.5 Hz, 0.8H); 6.82 (d, J=8.0 Hz, 1.6H); 6.94 (t, J=7.5 Hz, 0.2H); 7.02 (d, J=8.0 Hz, 0.4H); 7.22 (t, J=8.0 Hz, 1.8H); 7.31 (t, J=8.0 Hz, 0.2H); 7.69 (broad d, J=8.0 Hz, 2H); 8.17 (partially masked d, J=8.0 Hz, 2H); 8.18 (s, 1H); 9.51 (broad multiplet, 1H); 9.71 (s, 0.2H); 10.75 (s, 0.8H); 11.25 (broad s, 0.2H); 11.35 (broad s, 0.8H); 13.0 (very broad m, 1H).

14 mg of N-{5-[N'-(4-chlorophenyl)-N'-methylhydrazinocarbonyl]-1H-thieno[2,3-c]pyrazol-3-yl}-4-diethylaminomethylbenzamide are isolated in the same manner, in the form of a pale yellow solid melting from 170 to 178° C. LC-MS-DAD-ELSD: 511(+)/ . . . =(M+H)(+)/ . . . (1 Cl).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 16a AND 16b

Preparation of N-[5-(N'-methyl-N'-phenylhydrazinocarbonyl)-1H-thieno[2,3-c]pyrazol-3-yl]-3-(4-methylpiperazin-1-ylmethyl)-benzamide and N-[5-(N'-(4-chlorophenyl)-N'-methylhydrazinocarbonyl)-1H-thieno[2,3-c]pyrazol-3-yl]-3-(4-methylpiperazin-1-ylmethyl)benzamide

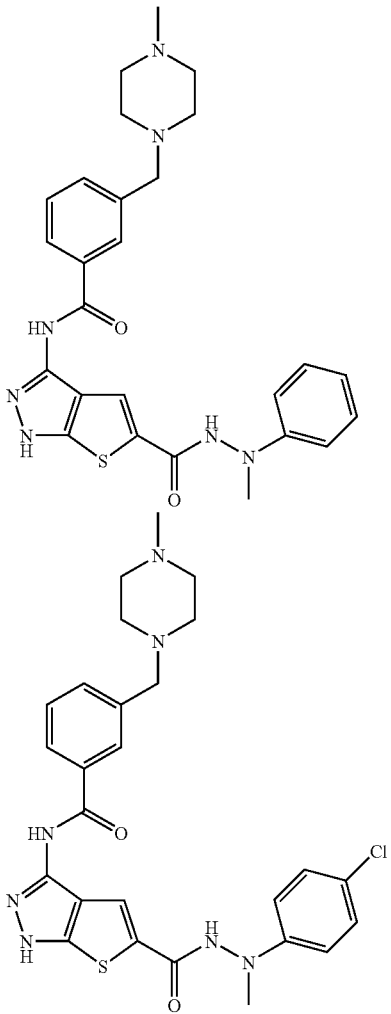

A solution of 0.07 g (116 μmol) of an approximately 70:30 mixture of tert-butyl 5-(N'-methyl-N'-phenylhydrazinocarbonyl)-3-[3-(4-methylpiperazin-1-ylmethyl)-benzoylamino]thieno[2,3-c]pyrazole-1-carboxylate and tert-butyl 5-(N'-(4-chlorophenyl)-N'-methylhydrazinocarbonyl)-3-[3-(4-methylpiperazin-1-ylmethyl)-benzoylamino]thieno[2,3-c]pyrazole-1-carboxylate in 4 mL of methanol is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 70 mg of N-[5-(N'-methyl-N'-phenylhydrazinocarbonyl)-1H-thieno[2,3-c]pyrazol-3-yl]-3-(4-methylpiperazin-1-ylmethyl)benzamide are thus obtained in the form of a yellow powder melting from 149 to 156° C. LC-MS-DAD-ELSD: 502(−)=(M−H)(−); 504(+)=(M+H)(+).

29 mg of N-[5-(N'-(4-chlorophenyl)-N'-methylhydrazinocarbonyl)-1H-thieno[2,3-c]pyrazol-3-yl]-3-(4-methylpiperazin-1-ylmethyl)benzamide are isolated in the same manner, in the form of a pale yellow powder melting from 149 to 159° C. $^1$H NMR (400 MHz, $(CD_3)_2SO-d_6$, δ in ppm): 2.43 (partially masked broad multiplet, 2H); 2.79 (s, 3H); 3.03 (broad multiplet, 2H); 3.17 (s, 3H); from 3.25 to 3.88 (partially masked m, 4H); 3.74 (broad s, 2H); 6.82 (d, J=9.0 Hz, 2H); 7.25 (d, J=9.0 Hz, 2H); 7.54 (t, J=8.0 Hz, 1H); 7.57 (d, J=8.0 Hz, 1H); 8.01 (partially masked d, J=8.0 Hz, 1H); 8.02 (s, 1H); 8.18 (s, 1H); 9.50 (very broad m, 1H); 10.8 (s, 1H); 11.25 (s, 1H).

tert-Butyl 5-(N'-methyl-N'-phenylhydrazinocarbonyl)-3-[3-(4-methylpiperazin-1-ylmethyl)benzoylamino]thieno[2,3-c]pyrazole-1-carboxylate and tert-butyl 5-(N'-(4-chlorophenyl)-N'-methylhydrazinocarbonyl)-3-[3-(4-methylpiperazin-1-ylmethyl)benzoylamino]thieno[2,3-c]pyrazole-1-carboxylate

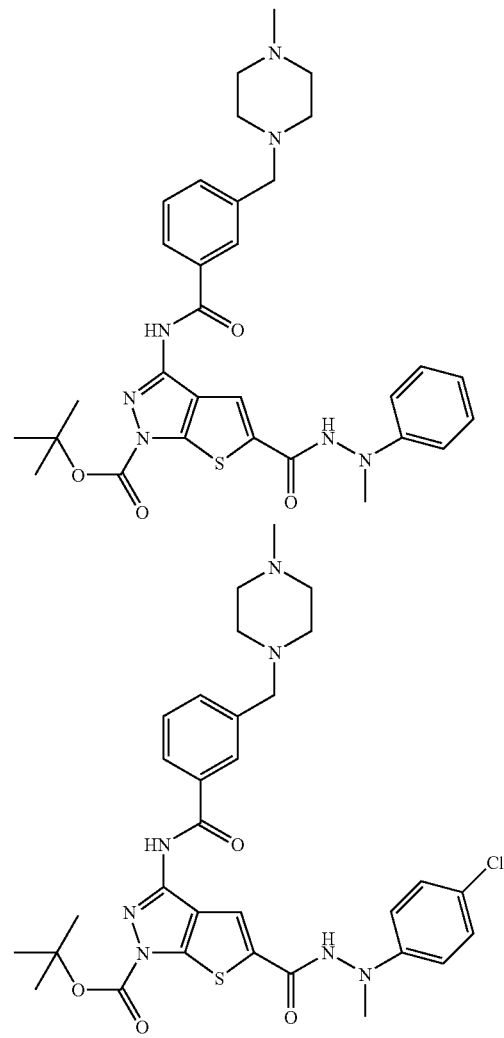

143 mg (1.03 mmol) of potassium carbonate and 261 mg (1.03 mmol) of 3-(4-methylpiperazin-1-ylmethyl)benzoyl chloride hydrochloride are added to a solution of 0.20 g (0.52 mmol) of an approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate in 15 mL of tetrahydrofuran under argon. The reaction mixture is stirred at a temperature in the region of 25° C. for 16 hours, and then refluxed for 3 hours. A further 261 mg (1.03 mmol) of 3-(4-methylpiperazin-1-ylmethyl)benzoyl chloride hydrochloride are added and stirring is continued at reflux for 4 hours, and then at a temperature in the region of 25° C. for 16 hours. A further 143 mg (1.03 mmol) of potassium carbonate are added and stirring is continued at reflux for 4 hours, and then at a temperature in the region of 25° C. for 16 hours. The reaction mixture is then cooled to a temperature in the region of 25° C., and then poured into ice-cold water. The mixture is extracted with ethyl acetate. The organic phases are combined, dried over magnesium sulfate, filtered and then concentrated to dryness under vacuum (2 kPa) at a temperature in the region of 40° C. The residue is purified by chromatography on a cartridge of 70 g of silica gel (0.015-0.040 mm), eluting with dichloromethane/methanol mixtures (95/5 and then 99/1 by volume) at a flow rate of 40 mL/min. The fractions containing the expected product are combined and then concentrated to dryness under reduced pressure (2 kPa) at a temperature in the region of 40° C. 0.07 g of an approximately 70:30 mixture of tert-butyl 5-(N'-methyl-N'-phenylhydrazinocarbonyl)-3-[3-(4-methylpiperazin-1-ylmethyl)benzoylamino]thieno[2,3-c]pyrazole-1-carboxylate and tert-butyl 5-(N'-(4-chlorophenyl)-N'-methylhydrazinocarbonyl)-3-[3-(4-methylpiperazin-1-ylmethyl)benzoylamino]-thieno[2,3-c]pyrazole-1-carboxylate is thus obtained in the form of a white powder, which product is used directly in the following step. LC-MS-DAD-ELSD: major product 604(+)=(M+H)(+); 602(−)=(M−H)(−).

The approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate is described in example 11. 3-(4-Methylpiperazin-1-ylmethyl)benzoyl chloride hydrochloride may be prepared according to patent WO 03/066 613 A1.

EXAMPLES 17a AND 17b

Preparation of N-[5-(N'-methyl-N'-phenylhydrazinocarbonyl)-1H-thieno[2,3-c]pyrazol-3-yl]-4-piperidin-1-ylmethylbenzamide and N-[5-(N'-(4-chlorophenyl)-N'-methylhydrazinocarbonyl)-1H-thieno[2,3-c]-pyrazol-3-yl]-4-piperidin-1-ylmethylbenzamide

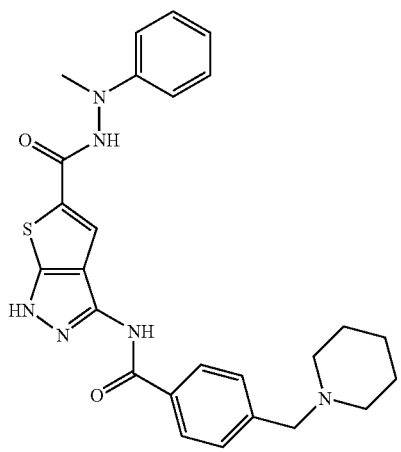

-continued

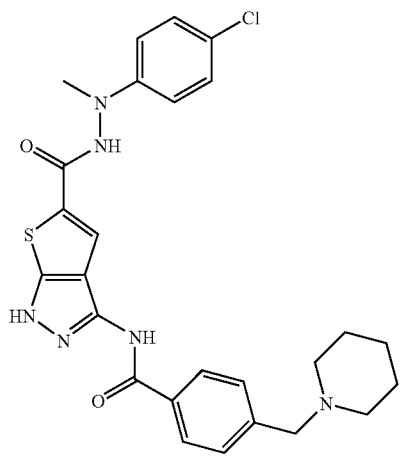

27 mg (74 μmol) of tetrabutylammonium iodide and then 110 μL (1.11 mmol) of piperidine are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 75 mg of N-[5-(N'-methyl-N'-phenylhydrazinocarbonyl)-1H-thieno[2,3-c]pyrazol-3-yl]-4-piperidin-1-ylmethylbenzamide are thus obtained in the form of a yellow powder melting from 170 to 182° C. LC-MS-DAD-ELSD: 487(−)= (M−H)(−); 489(+)=(M+H)(+).

5 mg of N-[5-(N'-(4-chlorophenyl)-N'-methylhydrazinocarbonyl)-1H-thieno[2,3-c]-pyrazol-3-yl]-4-piperidin-1-ylmethylbenzamide are isolated in the same manner, in the form of a pale yellow powder. LC-MS-DAD-ELSD: 523(+)/ . . . =(M+H)(+)/ . . . (1 Cl).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 18a AND 18b

Preparation of N-[5-(N'-methyl-N'-phenylhydrazinocarbonyl)-1H-thieno[2,3-c]pyrazol-3-yl]-4-pyrrolidin-1-ylmethylbenzamide and N-[5-(N'-(4-chlorophenyl)-N'-methylhydrazinocarbonyl)-1H-thieno[2,3-c]pyrazol-3-yl]-4-pyrrolidin-1-ylmethylbenzamide

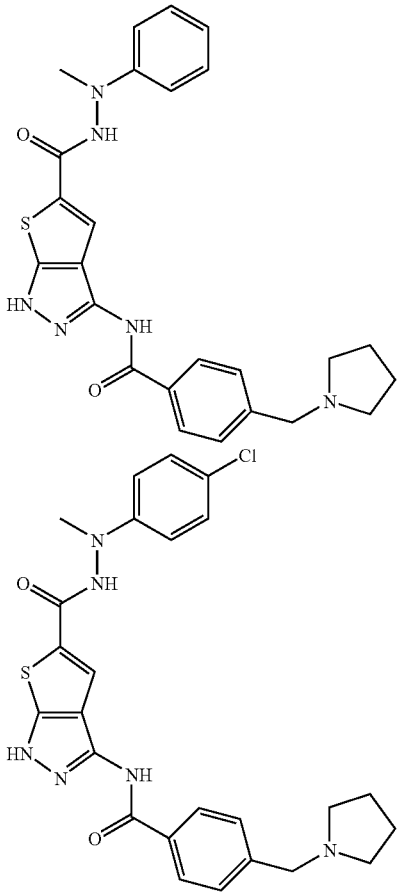

27 mg (74 μmol) of tetrabutylammonium iodide and then 93 μL (1.11 mmol) of pyrrolidine are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 25 mg of N-[5-(N'-methyl-N'-phenylhydrazinocarbonyl)-1H-thieno[2,3-c]pyrazol-3-yl]-4-pyrrolidin-1-ylmethylbenzamide are thus obtained in the form of a yellow powder melting from 172 to 178° C. LC-MS-DAD-ELSD: 475(+)= (M+H)(+).

18 mg of N-[5-(N'-(4-chlorophenyl)-N'-methylhydrazinocarbonyl)-1H-thieno[2,3-c]pyrazol-3-yl]-4-pyrrolidin-1-ylmethylbenzamide are isolated in the same manner, in the form of a pale yellow powder melting from 170 to 179° C. $^1$H NMR (400 MHz, (CD$_3$)$_2$SO-d$_6$, δ in ppm): This is the salt of the expected structure, with 1.87 (m, 2H); 2.05 (m, 2H); 3.13 (m, 2H); 3.18 (s, 3H); 3.40 (m, 2H); 4.45 (d, J=4.5 Hz, 2H); 6.82 (d, J=9.0 Hz, 2H); 7.25 (d, J=9.0 Hz, 2H); 7.68 (d, J=8.0 Hz, 2H); 8.16 (d, J=8.0 Hz, 2H); 8.18 (s, 1H); 9.85 (broad multiplet, 1H); 10.85 (s, 1H); 11.35 (broad s, 1H); 13.0 (very broad m, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLE 19

Preparation of 4-azetidin-1-ylmethyl-N-[5-(N'-methyl-N'-phenylhydrazinocarbonyl)-1H-thieno[2,3-c]pyrazol-3-yl]benzamide

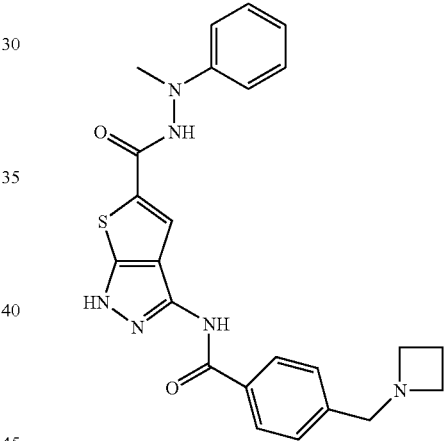

27 mg (74 μmol) of tetrabutylammonium iodide and then 75 μL (1.11 mmol) of azetidine are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 3 mg of 4-azetidin-1-ylmethyl-N-[5-(N'-methyl-N'-phenylhydrazinocarbonyl)-1H-thieno

[2,3-c]pyrazol-3-yl]benzamide are thus obtained in the form of a yellow powder melting from 155 to 160° C. LC-MS-DAD-ELSD: 461(+)=(M+H)(+).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 20a AND 20b

Preparation of 4-{[(2-dimethylaminoethyl)methylamino]methyl}-N-[5-(N'-methyl-N'-phenylhydrazinocarbonyl)-1H-thieno[2,3-c]pyrazol-3-yl]benzamide and N-{5-[N'-(4-chlorophenyl)-N'-methylhydrazinocarbonyl]-1H-thieno[2,3-c]pyrazol-3-yl}-4-{[(2-dimethylaminoethyl)methylamino]methyl}benzamide

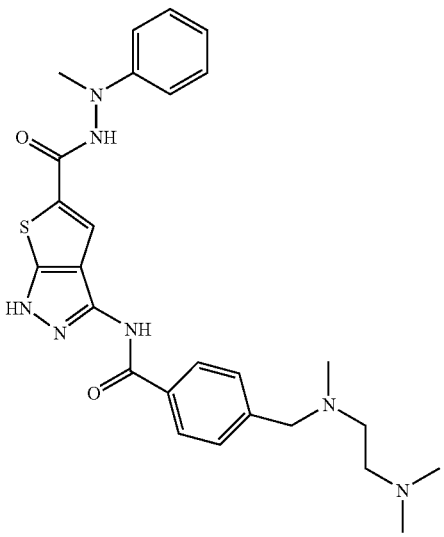

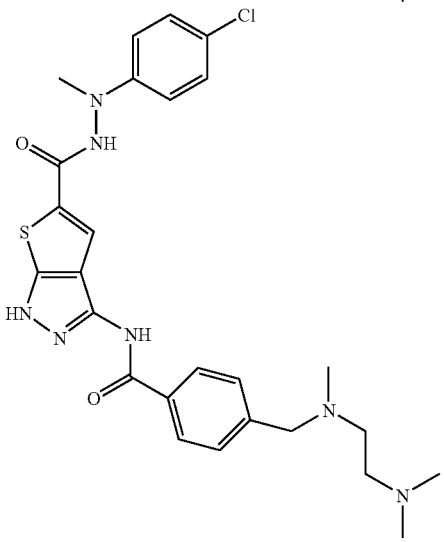

27 mg (74 µmol) of tetrabutylammonium iodide and then 144 µL (1.11 mmol) of N,N,N'-trimethylethylenediamine are added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 6 mL of dimethylformamide under argon. The reaction mixture is stirred at a temperature in the region of 25° C. for 16 hours and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 40 mg of 4-{[(2-dimethylaminoethyl)methylamino]methyl}-N-[5-(N'-methyl-N'-phenylhydrazinocarbonyl)-1H-thieno[2,3-c]pyrazol-3-yl]benzamide are thus obtained in the form of a yellow powder. LC-MS-DAD-ELSD: 506(+)=(M+H)(+).

26 mg of N-{5-[N'-(4-chlorophenyl)-N'-methylhydrazinocarbonyl]-1H-thieno[2,3-c]pyrazol-3-yl}-4-{[(2-dimethylaminoethyl)methylamino]methyl}benzamide are isolated in the same manner, in the form of a colorless resin. $^1$H NMR (400 MHz, (CD$_3$)$_2$SO-d$_6$, δ in ppm): 2.44 (partially masked broad multiplet, 7H); 2.82 (s, 6H); 3.17 (s, 3H); 3.37 (broad m, 2H); 6.82 (d, J=9.0 Hz, 2H); 7.25 (d, J=9.0 Hz, 2H); 7.60 (broad d, J=8.0 Hz, 2H); 8.12 (d, J=8.0 Hz, 2H); 8.18 (s, 1H); 10.85 (s, 1H); 11.25 (broad s, 1H); 13.0 (very broad m, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 21a AND 21b

Preparation of N-[5-(N'-methyl-N'-phenylhydrazinocarbonyl)-1H-thieno[2,3-c]pyrazol-3-yl]-4-perhydro-1,4-oxazepin-4-ylmethylbenzamide and N-{5-[N'-(4-chlorophenyl)-N'-methylhydrazinocarbonyl]-1H-thieno[2,3-c]pyrazol-3-yl}-4-perhydro-1,4-oxazepin-4-ylmethylbenzamide

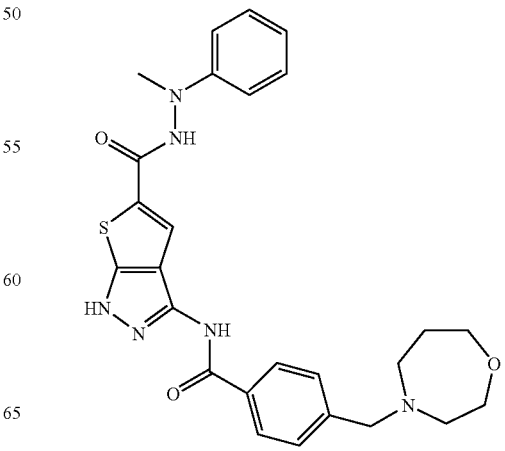

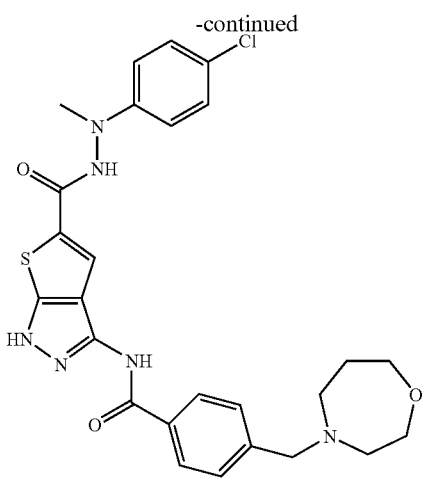

27 mg (74 µmol) of tetrabutylammonium iodide, 153 mg (1.11 mmol) of homomorpholine hydrochloride and 153 mg (1.11 mmol) of potassium carbonate are successively added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 34 mg of N-[5-(N'-methyl-N'-phenylhydrazinocarbonyl)-1H-thieno[2,3-c]pyrazol-3-yl]-4-perhydro-1,4-oxazepin-4-ylmethylbenzamide are thus obtained in the form of a yellow powder melting from 174 to 179° C. LC-MS-DAD-ELSD: 505(+)=(M+H)(+). 38 mg of N-{5-[N'-(4-chlorophenyl)-N'-methylhydrazinocarbonyl]-1H-thieno[2,3-c]pyrazol-3-yl}-4-perhydro-1,4-oxazepin-4-ylmethylbenzamide are isolated in the same manner, in the form of a yellow powder. $^1$H NMR (400 MHz, (CD$_3$)$_2$SO-d$_6$, δ in ppm): This is the salt of the expected structure, with 2.08 (m, 2H); from 3.13 to 4.07 (m, 8H); 3.18 (s, 3H); 4.50 (broad s, 2H); 6.82 (d, J=9.0 Hz, 2H); 7.25 (d, J=9.0 Hz, 2H); 7.70 (broad d, J=8.0 Hz, 2H); 8.17 (partially masked d, J=8.0 Hz, 2H); 8.18 (s, 1H); 9.75 (broad multiplet, 1H); 10.85 (s, 1H); 11.3 (s, 1H); 12.95 (very broad m, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLES 22a AND 22b

Preparation of N-[5-(N'-methyl-N'-phenylhydrazinocarbonyl)-1H-thieno[2,3-c]pyrazol-3-yl]-3-morpholin-4-ylmethylbenzamide and N-{5-[N'-(4-chlorophenyl)-N'-methylhydrazinocarbonyl]-1H-thieno[2,3-c]pyrazol-3-yl}-3-morpholin-4-ylmethylbenzamide

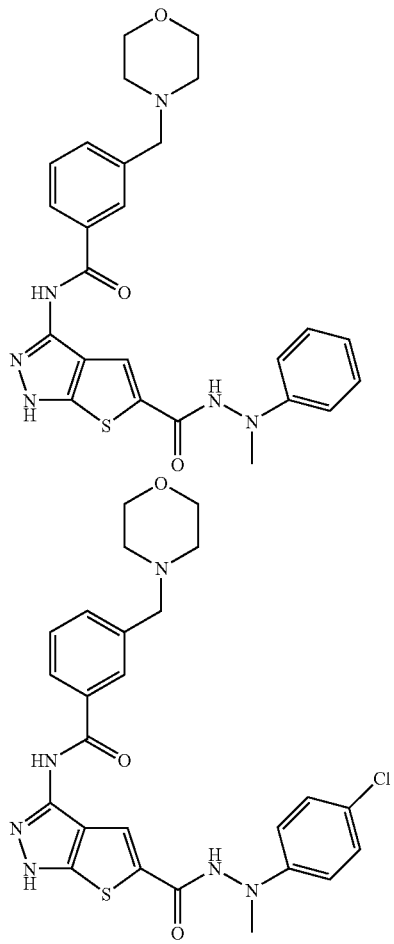

A solution of 257 mg (0.44 mmol) of an approximately 70:30 mixture of tert-butyl 5-(N'-methyl-N'-phenylhydrazinocarbonyl)-3-(3-morpholin-4-ylmethylbenzoylamino)thieno[2,3-c]pyrazole-1-carboxylate and tert-butyl 5-(N'-(4-chlorophenyl)-N'-methylhydrazinocarbonyl)-3-(3-morpholin-4-ylmethylbenzoylamino)thieno[2,3-c]pyrazole-1-carboxylate in 4 mL of methanol is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). 105 mg of N-[5-(N'-methyl-N'-phenylhydrazinocarbonyl)-1H-thieno[2,3-c]pyrazol-3-yl]-3-morpholin-4-ylmethylbenzamide are thus obtained in the form of a yellow powder melting from 168 to 178° C. $^1$H NMR (400 MHz, (CD$_3$)$_2$SO-d$_6$, δ in ppm): observation of the salt of the expected structure, with an 80%-20% mixture of conformers, such that: 3.16 (partially masked broad m, 2H); 3.18 (s, 3H);

3.32 (broad m, 2H); 3.63 (broad m, 2H); 3.98 (m, 2H); 4.44 (broad s, 2H); 6.77 (t, J=7.5 Hz, 0.8H); 6.82 (d, J=8.0 Hz, 1.6H); 6.94 (t, J=8.0 Hz, 0.2H); 7.02 (d, J=8.0 Hz, 0.4H); 7.22 (t, J=8.0 Hz, 1.6H); 7.31 (d, J=8.0 Hz, 0.4H); 7.66 (t, J=8.0 Hz, 1H); 7.74 (d, J=8.5 Hz, 1H); 8.15 (m, 3H); 9.70 (s, 0.2H); 10.0 (broad multiplet, 1H); 10.75 (s, 0.8H); 11.25 (s, 0.2H); 11.35 (s, 0.8H); 12.95 (very broad m, 1H).

34 mg of N-{5-[N'-(4-chlorophenyl)-N'-methylhydrazinocarbonyl]-1H-thieno[2,3-c]pyrazol-3-yl}-3-morpholin-4-ylmethylbenzamide are isolated in the same manner, in the form of a yellow powder. $^1$H NMR (400 MHz, (CD$_3$)$_2$SO-d$_6$, δ in ppm): This is a salt of the expected structure, with: from 3.07 to 3.55 (partially masked m, 4H); 3.18 (s, 3H); 3.63 (broad t, J=12.5 Hz, 2H); 3.99 (broad d, J=12.5 Hz, 2H); 4.44 (broad s, 2H); 6.82 (d, J=9.0 Hz, 2H); 7.25 (d, J=9.0 Hz, 2H); from 7.60 to 7.76 (m, 2H); 8.17 (m, 3H); 9.90 (broad multiplet, 1H); 10.8 (s, 1H); 11.3 (broad s, 1H); 13.0 (very broad m, 1H).

tert-Butyl 5-(N'-methyl-N'-phenylhydrazinocarbonyl)-3-[3-(4-methylpiperazin-1-ylmethyl)benzoylamino]thieno[2,3-c]pyrazole-1-carboxylate and tert-butyl 5-(N'-(4-chlorophenyl)-N'-methylhydrazinocarbonyl)-3-[3-(4-methylpiperazin-1-ylmethyl)benzoylamino]thieno[2,3-c]pyrazole-1-carboxylate

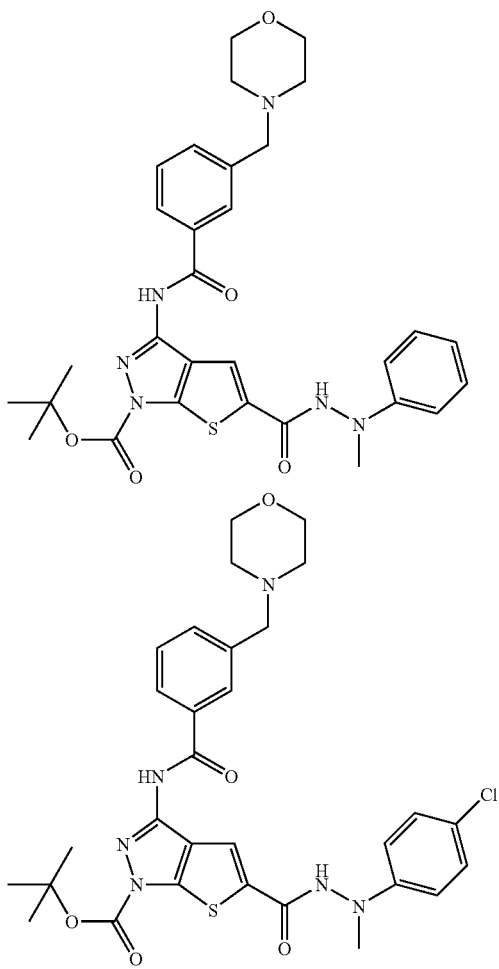

214 mg (1.55 mmol) of potassium carbonate and 285 mg (1.03 mmol) of 3-(morpholin-1-ylmethyl)benzoyl chloride hydrochloride are added to a solution of 0.20 g (0.52 mmol) of an approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate in 15 mL of tetrahydrofuran under argon. The reaction mixture is stirred at a temperature in the region of 25° C. for 16 hours, and then poured into ice-cold water. The mixture is extracted with ethyl acetate. The organic phases are combined, dried over magnesium sulfate, filtered and then concentrated to dryness under vacuum (2 kPa) at a temperature in the region of 40° C. The residue is purified by chromatography on a cartridge of 30 g of silica gel (0.015-0.040 mm), eluting with pure dichloromethane and then with a dichloromethane/methanol mixture (90/10 by volume). The fractions containing the expected products are combined and then concentrated to dryness under reduced pressure (2 kPa) at a temperature in the region of 40° C. 257 mg of an approximately 70:30 mixture of tert-butyl 5-(N'-methyl-N'-phenylhydrazinocarbonyl)-3-(3-morpholin-4-ylmethylbenzoylamino)thieno[2,3-c]pyrazole-1-carboxylate and tert-butyl 5-(N'-(4-chlorophenyl)-N'-methylhydrazinocarbonyl)-3-(3-morpholin-4-ylmethylbenzoylamino)thieno[2,3-c]pyrazole-1-carboxylate are thus obtained in the form of a yellow foam, which product is used directly in the following step.

The approximately 70:30 mixture of tert-butyl 3-amino-5-(N'-methyl-N'-phenylhydrazinocarbonyl)thieno[2,3-c]pyrazole-1-carboxylate and tert-butyl 3-amino-5-(N'-(4-chlorophenyl)-N'-methylhydrazinocarbonyl)thieno[2,3-c]pyrazole-1-carboxylate is described in example 11. 3-(Morpholin-1-ylmethyl)benzoyl chloride hydrochloride may be prepared according to patent WO 90/08128 A1.

EXAMPLES 23a AND 23b

Preparation of 4-[(2-diethylaminoethylamino)methyl]-N-[5-(N'-methyl-N'-phenylhydrazinocarbonyl)-1H-thieno[2,3-c]pyrazol-3-yl]-benzamide and N-{5-[N'-(4-chlorophenyl)-N'-methylhydrazinocarbonyl]-1H-thieno[2,3-c]pyrazol-3-yl}-4-[(2-diethylaminoethylamino)methyl]benzamide

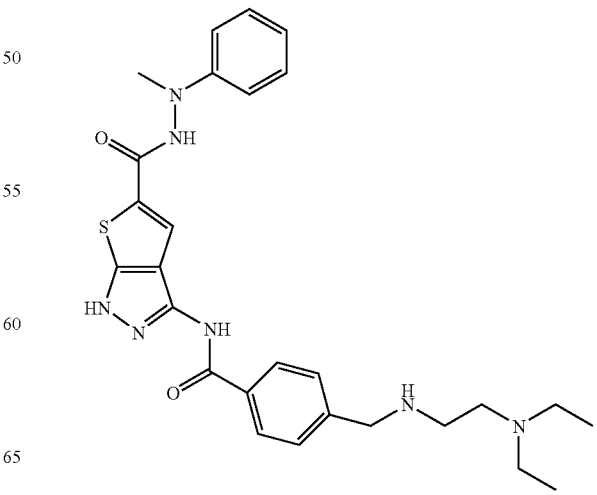

-continued

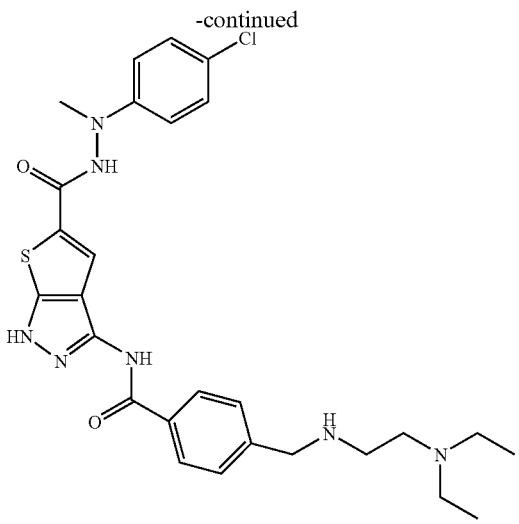

27 mg (74 μmol) of tetrabutylammonium iodide, 156 μL (1.11 mmol) of N,N-diethylethylenediamine and 153 mg (1.11 mmol) of potassium carbonate are successively added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)-thieno[2,3-c]pyrazole-1-carboxylate in 6 mL of dimethylformamide under argon. The reaction mixture is stirred at a temperature in the region of 25° C. for 16 hours, and then poured onto ice. It is then extracted twice with a 50/50 mixture of ethyl acetate and heptane. The organic extracts are combined, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by preparative LC/MS (conditions B). The fractions containing the expected products are combined and then concentrated to dryness under reduced pressure (2 kPa) at a temperature in the region of 40° C. The residue is repurified by chromatography on a cartridge of 4 g of silica gel (0.035-0.060 mm), eluting with a dichloromethane/methanol mixture and then with a mixture of dichloromethane and methanol/28% aqueous ammonia (85/15 by volume). The fractions containing the expected products are combined and then concentrated to dryness under reduced pressure (2 kPa) at a temperature in the region of 40° C. 8 mg of 4-[(2-diethylaminoethylamino)methyl]-N-[5-(N'-methyl-N'-phenylhydrazinocarbonyl)-1H-thieno[2,3-c]pyrazol-3-yl]benzamide are thus obtained in the form of a pale yellow powder melting from 143 to 150° C. LC-MS-DAD-ELSD: 520(+)/ . . . =(M+H)(+)/ . . . (1 Cl).

10 mg of N-{5-[N'-(4-chlorophenyl)-N'-methylhydrazinocarbonyl]-1H-thieno[2,3-c]pyrazol-3-yl}-4-[(2-diethylaminoethylamino)methyl]benzamide are isolated in the same manner, in the form of a yellow powder. $^1$H NMR (400 MHz, $(CD_3)_2SO$-$d_6$, δ in ppm): This is the salt of the expected structure, with 1.21 (broad t, J=7.0 Hz, 6H); 3.18 (s, 3H); 3.20 (partially masked broad multiplet, 6H); from 3.29 to 3.54 (masked m, 2H); 4.31 (broad m, 2H); 6.82 (d, J=9.0 Hz, 2H); 7.25 (d, J=9.0 Hz, 2H); 7.64 (broad d, J=8.0 Hz, 2H); 8.16 (d, J=8.0 Hz, 2H); 8.19 (s, 1H); 9.20 (broad multiplet, 2H); 10.85 (s, 1H); 11.3 (broad s, 1H); 13.0 (very broad m, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLE 24

Preparation of 4-[(methylphenylamino)methyl]-N-[5-(N'-methyl-N'-phenylhydrazinocarbonyl)-1H-thieno[2,3-c]pyrazol-3-yl]benzamide

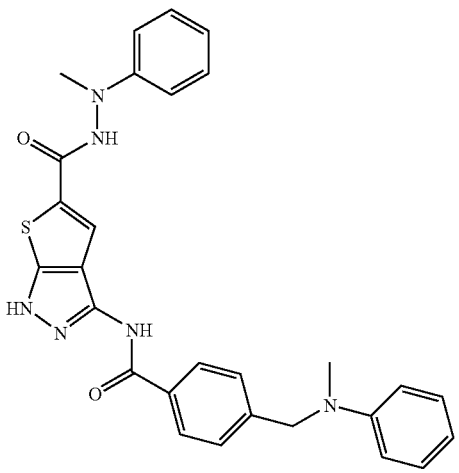

27 mg (74 μmol) of tetrabutylammonium iodide and 121 μL (1.11 mmol) of N-methylaniline are successively added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 6 mL of dimethylformamide under argon. The reaction mixture is stirred at a temperature in the region of 25° C. for 15 days, and then poured onto ice. It is then extracted twice with a 50/50 mixture of ethyl acetate and heptane. The organic extracts are combined, washed with saturated brine, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes. The reaction mixture is then concentrated to dryness under vacuum (2 kPa) at a temperature in the region of 40° C. The residue is purified by chromatography on a cartridge of 15 g of silica gel (0.015-0.040 mm), eluting with pure dichloromethane and then with a dichloromethane/methanol/28% aqueous ammonia mixture (12/3/0.5 by volume) at a flow rate of 10 mL/min. The fractions containing the expected product are combined and then concentrated to dryness under reduced pressure (2 kPa) at a temperature in the region of 40° C. The residue is purified by preparative LC/MS (conditions B). 11 mg of 4-[(methylphenylamino)methyl]-N-[5-(N'-methyl-N'-phenylhydrazinocarbonyl)-1H-thieno[2,3-c]pyrazol-3-yl]benzamide are thus obtained in the form of a beige-colored powder melting at 242° C. LC-MS-DAD-ELSD: 511(+)=(M+H)(+).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLE 25

Preparation of 4-[(diisopropylamino)methyl]-N-[5-(N'-methyl-N'-phenylhydrazinocarbonyl)-1H-thieno[2,3-c]pyrazol-3-yl]benzamide trifluoroacetate

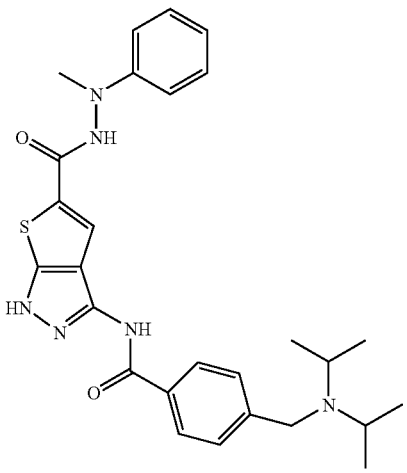

27 mg (74 μmol) of tetrabutylammonium iodide and 156 μL (1.11 mmol) of diisopropylamine are successively added to a solution of 200 mg (0.37 mmol) of an approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate in 6 mL of dimethylformamide under argon. The reaction mixture is stirred at a temperature in the region of 25° C. for 9 days, a further 220 μL (1.56 mmol) of diisopropylamine are then added and the reaction mixture is stirred at a temperature in the region of 25° C. for 6 days. It is then poured onto ice and extracted twice with a 50/50 mixture of ethyl acetate and heptane. The organic extracts are combined, washed with saturated brine, dried over magnesium sulfate and then concentrated to dryness under vacuum (2 kPa) at a temperature in the region of 40° C. The residue is dissolved in 4 mL of methanol and the solution is introduced into a microwave oven tube. The tube is stoppered and the reaction mixture is irradiated at a temperature in the region of 100° C. for 30 minutes.

The reaction mixture is then concentrated to dryness under vacuum (2 kPa) at a temperature in the region of 40° C. The residue is purified by preparative LC/MS (conditions B). 10 mg of 4-[(diisopropylamino)methyl]-N-[5-(N'-methyl-N'-phenylhydrazinocarbonyl)-1H-thieno[2,3-c]pyrazol-3-yl] benzamide trifluoroacetate are thus obtained in the form of a beige-colored powder melting from 170 to 182° C. $^1$H NMR (400 MHz, (CD$_3$)$_2$SO-d$_6$, δ in ppm): for this batch, all the signals are broad, with: from 1.27 to 1.42 (m, 12H); 3.18 (s, 3H); 3.70 (m, 2H); 4.48 (s, 2H); from 6.71 to 6.88 (m, 3H); 7.22 (t, J=8.0 Hz, 2H); 7.70 (m, 2H); 8.17 (m, 3H); 8.55 (s, 1H); 10.75 (s, 1H); 11.3 (s, 1H); 13.05 (s, 1H).

The approximately 70:30 mixture of tert-butyl 3-(4-chloromethylbenzoylamino)-5-(N'-methyl-N'-phenylhydrazinocarbonyl)thieno[2,3-c]pyrazole-1-carboxylate and tert-butyl 3-(4-chloromethylbenzoylamino)-5-(N'-(4-chlorophenyl)-N'-methylhydrazinocarbonyl)thieno[2,3-c]pyrazole-1-carboxylate is described in example 11.

EXAMPLE 26

Preparation of N-[5-(N'-benzylhydrazinocarbonyl)-1H-thieno[2,3-c]pyrazol-3-yl]-4-methoxybenzamide

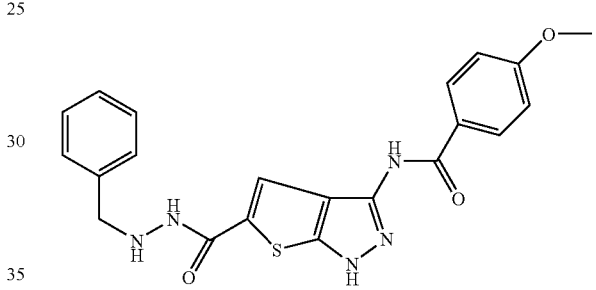

N-[5-(N'-Benzylhydrazinocarbonyl)-1H-thieno[2,3-c]pyrazol-3-yl]-4-methoxybenzamide is prepared according to example 1. Yield=3%. MS: ES m/z=422 MH+ base peak. $^1$H NMR (400 MHz, (CD$_3$)$_2$SO-d$_6$, δ in ppm): 3.85 (s, 3H); 3.98 (s, 2H); 7.06 (d, J=8.5 Hz, 2H); 7.26 (t, J=7.5 Hz, 1H); 7.33 (t, J=7.5 Hz, 2H); 7.38 (d, J=7.5 Hz, 2H); 7.94 (broad s, 1H); 8.05 (d, J=8.5 Hz, 2H); 10.15 (s, 1H); 10.95 (broad multiplet, 1H); 12.85 (very broad m, 1H).

EXAMPLE 27

Preparation of 4-methoxy-N-[5-(N'-pyrid-2-ylhydrazinocarbonyl)-1H-thieno[2,3-c]pyrazol-3-yl]benzamide

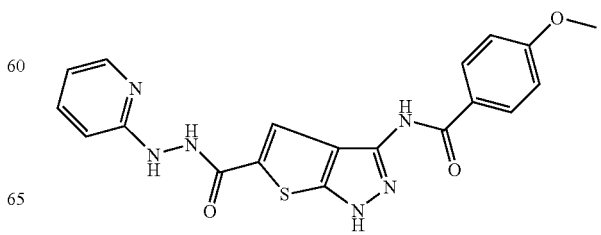

4-Methoxy-N-[5-(N'-pyrid-2-ylhydrazinocarbonyl)-1H-thieno[2,3-c]pyrazol-3-yl]-benzamide is prepared according to example 1. Yield=56%. MS: EI m/z=408M+.

m/z=300 (M–$C_5H_6N_3$)+ m/z=135 $C_8H_7O_2$+ base peak.

$^1$H NMR (400 MHz, $(CD_3)_2SO$-$d_6$, δ in ppm): 3.85 (s, 3H); 6.63 (d, J=8.5 Hz, 1H); 6.71 (m, 1H); 7.07 (broad d, J=8.5 Hz, 2H); 7.54 (m, 1H); from 8.03 to 8.12 (m, 3H); 8.20 (s, 1H); 8.44 (s, 1H); 10.5 (s, 1H); 11.0 (s, 1H); 12.9 (s, 1H).

EXAMPLE 28

Preparation of N-{5-[N'-(4-chlorophenyl)-N'-methylhydrazinocarbonyl]-1H-thieno[2,3-c]pyrazol-3-yl}-4-(4-methylpiperazin-1-yl)benzamide

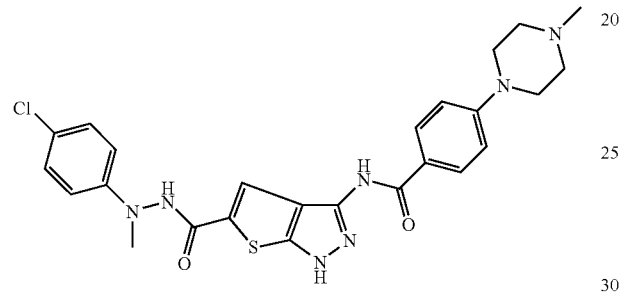

Ethyl 1-(1-ethoxyethyl)-3-[4-(4-methylpiperazin-1-yl)benzoylamino]-1H-thieno[2,3-c]pyrazole-5-carboxylate (0.5 g, 1.03 mmol, 1 eq.) and toluene (5 mL) are placed in a dry 20 mL round-bottomed flask under argon. The suspension is stirred at a temperature in the region of 0° C., and a solution of trimethylaluminum (1.54 mL, 3 eq.) is then added dropwise to avoid rises in temperature. Once the addition is complete, the mixture is left stirring for 30 minutes at a temperature in the region of 25° C., followed by addition of a solution of N-(4-chlorophenyl)-N-methylhydrazine (0.480 g, 3.09 mmol, 3 eq.). The reaction mixture is then heated to a temperature in the region of 50° C. until the starting material has totally disappeared. After 2 hours 30 minutes, the mixture is allowed to return to a temperature in the region of 25° C., and is then diluted with ethyl acetate. A few drops of monopotassium phosphate are added thereto, until the evolution of gas has ceased, and the mixture is then left stirring for one hour. The solvent is then evaporated off and then the residue is dissolved in a mixture of dichloromethane and methanol. This solution is placed directly onto silica gel for purification by chromatography, eluting at the start with a methanol/dichloromethane mixture (10/90 by volume). Ethoxyethyl intermediate: LC/MS RT=3.41 min.; M+H+ 596.1. M–H– 594.2. After evaporation, the solid obtained is placed directly in 5 mL of tetrahydrofuran and 2 mL of 5 N hydrochloric acid at a temperature in the region of 50° C. N-{5-[N'-(4-Chlorophenyl)-N'-methylhydrazinocarbonyl]-1H-thieno[2,3-c]pyrazol-3-yl}-4-(4-methylpiperazin-1-yl)benzamide is thus obtained (119 mg, 22% for the two steps). MS: ES m/z=524 MH+ base peak. $^1$H NMR (400 MHz, $(CD_3)_2SO$-$d_6$, δ in ppm): 2.23 (s, 3H); 2.44 (m, 4H); 3.17 (s, 3H); from 3.25 to 3.33 (partially masked m, 4H); 6.82 (d, J=9.0 Hz, 2H); 7.00 (broad d, J=9.0 Hz, 2H); 7.24 (d, J=9.0 Hz, 2H); 7.97 (broad d, J=9.0 Hz, 2H); 8.16 (s, 1H); 10.8 (s, 1H); 10.9 (broad multiplet, 1H); 12.9 (broad multiplet, 1H).

Ethyl 1-(1-ethoxyethyl)-3-[4-(4-methylpiperazin-1-yl)benzoylamino]-1H-thieno-[2,3-c]pyrazole-5-carboxylate

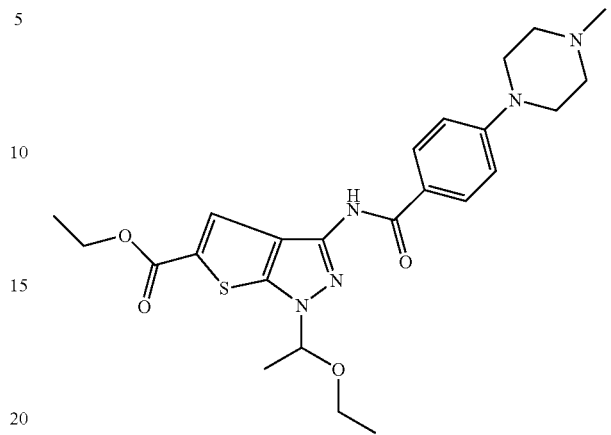

Ethyl 3-bromo-1-(1-ethoxyethyl)-1H-thieno[2,3-c]pyrazole-5-carboxylate (10.9 g, 31 mmol), 4-(4-methylpiperazin-1-yl)benzamide (9 g, 41 mmol, 1.3 eq.), copper(I)iodide (0.601 g, 3.1 mmol, 0.1 eq.), preground tripotassium phosphate (20.1 g, 94 mmol, 3 eq.) and 70 mL of anhydrous dioxane degassed beforehand with argon are placed in a 500 mL round-bottomed flask under argon. N,N'-Dimethylethylenediamine (0.336 mL, 3.16 mmol, 0.1 eq.) is added to this suspension by syringe. The reaction mixture is then heated at a temperature in the region of 110° C. for a period of 24 hours. The dioxane is then evaporated off under vacuum and the residue is diluted with ethyl acetate (300 mL) and 150 mL of water. The organic phase is washed with 100 mL of water, dried over magnesium sulfate and then concentrated to dryness under reduced pressure. The residue is purified by chromatography on silica gel, eluting at the start with a dichloromethane/methanol mixture (90/10 by volume). Ethyl 1-(1-ethoxyethyl)-3-[4-(4-methylpiperazin-1-yl)benzoylamino]-1H-thieno[2,3-c]pyrazole-5-carboxylate (4.05 g, 27%) is thus obtained in the form of a pale yellow oil, which product is used directly in the following step.

Ethyl 3-bromo-1-(1-ethoxyethyl)-1H-thieno[2,3-c]pyrazole-5-carboxylate is described in example 1.

N-(4-Chlorophenyl)-N-methylhydrazine

N'-Benzhydrylidene-N-(4-chlorophenyl)-N-methylhydrazine (1.5 g, 4.68 mmol) is placed in 20 mL of tetrahydrofuran with stirring. 5 mL of 5 N hydrochloric acid are added thereto and the solution is then left stirring at a temperature in the region of 50° C. for 16 hours. The aqueous phase is then neutralized with 5 N sodium hydroxide and is then extracted with ethyl acetate. The oil obtained after extraction is purified by chromatography on silica gel, eluting at the start with an ethyl acetate/heptane mixture (10/90 by volume). N-(4-Chlorophenyl)-N-methylhydrazine is thus obtained in the form of a pale yellow oil, 0.53 g (72%). (Rf=0.48. 20/80 EtOAc/heptane (v/v)).

N'-Benzhydrylidene-N-(4-chlorophenyl)-N-methylhydrazine

N-Benzhydrylidene-N'-(4-chlorophenyl)hydrazine (0.2 g, 0.65 mmol, 1 eq.) and 3.2 mL of tetrahydrofuran are placed in a predried 20 mL round-bottomed flask under argon. The solution is cooled to a temperature in the region of −10° C. and 0.5 M potassium hexamethylbis-silylamide solution (1.43 mL, 1.1 eq.) is then added. The solution darkens, and is left to react at this temperature for 30 minutes, followed by addition of a solution of methyl iodide in methyl tert-butyl ether (0.49 mL, 1.5 eq.). The mixture is then allowed to return to a temperature in the region of 25° C. and is left stirring for 4 hours. After treatment with sodium hydrogen carbonate, the mixture is extracted with ethyl acetate. The organic extracts are combined, dried over magnesium sulfate and then concentrated to dryness under vacuum. The residual oil is purified by chromatography on silica gel, eluting with an ethyl acetate/heptane mixture (10/90 by volume). N'-Benzhydrylidene-N-(4-chlorophenyl)-N-methylhydrazine is obtained in a yield of 96% in the form of a yellow solid, which product is used directly in the following step.

N-Benzhydrylidene-N'-(4-chlorophenyl)hydrazine 260 mL of 2-methyl-2-butanol are placed in a 500 mL round-bottomed flask, which is degassed with argon for 30 minutes. Once the degassing is complete, 60 mL of 2-methyl-2-butanol, palladium(II)diacetate (0.857 g, 1.27 mmol, 0.025 eq.) and the ligand MePHOS (0.928 g, 2.55 mmol, 0.05 eq.) are placed in a second dry round-bottomed flask under argon. The mixture is left stirring for 30 minutes at a temperature in the region of 25° C. Furthermore, 1,4-dichlorobenzene (7.49 g, 1 eq.) and sodium hydroxide powder (2.85 g, 1.4 eq.) are placed in the 500 mL round-bottomed flask. The catalyst is then transferred into the 500 mL round-bottomed flask, which is heated at a temperature in the region of 100° C. Finally, benzhydrylidenehydrazine (10 g, 50.9 mmol, 1 eq.) is added thereto. The resulting suspension is left stirring, and changes color quickly (dark red) until all of the halide has disappeared. The solvent is then evaporated to dryness and the residue is taken up in dichloromethane. The solid is filtered off through Celite® and then washed thoroughly with dichloromethane. The organic phase is washed with saturated ammonium chloride solution, dried over magnesium sulfate and then concentrated to dryness under vacuum. The residue is purified by chromatography on a column of silica gel, eluting at the start with an ethyl acetate/heptane mixture (10/90 by volume). N-Benzhydrylidene-N'-(4-chlorophenyl)hydrazine (85%) is thus obtained in the form of a yellow solid (Rf=0.35. EtOAc/Heptane 25/75 (v/v)).

4-(4-Methylpiperazin-1-yl)benzamide

4-Fluorobenzonitrile (12 g, 99 mmol, 1 eq.) and 100 mL of DMF are placed in a 250 mL round-bottomed flask. N-Methylpiperazine (16 mL, 1.6 eq., 123 mmol) is added to this solution. The orange solution is heated at a temperature in the region of 90° C. for 15 hours. The solvent is then evaporated to dryness and the residue is diluted with 500 mL of diethyl ether. The solution is washed with sodium hydrogen carbonate solution (2×100 mL) and then with saturated sodium chloride solution (100 mL). After evaporation, the 4-(4-methylpiperazin-1-yl)benzonitrile (orange solid, 10 g, 77%) is used without further purification in the following hydrolysis step. It is added at a temperature in the region of 0° C. to a solution of 98% sulfuric acid (25 mL) and 5 mL of water. The purple solution is then heated at a temperature in the region of 100° C. for 8 hours. The solution is cooled and then hydrolyzed by pouring onto ice. The pH is adjusted to 9-10 with sodium hydroxide pellets. The precipitate obtained is filtered off and washed thoroughly with water and then with tetrahydrofuran, which partially dissolves the product. The water is separated out by settling. After evaporating the organic phase to dryness, a solid is obtained, which is purified by chromatography on silica gel, eluting with a methanol/dichloromethane mixture (15/85 by volume). 4-(4-Methylpiperazin-1-yl)benzamide (8.7 g, 80%) is thus obtained in the form of a white solid, which is used directly in the following step.

EXAMPLE 29

Preparation of N-(2-methoxymethylpyrrolidin-1-yl)-3-[4-(4-methylpiperazin-1-yl)benzoylamino]-1H-thieno[2,3-c]pyrazole-5-carboxamide

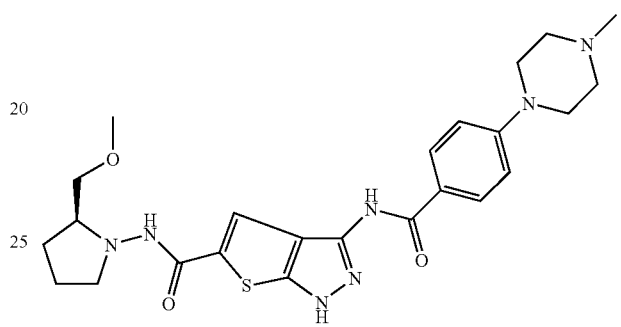

N-(2-Methoxymethylpyrrolidin-1-yl)-3-[4-(4-methylpiperazin-1-yl)benzoylamino]-1H-thieno[2,3-c]pyrazole-5-carboxamide is prepared according to example 28. LC/MS ethoxyethyl intermediate RT=2.62 min., M+H+ 571.1. M−H− 568.1; Final product: Yield=33%. MS: ES m/z=498 MH+ base peak. $^1$H NMR (400 MHz, (CD$_3$)$_2$SO-d$_6$, δ in ppm): 1.58 (m, 1H); from 1.70 to 1.87 (m, 2H); 2.00 (m, 1H); 2.25 (s, 3H); 2.48 (partially masked m, 4H); 2.86 (broad m, 1H); from 2.98 to 3.36 (broad multiplet, 3H); 3.21 (s, 3H); 3.32 (m, 4H); 3.46 (m, 1H); 6.98 (d, J=9.0 Hz, 2H); 7.96 (d, J=9.0 Hz, 2H); 8.05 (broad s, 1H).

EXAMPLE 30

Preparation of N-[5-(N'-benzyl-N'-methylhydrazinocarbonyl)-1H-thieno[2,3-c]pyrazol-3-yl]-4-(4-methylpiperazin-1-yl)benzamide

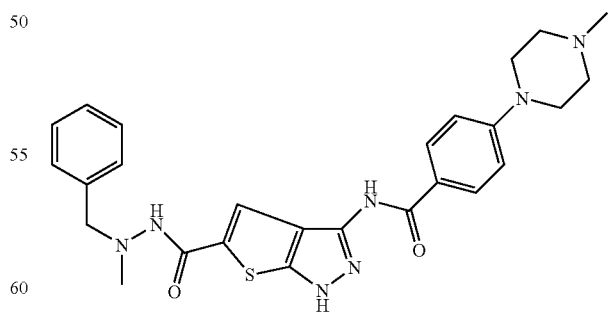

N-[5-(N'-Benzyl-N'-methylhydrazinocarbonyl)-1H-thieno[2,3-c]pyrazol-3-yl]-4-(4-methylpiperazin-1-yl)benzamide is prepared according to example 28. LC/MS ethoxyethyl intermediate RT=3.19 min., M+H+ 576.1. M−H− 574.2. Final product: Yield=16%. MS: ES m/z=504 MH+ base peak. ¹H NMR (400 MHz, (CD₃)₂SO-d₆, δ in ppm): the spectrum signals are broad, with a 60%-40% mixture of rotamers: 2.36 (s, 3H); from 2.54 to 2.72 (m, 7H); 3.36 (partially masked m, 4H); 3.89 (s, 1.2H); 3.98 (s, 0.8H); 7.02 (d, J=8.5 Hz, 2H); from 7.16 to 7.45 (m, 5H); 7.89 (s, 0.6H); 7.99 (d, J=8.5 Hz, 2H); 8.08 (s, 0.4H); 8.85 (s, 0.4H); 9.58 (s, 0.6H); 9.70 (broad multiplet, 0.4H); 10.7 (broad multiplet, 0.6H); 12.65 (broad multiplet, 0.4H); 12.85 (broad multiplet, 0.6H).

EXAMPLE 31

Preparation of N-(piperidin-1-yl)-3-[4-(4-methylpiperazin-1-yl)benzoylamino]-1H-thieno[2,3-c]pyrazole-5-carboxamide

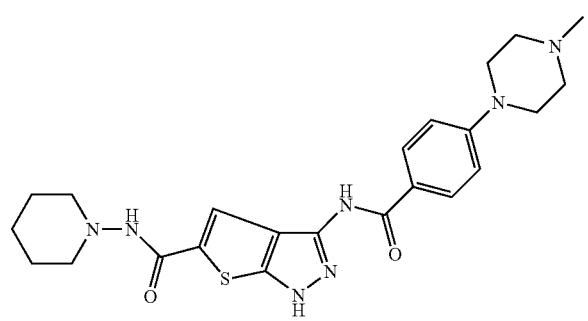

N-(Piperidin-1-yl)-3-[4-(4-methylpiperazin-1-yl)benzoylamino]-1H-thieno[2,3-c]-pyrazole-5-carboxamide is prepared according to example 28. LC/MS ethoxyethyl intermediate RT=2.97 min., M+H+ 540.4. M–H– 538.2. Final product: Yield=38%. MS: ES m/z=468 MH+ m/z=234.8 (M+2H)2+/2 base peak. ¹H NMR (400 MHz, (CD₃)₂SO-d₆, δ in ppm): 1.55 (broad m, 2H); 1.88 (broad m, 4H); 2.87 (s, 3H); from 3.05 to 3.21 (m, 4H); from 3.43 to 3.59 (m, 6H); from 4.02 to 4.10 (m, 2H); 7.10 (d, J=9.0 Hz, 2H); 8.04 (d, J=9.0 Hz, 2H); 8.27 (s, 1H).

EXAMPLE 32

Preparation of N-[5-(N'-benzylhydrazinocarbonyl)-1H-thieno[2,3-c]pyrazol-3-yl]-4-(4-methylpiperazin-1-yl)benzamide

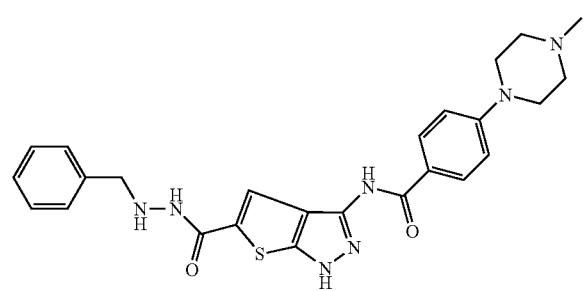

N-[5-(N'-Benzylhydrazinocarbonyl)-1H-thieno[2,3-c]pyrazol-3-yl]-4-(4-methylpiperazin-1-yl)benzamide is prepared according to example 28. LC/MS ethoxyethyl intermediate RT=3.10. MH+ 562.3. MH– 560.2. Final product: Yield=13%. MS: ES m/z=490 MH+ base peak. ¹H NMR (400 MHz, (CD₃)₂SO-d₆, δ in ppm): 2.23 (s, 3H); 2.44 (m, 4H); 3.30 (partially masked m, 4H); 3.97 (d, J=5.0 Hz, 2H); 5.37 (m, 1H); 7.00 (d, J=9.0 Hz, 2H); 7.25 (t, J=7.5 Hz, 1H); 7.33 (t, J=7.5 Hz, 2H); 7.38 (d, J=7.5 Hz, 2H); from 7.92 to 7.98 (m, 3H); 10.1 (d, J=5.0 Hz, 1H); 10.8 (very broad m, 1H); 12.9 (very broad m, 1H).

EXAMPLE 33

Preparation of N-[5-(N'-ethyl-N'-phenylhydrazinocarbonyl)-1H-thieno[2,3-c]pyrazol-3-yl]-4-(4-methylpiperazin-1-yl)benzamide

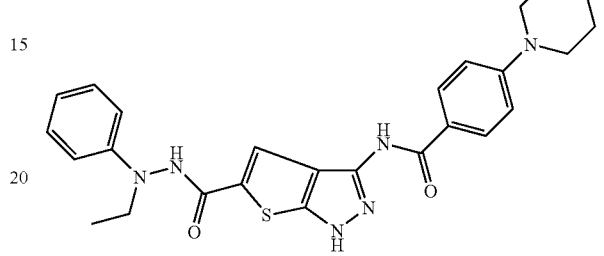

N-[5-(N'-Ethyl-N'-phenylhydrazinocarbonyl)-1H-thieno[2,3-c]pyrazol-3-yl]-4-(4-methylpiperazin-1-yl)benzamide is prepared according to example 28. LC/MS ethoxyethyl intermediate: RT=3.25 min., M+H+ 576.3. M–H– 574.1. Final product: Yield=28%. MS: ES m/z=504 MH+ base peak. ¹H NMR (400 MHz, (CD₃)₂SO-d₆, δ in ppm): 1.18 (t, J=7.0 Hz, 3H); 2.21 (s, 3H); 2.43 (m, 4H); 3.31 (partially masked m, 4H); 3.53 (q, J=7.0 Hz, 2H); 6.74 (t, J=7.5 Hz, 1H); 6.82 (d, J=7.5 Hz, 2H); 7.01 (broad d, J=8.5 Hz, 2H); 7.21 (t, J=7.5 Hz, 2H); 7.98 (broad d, J=8.5 Hz, 2H); 8.22 (s, 1H); 10.55 (s, 1H); 10.85 (broad multiplet, 1H); 12.9 (broad multiplet, 1H).

EXAMPLE 34

Preparation of N-[5-(N'-benzyl-N'-phenylhydrazinocarbonyl)-1H-thieno[2,3-c]pyrazol-3-yl]-4-(4-methylpiperazin-1-yl)benzamide

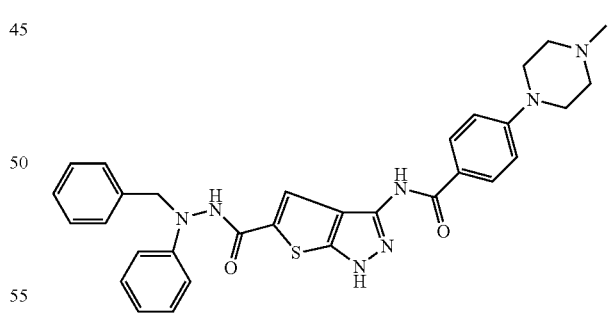

N-[5-(N'-Benzyl-N'-phenylhydrazinocarbonyl)-1H-thieno[2,3-c]pyrazol-3-yl]-4-(4-methylpiperazin-1-yl)benzamide is prepared according to example 28. LC/MS ethoxyethyl intermediate: RT=3.68 min., M+H+ 638.5. Final product: Yield=8%. MS: ES m/z=566 MH+ base peak. ¹H NMR (400 MHz, (CD₃)₂SO-d₆, δ in ppm): all the spectrum signals are broad, with 2.32 (s, 3H); 2.59 (m, 4H); 3.35 (partially masked m, 4H); 4.75 (s, 2H); 6.75 (t, J=7.5 Hz, 1H); 6.81 (d, J=8.5 Hz, 2H); 7.02 (d, J=8.5 Hz, 2H); from 7.11 to 7.38 (m, 5H); 7.49 (d, J=8.5 Hz, 2H); 7.98 (d, J=8.5 Hz, 2H); 8.17 (s, 1H); 10.8 (s, 1H); 10.9 (broad multiplet, 1H); 12.95 (broad multiplet, 1H).

EXAMPLE 35

Preparation of N-[5-(N'-methyl-N'-phenylhydrazinocarbonyl)-1H-thieno[2,3-c]pyrazol-3-yl]-4-(4-methylpiperazin-1-yl)benzamide

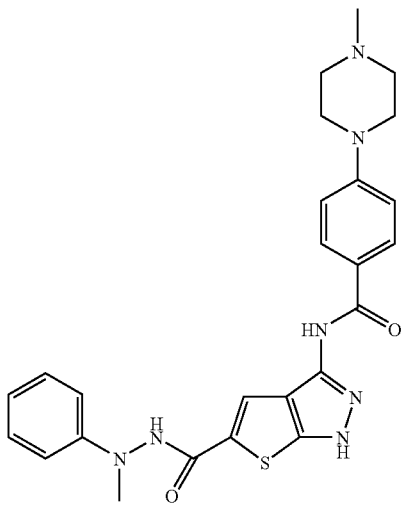

N-[5-(N'-Methyl-N'-phenylhydrazinocarbonyl)-1H-thieno[2,3-c]pyrazol-3-yl]-4-(4-methylpiperazin-1-yl)benzamide is prepared according to example 28. LC/MS ethoxyethyl intermediate: RT=2.74 min., M+H+ 561.0. Final product: Yield=22%. MS: ES m/z=490 MH+ base peak. $^1$H NMR (400 MHz, $(CD_3)_2SO$-$d_6$, δ in ppm): all the spectrum signals are broad, with 2.32 (s, 3H); 2.59 (m, 4H); 3.35 (partially masked m, 4H); 4.75 (s, 2H); 6.75 (t, J=7.5 Hz, 1H); 6.81 (d, J=8.5 Hz, 2H); 7.02 (d, J=8.5 Hz, 2H); from 7.11 to 7.38 (m, 5H); 7.49 (d, J=8.5 Hz, 2H); 7.98 (d, J=8.5 Hz, 2H); 8.17 (s, 1H); 10.8 (s, 1H); 10.9 (broad multiplet, 1H); 12.95 (broad multiplet, 1H).

EXAMPLE 36

Preparation of N-{5-[N'-(4-chlorophenyl)-N'-cyclobutylmethylhydrazinocarbonyl]-1H-thieno[2,3-c]pyrazol-3-yl}-4-(4-methylpiperazin-1-yl)-benzamide

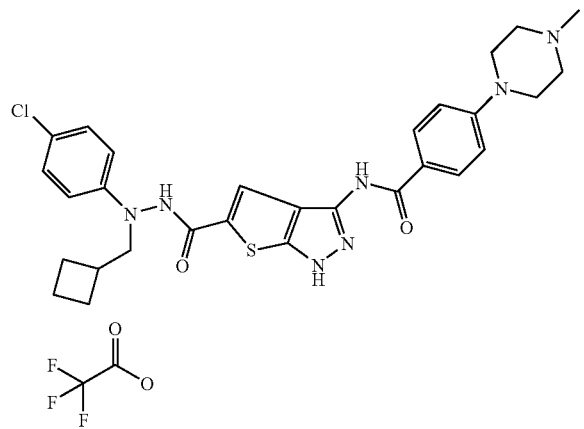

N-{5-[N'-(4-Chlorophenyl)-N'-cyclobutylmethylhydrazinocarbonyl]-1H-thieno[2,3-c]pyrazol-3-yl}-4-(4-methylpiperazin-1-yl)benzamide is prepared according to example 28. LC/MS ethoxyethyl intermediate: RT=4.20 min., M+H+ 650.1. M–H– 648.1. Final product: Yield=2%. MS: ES m/z=578 MH+ base peak. $^1$H NMR (400 MHz, $(CD_3)_2SO$-$d_6$, δ in ppm): from 1.71 to 1.88 (m, 3H); 2.03 (m, 1H); 2.63 (m, 1H); 2.85 (s, 3H); 3.14 (broad m, 4H); from 3.47 to 3.56 (partially masked m, 2H); 3.51 (d, J=7.0 Hz, 2H); 4.07 (broad m, 2H); 6.83 (d, J=9.0 Hz, 2H); 7.11 (d, J=9.0 Hz, 2H); 7.22 (d, J=9.0 Hz, 2H); 8.04 (d, J=9.0 Hz, 2H); 8.20 (s, 1H); 10.05 (broad multiplet, 1H); 10.6 (s, 1H); 10.95 (broad multiplet, 1H); 12.9 (broad multiplet, 1H).

N-(4-Chlorophenyl)-N-cyclobutylmethylhydrazine

N-(4-Chlorophenyl)-N-cyclobutylmethylhydrazine is prepared according to example 28.
Yield. (2 steps), 0.65 g (63%). Rf=0.43. (30/70 EtOAc/heptane (v/v)).

N'-Benzhydrylidene-N-(4-chlorophenyl)-N-cyclobutylmethylhydrazine

Rf=0.77. (30/70 EtOAc/heptane (v/v)) (immediate deprotection). N-Benzhydrylidene-N'-(4-chlorophenyl)hydrazine is described in example 28.

EXAMPLE 37

Preparation of N-{5-[N'-ethyl-N'-(4-fluorophenyl)hydrazinocarbonyl]-1H-thieno[2,3-c]pyrazol-3-yl}-4-(4-methylpiperazin-1-yl)benzamide

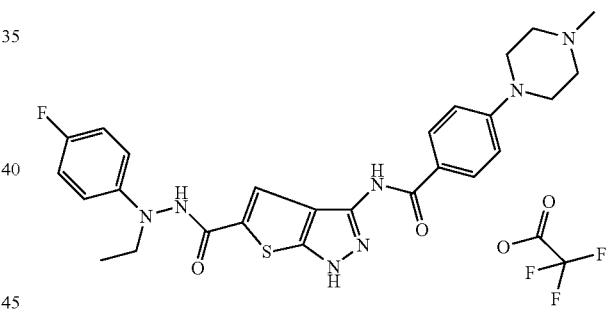

N-{5-[N'-Ethyl-N'-(4-fluorophenyl)hydrazinocarbonyl]-1H-thieno[2,3-c]pyrazol-3-yl}-4-(4-methylpiperazin-1-yl)benzamide is prepared according to example 28. LC/MS ethoxyethyl intermediate RT=3.20 min., M+H+ 594.2. M–H– 592.3. Final product: Yield=16%. MS: ES m/z=522 MH+ base peak. $^1$H NMR (400 MHz, $(CD_3)_2SO$-$d_6$, δ in ppm): observation of an 80%-20% mixture of rotamers: 1.16 (t, J=7.0 Hz, 2.4H); 1.31 (t, J=7.0 Hz, 0.6H); 2.87 (s, 3H); from 3.02 to 3.20 (m, 4H); from 3.35 to 3.59 (partially masked m, 2H); 3.50 (partially masked q, J=7.0 Hz, 1.6H); 4.08 (m, 2H); 4.30 (q, J=7.0 Hz, 0.4H); 6.83 (dd, J=4.5 and 9.0 Hz, 1.6H); from 7.00 to 7.17 (m, 4.4H); 8.03 (d, J=9.0 Hz, 2H); 8.17 (s, 0.2H); 8.21 (s, 0.8H); 9.67 (s, 0.2H); 9.77 (broad multiplet, 1H); 10.55 (s, 0.8H); 10.95 (m, 1H); 12.9 (very broad m, 1H).

N-Ethyl-N-(4-fluorophenyl)hydrazine

N-Ethyl-N-(4-fluorophenyl)hydrazine is prepared according to example 28.
Pale yellow oil, 0.32 g (30%).

N'-Benzhydrylidene-N-ethyl-N-(4-fluorophenyl) hydrazine

N'-Benzhydrylidene-N-ethyl-N-(4-fluorophenyl)hydrazine is prepared according to example 28.

Orange solid, 1.9 g (86%), Rf=0.64 (20/80 EtOAc/heptane (v/v)).

N-Benzhydrylidene-N'-(4-fluorophenyl)hydrazine

N-Benzhydrylidene-N'-(4-fluorophenyl)hydrazine is prepared according to example 28.

Yellow solid, yield 54% (Rf=0.33. 10/90 EtOAc/Heptane (v/v)), LC/MS MH+ 291.1. MH– 289.2.

EXAMPLE 38

Preparation of N-{5-[N'-(4-fluorophenyl)-N'-(2-methoxyethyl)-hydrazinocarbonyl]-1H-thieno[2,3-c]pyrazol-3-yl}-4-(4-methylpiperazin-1-yl)-benzamide

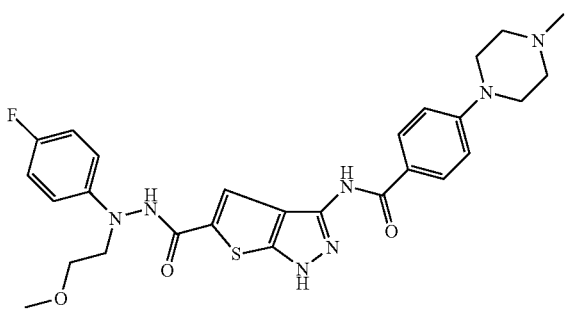

N-{5-[N'-(4-Fluorophenyl)-N'-(2-methoxyethyl)hydrazinocarbonyl]-1H-thieno[2,3-c]pyrazol-3-yl}-4-(4-methylpiperazin-1-yl)benzamide is prepared according to example 28. Yield=45%. MS: ES m/z=552 MH+ base peak. $^1$H NMR (400 MHz, $(CD_3)_2SO-d_6$, δ in ppm): 2.23 (s, 3H); 2.44 (m, 4H); 3.27 (s, 3H); from 3.28 to 3.31 (m, 4H); 3.58 (m, 2H); 3.64 (m, 2H); 6.83 (dd, J=4.5 and 9.0 Hz, 2H); from 6.98 to 7.06 (m, 4H); 7.98 (d, J=8.5 Hz, 2H); 8.21 (broad s, 1H); 10.7 (s, 1H); 10.9 (broad multiplet, 1H); 12.9 (broad multiplet, 1H).

N-(4-Fluorophenyl)-N-(2-methoxyethyl)hydrazine

N-(4-Fluorophenyl)-N-(2-methoxyethyl)hydrazine is prepared according to example 28.

0.57 g (60%). Rf=0.10 (20/80 EtOAc/heptane (v/v)), LC/MS RT=4.18. MH 183.3.

N'-Benzhydrylidene-N-(4-fluorophenyl)-N-(2-methoxyethyl)hydrazine

N'-Benzhydrylidene-N-(4-fluorophenyl)-N-(2-methoxyethyl)hydrazine is prepared according to example 28.

1.2 g (66%). Rf=0.26 (EtOAc/heptane 10/90 (v/v)). N-Benzhydrylidene-N'-(4-fluorophenyl)hydrazine is described in example 37.

EXAMPLE 39

Preparation of N-[5-(N'-ethyl-N'-o-tolylhydrazinocarbonyl)-1H-thieno[2,3-c]pyrazol-3-yl]-4-(4-methylpiperazin-1-yl)benzamide

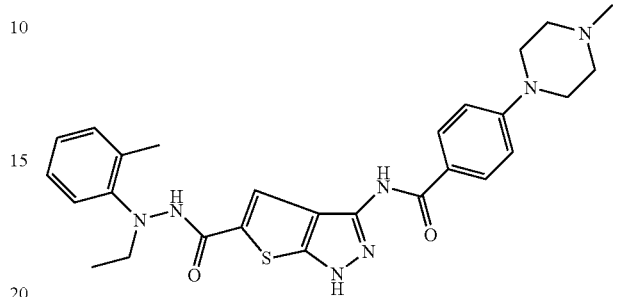

N-[5-(N'-Ethyl-N'-o-tolylhydrazinocarbonyl)-1H-thieno[2,3-c]pyrazol-3-yl]-4-(4-methylpiperazin-1-yl)benzamide is prepared according to example 28. Yield=14%; MS: ES m/z=518 MH+ base peak. $^1$H NMR (400 MHz, $(CD_3)_2SO-d_6$, δ in ppm): 1.15 (t, J=7.0 Hz, 3H); 2.23 (s, 3H); 2.29 (s, 3H); 2.44 (m, 4H); from 3.23 to 3.33 (partially masked m, 6H); 6.96 (t, J=7.5 Hz, 1H); 7.00 (d, J=9.0 Hz, 2H); from 7.12 to 7.17 (m, 2H); 7.29 (d, J=8.0 Hz, 1H); 7.98 (d, J=8.5 Hz, 2H); 8.12 (s, 1H); 10.2 (s, 1H); 11.0 (broad multiplet, 1H); 12.9 (very broad m, 1H).

EXAMPLE 40

Preparation of N-[5-(N'-ethyl-N'-m-tolylhydrazinocarbonyl)-1H-thieno[2,3-c]pyrazol-3-yl]-4-(4-methylpiperazin-1-yl)benzamide

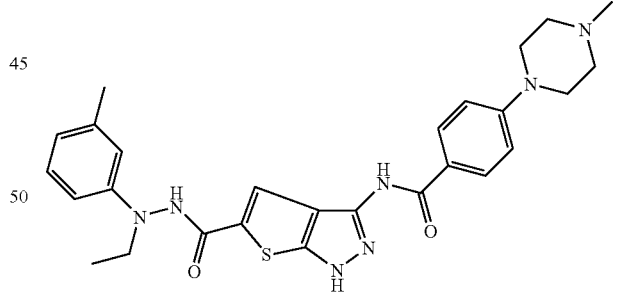

N-[5-(N'-Ethyl-N'-m-tolylhydrazinocarbonyl)-1H-thieno[2,3-c]pyrazol-3-yl]-4-(4-methylpiperazin-1-yl)benzamide is prepared according to example 28. Yield=18%. MS: ES m/z=518 MH+ base peak. $^1$H NMR (400 MHz, $(CD_3)_2SO-d_6$, δ in ppm): observation of an 80%-20% mixture of rotamers: 1.16 (t, J=7.0 Hz, 3H); 2.22 (s, 3H); 2.24 (s, 2.4H); 2.28 (s, 0.6H); 2.44 (m, 4H); from 3.25 to 3.35 (masked m, 4H); 3.52 (q, J=7.0 Hz, 2H); 6.57 (d, J=7.5 Hz, 0.8H); from 6.59 to 6.66 (m, 1.6H); 6.73 (d, J=7.5 Hz, 0.2H); from 6.81 to 6.87 (m, 0.4H); 7.00 (d, J=9.0 Hz, 2H); 7.08 (t, J=7.5 Hz, 0.8H); 7.17 (t, J=7.5 Hz, 0.2H); 7.99 (d, J=9.0 Hz, 2H); 8.16 (s, 0.2H);

8.22 (0.8H); 9.62 (broad multiplet, 0.2H); 10.5 (s, 0.8H); 11.1 (broad multiplet, 1H); 12.9 (broad multiplet, 1H).

EXAMPLE 41

Preparation of N-[5-(N'-ethyl-N'-m-tolylhydrazinocarbonyl)-1H-thieno[2,3-c]pyrazol-3-yl]-4-(4-methylpiperazin-1-yl)benzamide

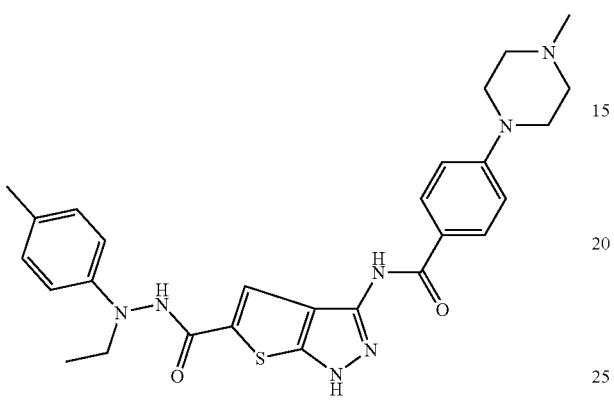

N-[5-(N'-Ethyl-N'-m-tolylhydrazinocarbonyl)-1H-thieno[2,3-c]pyrazol-3-yl]-4-(4-methylpiperazin-1-yl)benzamide is prepared according to example 28. Yield=3%. MS: ES m/z=518 MH+ base peak. $^1$H NMR (400 MHz, $(CD_3)_2SO$-$d_6$, δ in ppm): 1.15 (t, J=7.0 Hz, 3H); 2.20 (s, 3H); 2.23 (s, 3H); 2.45 (m, 4H); from 3.20 to 3.41 (masked m, 4H); 3.49 (q, J=7.0 Hz, 2H); 6.73 (d, J=9.0 Hz, 2H); from 6.96 to 7.04 (m, 4H); 7.99 (d, J=9.0 Hz, 2H); 8.21 (s, 1H); 10.45 (s, 1H); 11.25 (broad multiplet, 1H); 13.1 (broad multiplet, 1H).

EXAMPLE 42

Preparation of N-{5-[N'-(4-fluorophenyl)-N'-isobutylhydrazinocarbonyl]-1H-thieno[2,3-c]pyrazol-3-yl}-4-(4-methylpiperazin-1-yl)benzamide

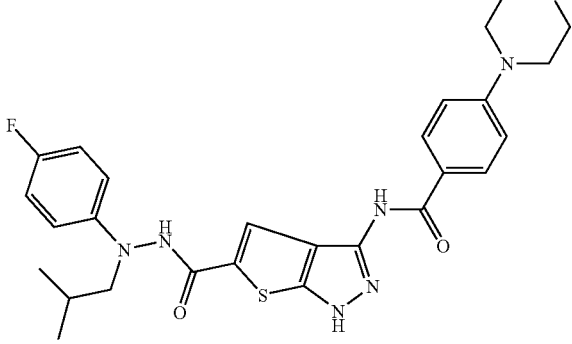

N-{5-[N'-(4-Fluorophenyl)-N'-isobutylhydrazinocarbonyl]-1H-thieno[2,3-c]pyrazol-3-yl}-4-(4-methylpiperazin-1-yl)benzamide is prepared according to example 28. Yield=59%, MS: ES m/z=550 MH+ base peak. $^1$H NMR (400 MHz, $(CD_3)_2SO$-$d_6$, δ in ppm): 0.97 (d, J=6.5 Hz, 6H); 1.91 (m, 1H); 2.22 (s, 3H); 2.44 (m, 4H); from 3.24 to 3.34 (partially masked m, 6H); 6.81 (dd, J=4.5 and 9.0 Hz, 2H); from 6.98 to 7.06 (m, 4H); 7.98 (d, J=9.0 Hz, 2H); 8.21 (s, 1H); 10.6 (s, 1H); 11.0 (broad multiplet, 1H); 13.0 (broad multiplet, 1H).

N-(4-Fluorophenyl)-N-isobutylhydrazine

N-(4-Fluorophenyl)-N-isobutylhydrazine is prepared according to example 28.

Colorless oil, 0.62 g (82%). Rf=0.34 (20/80 EtOAc/heptane (v/v)), LC/MS RT=2.48 min.

N'-Benzhydrylidene-N-(4-fluorophenyl)-N-isobutylhydrazine

N'-Benzhydrylidene-N-(4-fluorophenyl)-N-isobutylhydrazine is prepared according to example 28.

Yellow solid, 1.51 g (44%). Rf=0.52 (3/97 acetone/heptane (v/v)), LC/MS RT=6.03 min., no ionization. N-Benzhydrylidene-N'-(4-fluorophenyl)hydrazine is described in example 37.

EXAMPLE 43

Preparation of N-{5-[N'-(3-bromophenyl)-N'-ethylhydrazinocarbonyl]-1H-thieno[2,3-c]pyrazol-3-yl}-4-(4-methylpiperazin-1-yl)benzamide

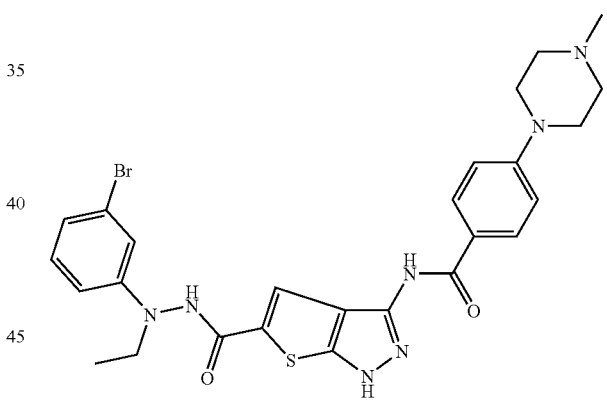

N-{5-[N'-(3-Bromophenyl)-N'-ethylhydrazinocarbonyl]-1H-thieno[2,3-c]pyrazol-3-yl}-4-(4-methylpiperazin-1-yl)benzamide is prepared according to example 28. Yield=5%. MS: ES m/z=582 MH+ base peak. $^1$H NMR (400 MHz, $(CD_3)_2SO$-$d_6$, δ in ppm): 1.16 (t, J=7.0 Hz, 3H); 2.22 (s, 3H); 2.44 (m, 4H); from 3.26 to 3.34 (partially masked m, 4H); 3.54 (q, J=7.0 Hz, 2H); 6.82 (dd, J=2.0 and 8.0 Hz, 1H); 6.89 (dd, J=2.0 and 8.0 Hz, 1H); 6.92 (t, J=2.5 Hz, 1H); 7.01 (d, J=9.0 Hz, 2H); 7.16 (t, J=8.5 Hz, 1H); 7.98 (d, J=9.0 Hz, 2H); 8.24 (s, 1H); 10.7 (s, 1H); 10.95 (broad multiplet, 1H); 12.95 (broad multiplet, 1H).

N-(3-Bromophenyl)-N-ethylhydrazine

N-(3-Bromophenyl)-N-ethylhydrazine is prepared according to example 28.

Colorless oil, 2.80 g, quantitative. LC/MS RT=2.70.

N'-Benzhydrylidene-N-(3-bromophenyl)-N-ethylhydrazine

N'-Benzhydrylidene-N-(3-bromophenyl)-N-ethylhydrazine is prepared according to example 28.

Orange solid, 13.5 g (80%). Rf=0.46 (3/97 Et$_2$O/heptane (v/v)).

N-Benzhydrylidene-N'-(3-bromophenyl)hydrazine (3-Bromophenyl)hydrazine hydrochloride (10 g, 44 mmol, 1 eq.), benzophenone (8.14 g, 44 mmol, 1 eq.) and ethanol (100 mL) are placed in a 250 mL round-bottomed flask. 2 mL of concentrated sulfuric acid are then added. The resulting suspension is heated at a temperature in the region of 80° C. After 30 minutes at this temperature, the suspension becomes a solution. The solution is stirred at this temperature for 18 hours, and is then concentrated to 95%. The residue is diluted with ethyl acetate and washed with sodium hydrogen carbonate solution. After drying over magnesium sulfate, the solution is concentrated and the residue is purified by chromatography on a column of silica gel, eluting with an ether/heptane mixture (3/97 by volume). 15 g (95%) of N-benzhydrylidene-N'-(3-bromophenyl)hydrazine are thus obtained.

EXAMPLE 44

Preparation of 6-(4-methyl[1,4]diazepan-1-yl)-N-[5-(N'-methyl-N'-phenylhydrazinocarbonyl)-1H-thieno[2,3-c]pyrazol-3-yl]nicotinamide

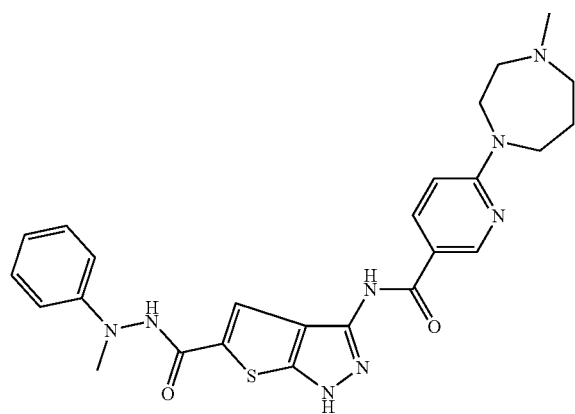

6-(4-Methyl[1,4]diazepan-1-yl)-N-[5-(N'-methyl-N'-phenylhydrazinocarbonyl)-1H-thieno[2,3-c]pyrazol-3-yl]nicotinamide is prepared according to example 28. MS: ES m/z=505 MH+ base peak. $^1$H NMR (400 MHz, (CD$_3$)$_2$SO-d$_6$, δ in ppm): 1.89 (m, 2H); 2.26 (s, 3H); 2.47 (partially masked m, 2H); 2.61 (m, 2H); 3.17 (s, 3H); 3.67 (t, J=6.0 Hz, 2H); 3.80 (m, 2H); 6.71 (d, J=9.0 Hz, 1H); 6.76 (t, J=7.5 Hz, 1H); 6.82 (d, J=8.0 Hz, 2H); 7.22 (m, 2H); 8.15 (partially masked dd, J=2.5 and 9.0 Hz, 1H); 8.16 (s, 1H); 8.80 (d, J=2.5 Hz, 1H); 10.75 (s, 1H); 11.0 (broad multiplet, 1H); 12.9 (broad m, 1H).

4-(4-Methyl[1,4]diazepan-1-yl)benzamide

4-Fluorobenzonitrile (5 g, 41 mmol, 1 eq.) and 35 mL of dimethylformamide are placed in a 100 mL round-bottomed flask. N-Methylhomopiperazine (5.18 g, 45 mmol, 1.1 eq.) is added to this solution. The solution is heated at a temperature in the region of 90° C. for 36 hours and the solvent is then evaporated to dryness. The residue is diluted with 150 mL of ethyl acetate and 30 mL of water. The aqueous phase is extracted with ethyl acetate and the combined organic phases are dried over magnesium sulfate. After evaporation, the residual oil is purified by chromatography on a column of silica gel, eluting with a 0-10% methanol/dichloromethane gradient (Rf=0.2, 10/90 methanol/dichloromethane (v/v)). The 4-(4-methyl[1,4]diazepan-1-yl)benzonitrile (yellow solid) is placed directly in a mixture of 20 mL of 98% sulfuric acid and 2 mL of water. This orange solution is heated at a temperature in the region of 100° C. for 18 hours, and then cooled and hydrolyzed by pouring it onto ice. The pH is adjusted to 9-10 with sodium hydroxide pellets. The yellow precipitate obtained is filtered off and washed thoroughly with water and then dried under vacuum. 4-(4-Methyl[1,4]diazepan-1-yl)benzamide (3.7 g, 38%) is thus obtained in the form of a yellow solid, which is used directly in the following step.

EXAMPLE 45

Preparation of N-[5-(benzylidenehydrazinocarbonyl)-1H-thieno-[2,3-c]pyrazol-3-yl]-4-(4-methylpiperazin-1-yl)benzamide

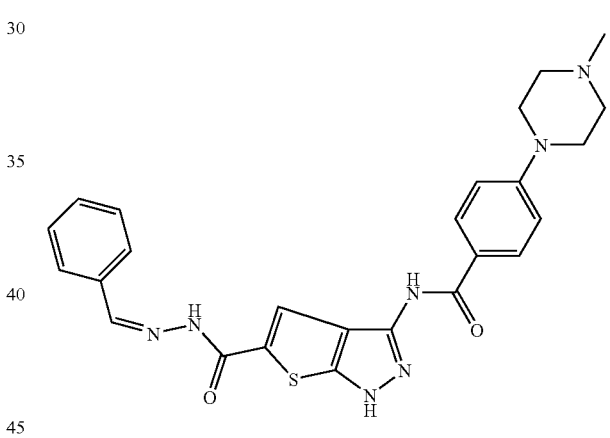

N-(5-Hydrazinocarbonyl-1H-thieno[2,3-c]pyrazol-3-yl)-4-(4-methylpiperazin-1-yl)-benzamide (0.150 g, 0.318 mmol, 1 eq.), ethanol (1 mL) and, by syringe, benzaldehyde (0.048 mL, 0.47 mmol, 1.3 eq.) are placed in a dry 5 mL round-bottomed flask under argon. Two drops of 5 N hydrochloric acid are added to the suspension. The reaction mixture is stirred at a temperature in the region of 50° C. for 3 hours, the solvent is then evaporated off and the residue is placed directly on a column of neutralized silica gel. Elution is performed with a methanol/dichloromethane mixture (10/90 by volume). The product obtained is directly added to a mixture of 1 mL of tetrahydrofuran and 0.5 mL of 5 N hydrochloric acid. The precipitate obtained is filtered off, washed with water and dried. N-[5-(Benzylidenehydrazinocarbonyl)-1H-thieno[2,3-c]pyrazol-3-yl]-4-(4-methylpiperazin-1-yl)benzamide is obtained in the form of a white solid (0.029 g, 16%). MS: ES m/z=488 MH+ base peak. $^1$H NMR (400 MHz, (CD$_3$)$_2$SO-d$_6$, δ in ppm): 2.53 (partially masked s, 3H); 2.87 (m, 4H); 3.47 (m, 4H); 7.03 (d, J=9.0 Hz, 2H); from 7.39 to 7.49 (m, 3H); 7.79 (d, J=7.5 Hz, 2H); 8.01 (d, J=9.0 Hz, 2H); 8.28 (s, 1H); 8.39 (s, 1H).

N-(5-Hydrazinocarbonyl-1H-thieno[2,3-c]pyrazol-3-yl)-4-(4-methylpiperazin-1-yl)benzamide Ethyl 3-[4-(4-methylpiperazin-1-yl)benzoylamino]-1H-thieno[2,3-c]pyrazole-5-carboxylate (0.5 g, 1.03 mmol, 1 eq.) and ethanol (2 mL) are placed in a 15 mL round-bottomed flask, and a 1 M hydrazine solution (3.09 mL, 3.09 mmol) and 2 mL of hydrazine monohydrate are added. The reaction mixture is stirred at reflux for 5 hours, the solvent is then evaporated off and the residue is taken up in water. The white precipitate is filtered off, washed with water and then dried at a temperature in the region of 80° C. under vacuum. N-(5-Hydrazinocarbonyl-1H-thieno[2,3-c]pyrazol-3-yl)-4-(4-methylpiperazin-1-yl)benzamide (0.15 g, 49%), Rf=0.32 (methanol/dichloromethane 10/90 (v/v)) is thus obtained, which product is used directly in the following step. Ethyl 3-[4-(4-methylpiperazin-1-yl)benzoylamino]-1H-thieno[2,3-c]pyrazole-5-carboxylate may be obtained by deprotection of ethyl 1-(1-ethoxyethyl)-3-[4-(4-methylpiperazin-1-yl)benzoylamino]-1H-thieno[2,3-c]pyrazole-5-carboxylate according to example 28.

EXAMPLE 46

Preparation of N-[5-(N'-methyl-N'-phenylhydrazinocarbonyl)-1H-thieno[2,3-c]pyrazol-3-yl]-4-(2-morpholin-4-ylethoxy)benzamide

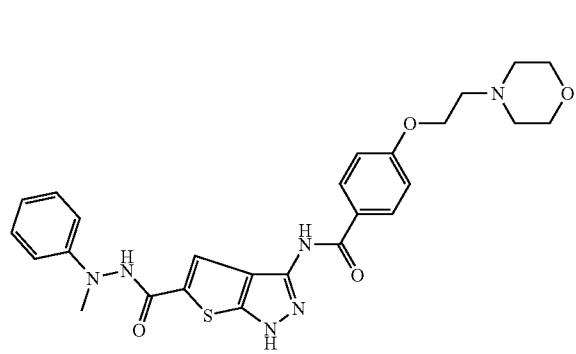

N-[5-(N'-Methyl-N'-phenylhydrazinocarbonyl)-1H-thieno[2,3-c]pyrazol-3-yl]-4-(2-morpholin-4-ylethoxy)benzamide is prepared according to example 28. (Ethoxyethyl intermediate: LC/MS RT=3.10 min., MH+ 593.5). Purification of the intermediate is performed on silica gel, eluting with a methanol/dichloromethane mixture (10/90 by volume). The treatment of the deprotection step is performed in the following manner: the reaction mixture is treated with water and then extracted with 5 mL of ethyl acetate. The aqueous phase is basified with 5 N sodium hydroxide and then extracted again with ethyl acetate (2×5 mL). This organic phase is dried over magnesium sulfate and then concentrated to dryness. The yellow solid obtained is triturated with heptane. After filtering off the solid, it is dried under vacuum to give N-[5-(N'-methyl-N'-phenylhydrazinocarbonyl)-1H-thieno[2,3-c]pyrazol-3-yl]-4-(2-morpholin-4-ylethoxy)benzamide, 0.192 g (40% for two steps). MS: ES m/z=521 MH+ base peak. $^1$H NMR (400 MHz, (CD$_3$)$_2$SO-d$_6$, δ in ppm): 2.48 (partially masked m, 4H); 2.72 (t, J=6.0 Hz, 2H); 3.17 (s, 3H); 3.58 (m, 4H); 4.18 (t, J=6.0 Hz, 2H); 6.76 (t, J=7.5 Hz, 1H); 6.82 (d, J=8.5 Hz, 2H); from 7.00 to 7.10 (m, 3H); 7.22 (broad t, J=8.0 Hz, 2H); 8.05 (broad d, J=8.5 Hz, 2H); 8.16 (broad s, 1H); 10.75 (broad s, 1H); 10.9 (very broad m, 1H); 12.9 (very broad m, 1H).

4-(2-Morpholin-4-ylethoxy)benzamide

Potassium carbonate (15.1 g, 109 mmol, 3 eq.), acetonitrile (73 mL) and then 4-hydroxybenzamide (5 g, 36.5 mmol, 1 eq.) are placed in a 250 mL round-bottomed flask. The suspension is stirred for 30 minutes, followed by addition of 4-(2-chloroethyl)morpholine hydrochloride (8.82 g, 47 mmol, 1.3 eq.). 10 mL of dimethylformamide are added to this suspension, and the mixture is then stirred at a temperature in the region of 40° C. for 16 hours. The solvent is then evaporated off and the residue is diluted with water and extracted with dichloromethane. The aqueous phase is acidified with 5 N hydrochloric acid and reextracted with dichloromethane. The organic phases are combined, dried over magnesium sulfate and then concentrated to dryness under vacuum. 4-(2-Morpholin-4-ylethoxy)benzamide 2.17 g (23%) is thus obtained in the form of a white solid, which is used directly in the following step.

EXAMPLE 47

Preparation of 4-(4-methyl[1,4]diazepan-1-yl)-N-[5-(N'-methyl-N'-phenylhydrazinocarbonyl)-1H-thieno[2,3-c]pyrazol-3-yl]benzamide

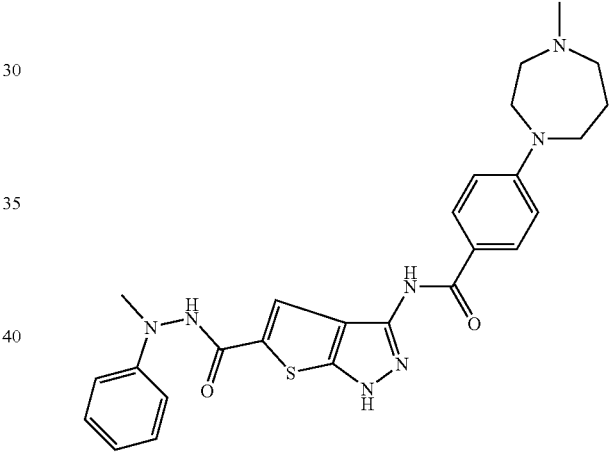

4-(4-Methyl[1,4]diazepan-1-yl)-N-[5-(N'-methyl-N'-phenylhydrazinocarbonyl)-1H-thieno[2,3-c]pyrazol-3-yl]benzamide is prepared according to example 28. MS: EI m/z=503 M+. m/z=382 (M−C$_7$H$_9$N$_2$)+m/z=217 C$_{12}$H$_{15}$N$_3$O+. base peak. $^1$H NMR (400 MHz, (CD$_3$)$_2$SO-d$_6$, δ in ppm): 1.90 (m, 2H); 2.26 (s, 3H); 2.45 (m, 2H); 2.62 (m, 2H); 3.17 (s, 3H); 3.52 (t, J=6.0 Hz, 2H); 3.59 (m, 2H); from 6.73 to 6.79 (m, 3H); 6.82 (d, J=8.5 Hz, 2H); 7.21 (t, J=7.5 Hz, 2H); 7.94 (d, J=8.5 Hz, 2H); 8.16 (s, 1H); 10.7 (s, 1H); 10.8 (broad multiplet, 1H); 12.9 (broad multiplet, 1H). 4-(4-Methyl[1,4]diazepan-1-yl)benzamide is described in example 44.

LC/MS Analyses:

The LC/MS analyses were performed on an LCT Micromass machine connected to an HP 1100 machine. The abundance of the products was measured using an HP G1315A diode array detector over a wavelength range of 200-600 nm and a Sedex 65 light scattering detector. The mass spectra were acquired over a range from 180 to 800 atomic mass units. The data were analyzed using the Micromass MassLynx software. The separation was performed on a Thermo Hypersil Gold C18 3 µm (50×3 mm) column, eluting with a linear gradient of 5% to 95% acetonitrile containing 0.1% (v/v) of formic acid in water containing 0.1% (v/v) of formic acid, over 5 minutes at a flow rate of 0.8 ml/minute. The total analysis time, including the column reequilibration period, is 7 minutes. The mass spectra were acquired in electrospray (ES$^+$/ES$^-$) mode on a Platform II (Micromass) machine. The main ions observed are described.

Purification by LC/MS:

The products may be purified by LC/MS using a Waters FractionsLynx system composed of a Waters 600 gradient pump, a Waters 515 regeneration pump, a Waters Reagent Manager dilution pump, a Waters 2700 auto-injector, two Rheodyne LabPro valves, a Waters 996 diode array detector, a Waters ZMD mass spectrometer and a Gilson 204 fraction collector. The system is controlled by the Waters FractionLynx software. Before purification, the samples are prepared in the following manner: each sample is dissolved in dimethyl sulfoxide to a concentration in the region of 60 mg/mL and injected at a rate of 1 mL per injection.

Method A: The separation was performed alternately on two Waters Symmetry ($C_{18}$, 5 µM, 19×50 mm) columns, one column undergoing regeneration with a 95/5 (v/v) water/acetonitrile mixture containing 0.07% (v/v) of trifluoroacetic acid, while the other column was being used for separation. The columns were eluted using a linear gradient over 11 minutes of 20% to 95% acetonitrile containing 0.07% (v/v) of trifluoroacetic acid in water containing 0.07% (v/v) of trifluoroacetic acid, at a flow rate of 10 ml/minute. On leaving the separation column, the flow of solvent is divided by an LC Packing Accurate machine: one thousandth of the effluent diluted with methanol at a flow rate of 0.5 ml/minute is conveyed to the detectors, in a proportion of 75% to the diode array detector and the remaining 25% to the mass spectrometer. The rest of the effluent (999/1000) is conveyed to the fraction collector, where the flow is discarded if the mass of the expected product is not detected by the FractionLynx software. The molecular formulae of the expected products are supplied to the FractionLynx software, which triggers the collection of the product when the mass signal detected corresponds to the [M+H]$^+$ ion and/or to the [M+Na]$^+$ ion. In certain cases, depending on the analytical LC/MS results, when an intense ion corresponding to [M+2H]$^{++}$ was detected, the value corresponding to half the calculated molecular mass (MW/2) is also supplied to the FractionLynx software. Under these conditions, collection is also triggered when the mass signal of the [M+2H]$^{++}$ and/or [M+Na+H]$^{++}$ ion is detected. The products were collected in tared glass tubes. After collection, the solvents were evaporated off, in a Savant AES 2000 or Genevac HT8 centrifugal evaporator and the masses of the products were determined by weighing the tubes after evaporation of the solvents. Alternatively, the solvents are evaporated to dryness in a rotary evaporator under vacuum (2 kPa) at a temperature in the region of 40° C. Each product obtained is analyzed by LC/MS.

Method A': The separation is performed in the same manner as for method A, and the columns are eluted with a linear gradient over 11 minutes of from 5% to 95% acetonitrile containing 0.07% (v/v) of trifluoroacetic acid in water containing 0.07% (v/v) of trifluoroacetic acid, at a flow rate of 10 mL/minute.

Method B: The separation is performed on a Waters SunFire column ($C_{18}$, 5 µM, 30×100 mm). The elution is performed using a linear gradient over 11 minutes of from 5% to 95% acetonitrile containing 0.07% (v/v) of trifluoroacetic acid in water containing 0.07% (v/v) of trifluoroacetic acid, at a flow rate of 30 mL/minute. On leaving the separation column, the flow of solvent is divided by an LC Packing accurate system: one ten-thousandth of the effluent diluted with methanol at a flow rate of 1 mL/minute is conveyed to the detectors, in a proportion of 75% to the diode array detector, and the remaining 25% to the mass spectrometer. The rest of the effluent (9999/10000) is conveyed to the fraction collector, where the flow is discarded so long as the mass of the expected product is not detected by the FractionLynx software. The molecular formulae of the expected products are given to the FractionLynx software, which initiates collection of the product when the detected mass signal corresponds to the ion [M+H]$^+$ and/or [M+Na]$^+$. In certain cases, dependent on the analytical LC/MS results, when an intense ion corresponding to [M+2H]$^{++}$ was detected, the value corresponding to half the calculated molecular mass (MW/2) is also given to the FractionLynx software. Under these conditions, collection is also initiated when the mass signal of the ion [M+2H]$^{++}$ and/or [M+Na+H]$^{++}$ is detected. The products are collected in glass tubes. After collection, the solvents are evaporated off, on a Jouan RC1010 centrifugal evaporator. Alternatively, the solvents are evaporated to dryness on a rotary evaporator under vacuum (2 kPa) at a temperature in the region of 40° C. Each product obtained is analyzed by LC/MS.

The dry residues are taken up in methanol and evaporated again to give dry products in powder form.

Method B': The separation is performed in the same manner as for method B, and the columns are eluted with a linear gradient over 11 minutes of from 10% to 95% acetonitrile containing 0.07% (v/v) of trifluoroacetic acid in water containing 0.07% (v/v) of trifluoroacetic acid, at a flow rate of 30 mL/minute.

The products according to the invention may be in achiral form, or racemic form, or in the form enriched in one stereoisomer, or enriched in one enantiomer; and may optionally be salified.

A product in accordance with the invention may be used for the manufacture of a medicament that is useful for treating a pathological condition, in particular a cancer.

The present invention also relates to therapeutic compositions comprising a compound according to the invention, in combination with a pharmaceutically acceptable excipient according to the chosen mode of administration. The pharmaceutical composition may be in solid or liquid form or in the form of liposomes.

Among the solid compositions that may be mentioned are powders, gel capsules and tablets. Among the oral forms that may also be included are solid forms protected with respect to the acidic medium of the stomach. The supports used for the solid forms consist especially of mineral supports, for instance phosphates or carbonates, or organic supports, for instance lactose, celluloses, starch or polymers. The liquid forms consist of solutions, suspensions or dispersions. They contain as dispersive support either water or an organic solvent (ethanol, NMP or the like) or mixtures of surfactants and of solvents, or of complexing agents and of solvents.

The liquid forms will preferably be injectable and, as a result, will have a formulation that is acceptable for such a use.

Routes of administration that are acceptable by injection include intravenous, intraperitoneal, intramuscular and subcutaneous routes, the intravenous route being preferred.

The administered dose of the compounds of the invention will be adapted by the practitioner as a function of the route of administration to the patient and of the patient's condition.

The compounds of the present invention may be administered alone or as a mixture with other anticancer agents. Among the possible combinations that may be mentioned are:

- alkylating agents and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine
- platinum derivatives such as, especially, cisplatin, carboplatin or oxaliplatin
- antibiotics such as, especially, bleomycin, mitomycin or dactinomycin
- antimicrotubule agents such as, especially, vinblastine, vincristine, vindesine, vinorelbine and taxoids (paclitaxel and docetaxel)
- anthracyclines such as, especially, doxorubicin, daunorubicin, idarubicin, epirubicin, mitoxantrone and losoxantrone
- group I and II topoisomerase inhibitors such as etoposide, teniposide, amsacrine, irinotecan, topotecan and tomudex
- fluoropyrimidines such as 5-fluorouracil, UFT and floxuridine
- cytidine analogs such as 5-azacytidine, cytarabine, gemcitabine, 6-mercaptomurine and 6-thioguanine
- adenosine analogs such as pentostatin, cytarabine or fludarabine phosphate
- methotrexate and folinic acid
- various enzymes and compounds such as L-asparaginase, hydroxyurea, trans-retinoic acid, suramine, dexrazoxane, amifostine and herceptin, and also estrogen-based and androgenic hormones
- antivascular agents such as combretastatin derivatives or colchicine derivatives, and prodrugs thereof.

It is also possible to combine the compounds of the present invention with a radiation treatment. These treatments may be administered simultaneously, separately or sequentially. The treatment will be adapted by the practitioner as a function of the patient to be treated.

The progress of the cell cycle is often governed by cycline-dependent kinases (CDK), which are activated by an interaction with proteins belonging to the cycline family, this activation ending in the phosphorylation of substrates and finally in cell division. In addition, the endogenous inhibitors of the CDKs that are activated (family of INK4 and of KIP/CIP) negatively regulate the activity of CDKs. The growth of normal cells is due to a balance between the CDK activators (cyclines) and the endogenous inhibitors of CDKs. In several types of cancer, the aberrant expression or activity of several of these cell cycle regulators has been described.

Cycline E activates the kinase Cdk2, which then acts to phosphorylate the protein pRb (retinoblastoma protein) resulting in an irreversible engagement in cell division and transition to the S phase (PL Toogood, Medicinal Research Reviews (2001), 21(6); 487-498). The kinase CDK2 and possibly CDK3 are necessary for progress into the G1 phase and entry into the S phase. During the formation of a complex with cycline E, they maintain the hyperphosphorylation of pRb to aid the progress from the G1 phase to the S phase. In complexes with cycline A, CDK2 plays a role in inactivating E2F and is necessary for achieving the S phase (T D. Davies et al. (2001) Structure 9, 389-3).

The CDK1/cycline B complex regulates the progress of the cell cycle between the G2 phase and the M phase. Negative regulation of the CDK/cycline B complex prevents normal cells from entering the S phase before the G2 phase has been correctly and completely terminated (K. K. Roy and E. A. Sausville, Current Pharmaceutical Design, 2001, 7, 1669-1687).

A level of regulation of the activity of CDKs exists. The cycline-dependent activators of kinases (CAK) have a positive action on regulating CDKs. CAK phosphorylates CDKs on the threonine residue to make the target enzyme totally active.

The presence of defects in the molecules involved in the cell cycle results in activation of the CDKs and progression of the cycle; it is normal to wish to inhibit the activity of the CDK enzymes in order to block the cell growth of cancer cells.

Many proteins involved in chromosome segregation and spindle assembly have been identified in yeast and *drosophila*. Disorganization of these proteins leads to the non-segregation of the chromosomes and to monopolar or disorganized spindles. Among these proteins, certain kinases, including Aurora and Ipl1, originating, respectively, from *drosophila* and from *S. cerevisiae*, are necessary for chromosome segregation and separation of the centrosome. A human analog of yeast Ipl1 has recently been cloned and characterized by various laboratories. This kinase, known as Aurora2, STK15 or BTAK, belongs to the serine/threonine kinase family. Bischoff et al. have shown that Aurora2 is oncogenic, and is amplified in human colorectal cancers (EMBO J, 1998, 17, 3052-3065). This has also been illustrated in cancers involving epithelial tumors such as breast cancer.

Tie-2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signaling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knockout experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumor growth and vascularization, and also a reduction in lung metastases, during adenoviral infections or injections of the extracellular domain of Tie-2 (Tek) into models of melanoma and breast tumor xenografts.

Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile hemoangioma and cancers).

FAK is a cytoplasmic tyrosine kinase that plays an important role in transducing the signal transmitted by the integrins, a family of heterodimeric cellular adhesion receptors. FAK and the integrins are colocated in perimembrane structures known as adhesion plaques. It has been shown in many cell types that the activation of FAK and its phosphorylation on tyrosine residues and in particular its autophosphorylation on tyrosine 397 are dependent on the binding of integrins to their extracellular ligands and thus induced during cellular adhesion [Kornberg L, et al. J. Biol. Chem. 267(33): 23439-442 (1992)]. Autophosphorylation on tyrosine 397 of FAK represents a binding site for another tyrosine kinase, Src, via its SH2 domain [Schaller et al. Mol. Cell. Biol. 14: 1680-1688. 1994; Xing et al. Mol. Cell. Biol. 5: 413-421. 1994]. Src may then phosphorylate FAK on tyrosine 925, thus recruiting the adapter protein Grb2 and inducing in certain cells activation of the ras and MAP kinase pathway involved in controlling cell proliferation [Schlaepfer et al. Nature; 372: 786-791. 1994; Schlaepfer et al. Prog. Biophys. Mol. Biol. 71: 435-478. 1999; Schlaepfer and Hunter, J. Biol. Chem. 272: 13189-13195. 1997]. The activation of FAK may also induce the jun NH2-terminal kinase (JNK) signaling pathway and result in the progression of cells towards the G1 phase of the cell cycle [Oktay et al., J. Cell. Biol. 145: 1461-1469. 1999]. Phosphatidylinositol-3-OH kinase (PI3-kinase) also binds to FAK on tyrosine 397 and this interaction might be necessary for activating PI3-kinase [Chen and Guan, Proc. Nat. Acad. Sci. USA. 91: 10148-10152. 1994; Ling et al. J. Cell. Biochem. 73: 533-544. 1999]. The FAK/Src complex phosphorylates various substrates, for instance paxillin and p130CAS in fibroblasts [Vuori et al. Mol. Cell. Biol. 16: 2606-2613. 1996].

The results of numerous studies support the hypothesis that FAK inhibitors might be useful in treating cancer. Studies have suggested that FAK might play an important role in cell proliferation and/or survival in vitro. For example, in CHO cells, some authors have demonstrated that the overexpression of p125FAK leads to an acceleration of the transition G1 to S, suggesting that p125FAK promotes cell proliferation [Zhao J.-H et al. J. Cell Biol. 143: 1997-2008. 1998]. Other authors have shown that tumor cells treated with FAK antisense oligonucleotides lose their adhesion and enter into apoptosis (Xu et al., Cell Growth Differ. 4: 413-418. 1996). It has also been demonstrated that FAK promotes the migration of cells in vitro. Thus, fibroblasts that are deficient for FAK expression (FAK "knockout" mice) show a rounded morphology and deficiencies in cellular migration in response to chemotactic signals, and these defects are eliminated by re-expression of FAK [D J. Sieg et al., J. Cell Science. 112: 2677-91. 1999]. Overexpression of the C-terminal domain of FAK (FRNK) blocks the stretching of adherent cells and reduces cell migration in vitro [Richardson A. and Parsons J. T. Nature. 380: 538-540. 1996]. Overexpression of FAK in CHO or COS cells or in human astrocytoma cells promotes migration of the cells. The involvement of FAK in promotion of the proliferation and migration of cells in many cell types in vitro suggests the potential role of FAK in neoplastic processes. A recent study has effectively demonstrated the increase in the proliferation of tumor cells in vivo after inducing the expression of FAK in human astrocytoma cells [Cary L. A. et al. J. Cell Sci. 109: 1787-94. 1996; Wang D et al. J. Cell Sci. 113: 4221-4230. 2000]. Furthermore, immunohistochemical studies of human biopsies have demonstrated that FAK was overexpressed in prostate cancer, breast cancer, thyroid cancer, colon cancer, melanoma, brain cancer and lung cancer, the level of expression of FAK being directly correlated to the tumors showing the most aggressive phenotype [Weiner T M, et al. Lancet. 342 (8878): 1024-1025. 1993; Owens et al. Cancer Research. 55: 2752-2755. 1995; Maung K. et al. Oncogene. 18: 6824-6828. 1999; Wang D et al. J. Cell Sci. 113: 4221-4230. 2000].

KDR (Kinase insert Domain Receptor), also known as VEGF-R2 (Vascular Endothelial Growth Factor Receptor 2), is expressed solely in endothelial cells. This receptor binds to the angiogenic growth factor VEGF, and thus serves as a transduction signal mediator via the activation of its intracellular kinase domain. The direct inhibition of the kinase activity of VEGF-R2 makes it possible to reduce the phenomenon of angiogenesis in the presence of exogenous VEGF (Vascular Endothelial Growth Factor) (Strawn et al., Cancer Research, 1996, vol. 56, p. 3540-3545). This process has especially been demonstrated using VEGF-R2 mutants (Millauer et al., Cancer Research, 1996, vol. 56, p. 1615-1620). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergy of KDR inhibitors with other agents (Lee et al. Cancer Research, 2000, vol. 60, pp. 5565-5570).

Experimental Protocols on the Biochemical Tests

1. Aurora1 and Aurora2

The inhibitory effect of compounds with respect to the kinases Aurora1 and Aurora2 is determined by means of an enzymatic test using radioactivity detection.

The kinase activity of Aurora1 and Aurora2 is evaluated via the phosphorylation of the substrate Numa-histidine in the presence of radiolabelled ATP ($[^{33}P]$ATP) using 96-well Flashplate plates in which the nickel chelate is bound to the surface of the microplate. The amount of $^{33}P$ phosphate incorporated into the NuMA substrate is proportional to the activity of the enzyme Aurora1 or Aurora2.

Proteins:

The proteins are produced in the protein production laboratory of the Sanofi-Aventis group.

Aurora1: Aurora-B/INCENP-C3 recombinant complex, purified to about 50%, the N-terminal end of Aurora-B of which has been labeled with histidine.

Aurora2: whole recombinant protein comprising an N-terminal histidine tail, was expressed in E. coli and purified to more than 82%.

NuMA (nuclear protein that combines with the mitotic apparatus): 424-amino acid fragment, expressed in E. coli, the N-terminal end of which has been labeled with histidine, and used as substrate for the two Aurora enzymes.

Protocol:

The microplates used are 96-well Flash-Plate plates, nickel chelate (Perkin-Elmer, model SMP107).

The products to be evaluated are incubated in a reaction volume of 100 µL per well, in the presence of 10 nM of Aurora1 or Aurora2, 500 nM of NuMA substrate in a buffer composed of 50 mM Tris/HCl (pH 7.5), 50 mM NaCl, 5 mM $MgCl_2$ (Aurora-B) or 10 mM $MgCl_2$ (Aurora-A) and 1 mM DTT, at 37° C.

80 µL of enzyme/substrate incubation buffer are distributed in each well, followed by 10 µL of product to be evaluated, at variable concentrations. The reaction is initiated by adding 1 µM final of ATP containing 0.2 µCi of $[^{33}P]$ATP (10 µL). After incubating for 30 minutes, the reaction is quenched by simple removal of the reaction buffer and each well is washed twice with 300 µl of Tris/HCl buffer. The radioactivity is then measured in each well using a Packard, Top-Count model scintillation machine.

The control enzymatic activity of Aurora is expressed by the number of counts per minute obtained over 30 minutes after subtracting the background noise (reaction mixture containing no enzyme). The evaluation of the various test products is expressed as a percentage of inhibition of the Aurora activity relative to the control.

2. CDK2/Cycline E:

Purification of the CDK2/cyclineE-(His)$_6$ Complex by IMAC (Immobilized Metal Affinity Chromatography):

Two recombinant baculoviruses bearing the human sequences coding, respectively, for CDK2 and cyclineE (the latter bearing a C-terminal hexahistidine tag) are used to coinfect Sf21 insect cells. Two to three days after the start of coinfection, the cells are harvested by centrifugation and then stored at −40° C. until the time of use. After thawing and mechanical lysis of the cells, the complex present in the lysis supernatant is purified by affinity chromatography on nickel (IMAC), and stored at −80° C.

CDK2/cyclineE Flashplate Test in 96-Well Format.

A format in streptavidin-coated 96-well plates is used to test the activity of the compounds on the kinase activity of CDK2/cycline E.

To perform this test, the biotinylated peptide substrate, a fragment of the protein pRb (biotinyl-SACPLNLPLQN-NHTAADMYLSPVRSPKKKGSTTR-OH), is dissolved at a concentration of 1 mM in kinase buffer (HEPES/NaOH 50 mM, NaCl 1 mM, MgCl$_2$ 5 mM, pH 7.5) in order to constitute a stock solution stored at −20° C. in the form of 110 µL aliquots. On the day of the experiment, an aliquot of this solution is thawed and diluted in kinase buffer containing 1 mM of dithiothreitol, added to the buffer extemporaneously, in order to obtain a concentration of 14.3 µM. 70 µL of this solution are added to each well of the Flashplate in order to obtain a final substrate concentration of 10 µM during the enzymatic reaction performed in a final volume of the reaction medium of 100 µL (cf. below).

Intermediate dilutions of inhibitors (products of the invention) at various concentrations are prepared in DMSO from stock solutions at 10 mM in separate tubes. Dilutions at 1000 µM, 333.3 µM, 111.1 µM, 37.03 µM, 12.35 µM, 4.11 µM and 1.37 µM are thus prepared. One µL of each of these solutions (or 1 µL of DMSO for the controls) is transferred into the wells of the test plate.

19 µl of a solution of a mixture of adenosine triphosphate (ATP) and of ATPγ$^{33}$P in kinase buffer at a total concentration of 5.26 µM of ATP and 52.6 µCi/ml of $^{33}$P are then added to each well. The enzymatic reaction is initiated by adding 10 µL per well of a 200 nM solution of CDK2/cycline E in kinase buffer containing 1 mM of dithiothreitol (or 10 µL of kinase buffer containing 1 mM of dithiothreitol for the reaction blanks).

After addition of each of the reagents, the final volume of each well is 100 µL, the final concentration of substrate is 10 µM, the final inhibitor concentrations are 10 µM, 3.33 µM, 1.11 µM, 0.37 µM, 0.123 µM, 0.041 µM and 0.014 µM (according to the concentration of the intermediate dilution), the final ATP concentration is 1 µM, the final amount of $^{33}$P is 1 µCi/well, and the final concentration of CDK2/cycline E complex is 20 nM.

After addition of all of the reagents, the test plate is incubated at 30° C. with orbital shaking at 650 rpm.

When the incubation is complete, the plate is washed three times with 300 µL per well of PBS (phosphate-buffered saline, pH=7.4, without calcium or magnesium, reference 10010-015, Gibco BRL). The incorporation of $^{33}$P to the peptide is quantified by scintillation counting with a Packard Topcount.NXT machine. The inhibitory activity of the products of the invention is evaluated by measuring the inhibitory concentration that allows a 50% reduction in the enzymatic activity (IC$_{50}$).

3. Tie2

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM MgCl$_2$, 10 mM MnCl$_2$, 1 mM DTT, 10 mM of glycerophosphate. In a 96-well Flash-Plate plate maintained on ice, a reaction mixture is deposited, composed of 70 µL of kinase buffer containing 100 ng of enzyme GST-Tie2 per well. Next, 10 µL of the test molecule diluted in DMSO to a maximum concentration of 10% are added. For a given concentration, each measurement is performed four times. The reaction is initiated by adding 20 µL of solution containing 2 µg of GST-PLC, 2 µm of cold ATP and 1 µCi of $^{33}$P[ATP]. After incubation for one hour at 37° C., the reaction is stopped by adding 1 volume (100 µl) of 200 mM EDTA. After removal of the incubation buffer, the wells are washed three times with 300 µL of PBS. The radioactivity is measured on a MicroBeta1450 Wallac.

The inhibition of the Tie2 activity is calculated and expressed as a percentage of inhibition relative to the control activity determined in the absence of compound.

Activity of the Products Prepared:

The activity of the products was determined by measuring the inhibition of the activity of Aurora1, Aurora2, CDK2 and Tie2. The results are given in table 1 below (IC$_{50}$, nM).

| Example | Aurora1 | Aurora2 | CDK2 | Tie2 |
|---|---|---|---|---|
| 1 | 8 | 8 | 177 | 117 |
| 2 | 9 | 9 | 97 | 92 |
| 3 | 31 | 45 | 471 | 192 |
| 4 | 6 | 28 | 508 | 115 |
| 5 | 33 | 28 | 664 | 75 |
| 6 | 14 | 20 | 579 | 230 |
| 7 | 16 | 17 | 428 | 186 |
| 8 | 29 | 8 | 134 | 252 |
| 9 | 131 | 157 | 65 | 820 |
| 10 | 102 | 46 | 92 | 367 |
| 11a | 178 | 31 | 156 | 520 |
| 11b | 216 | 73 | 77 | 704 |
| 12a | 128 | 31 | 126 | 564 |
| 12b | 151 | 68 | 40 | 218 |
| 13a | 141 | 23 | 151 | 679 |
| 13b | 182 | 85 | 49 | 324 |
| 14a | 158 | 19 | 166 | 737 |
| 14b | 148 | 44 | 46 | 425 |
| 15a | 114 | 12 | 210 | 623 |
| 15b | 329 | 37 | 82 | 393 |
| 16a | 992 | 301 | 942 | 3213 |
| 16b | 936 | 606 | 301 | 2007 |
| 17a | 59 | 7 | 175 | 482 |
| 17b | 335 | 35 | 93 | 230 |
| 18a | 122 | 14 | 181 | 624 |
| 18b | 287 | 50 | 96 | 388 |
| 19 | 304 | 26 | 239 | 888 |
| 20a | 190 | 70 | 347 | 842 |
| 20b | 155 | 75 | 109 | 369 |
| 21a | 55 | 14 | 122 | 430 |
| 21b | 160 | 34 | 82 | 301 |
| 22a | 147 | 81 | 717 | 2212 |
| 22b | 956 | 762 | 703 | 3190 |

-continued

| Example | Aurora1 | Aurora2 | CDK2 | Tie2 |
|---|---|---|---|---|
| 23a | 199 | 65 | 143 | 431 |
| 23b | 259 | 101 | 138 | 543 |
| 24 | 288 | 49 | 1486 | 1027 |
| 25 | 249 | 25 | 317 | 328 |
| 26 | 42 | 23 | 75 | 175 |
| 27 | 51 | 31 | 669 | 294 |
| 28 | 6 | 2 | 132 | 106 |
| 29 | 28 | 11 | 585 | 163 |
| 30 | 12 | 6 | 221 | 128 |
| 31 | 96 | 26 | 275 | 3063 |
| 32 | 25 | 4 | 109 | 38 |
| 33 | 13 | 5 | 100 | 8 |
| 34 | 13 | 5 | 1581 | 38 |
| 35 | 4 | 4 | 121 | 29 |
| 36 | 9 | 5 | 1924 | 6 |
| 37 | 32 | 20 | 54 | 56 |
| 38 | 21 | 4 | 214 | 58 |
| 39 | 15 | 27 | 53 | 22 |
| 40 | 11 | 17 | 105 | 25 |
| 41 | 15 | 25 | 294 | 44 |
| 42 | 24 | 6 | 1122 | 61 |
| 43 | 5 | 1 | 32 | 8 |
| 44 | 21 | 6 | 201 | 107 |
| 45 | 33 | 21 | 146 | 29 |
| 46 | 12 | 6 | 100 | 275 |
| 47 | 8 | 5 | 289 | 75 |

What is claimed is:

1. A compound of formula (I):

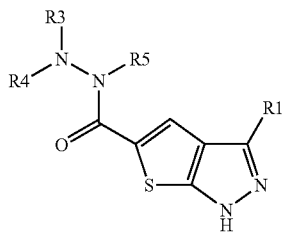

wherein:
(i) R1 is independently selected from the group consisting of —NHCO(R2), —NHCONH(R2) and —NHCOO(R2), in which R2 is independently selected from the group consisting of —H, —($C_1$-$C_{24}$)alkyl, —($C_3$-$C_9$)cycloalkyl, —($C_3$-$C_9$)cycloalkylene, heterocycloalkyl, heterocycloalkylene, aryl, heteroaryl, —($C_1$-$C_6$)alkyl-aryl, —($C_1$-$C_6$)alkyl-heteroaryl, -aryl-($C_1$-$C_6$)alkyl and heteroaryl-($C_1$-$C_6$)alkyl, optionally substituted;
(ii) each of the R3, R4 and R5 is independently selected from the group consisting of —H, —($C_1$-$C_6$)alkyl, —($C_1$-$C_6$)alkyl-aryl, —($C_1$-$C_6$)alkyl-heteroaryl, -aryl and -heteroaryl, optionally substituted, or alternatively [(R3 and R4) or (R3 and R5)] are linked together to form a saturated or unsaturated, 2- to 10-membered monocyclic or bicyclic carbon heterocycle containing from 1 to 5 heteroatoms chosen from N, O and S, optionally substituted, or to form a group N=CH-aryl, said aryl being optionally substituted;
or a pharmaceutically acceptable salt thereof.

2. The compound according to claim 1, wherein R5 is H.
3. The compound according to claim 1, wherein R4 is H.
4. The compound according to claim 1, wherein R4 is methyl or ethyl.
5. The compound according to claim 1, wherein R3 and R4 form, with the nitrogen atom to which they are attached, a 5- or 6-membered heterocycle also containing, where appropriate, an N, O or S atom, optionally substituted.
6. The compound according to claim 1, wherein R1 is NHCO(R2), R2 being as defined in claim 1.
7. The compound according to claim 1, wherein R3 is aryl or heteroaryl, —($C_1$-$C_6$)alkyl-aryl or —($C_1$-$C_6$)alkyl-heteroaryl, optionally substituted.
8. The compound according to claim 1, corresponding to formula (I'):

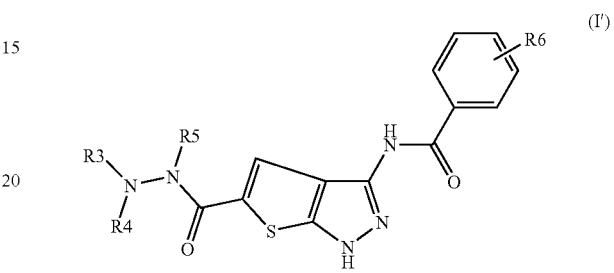

wherein:
each of the groups R3, R4 and R5 is as defined in claim 1,
R6 is chosen from the group consisting of halogen, ($C_1$-$C_3$)alkyl-NR7R8, ($C_1$-$C_6$)alkoxy, ($C_0$-$C_3$)alkyl-heterocycle, ($C_0$-$C_3$)alkyl-aryl, ($C_0$-$C_3$)alkyl-heteroaryl and ($C_0$-$C_3$)alkyl-cycloalkyl, in which the rings are optionally substituted with one or more substituents ($C_1$-$C_3$)alkyl, halogen or alkoxy, and in which R7 and R8 are independently selected from the group consisting of —H, ($C_0$-$C_3$)alkyl, aryl and ($C_1$-$C_3$)alkyl-N—[($C_0$-$C_3$)alkyl]$_2$.

9. The compound according to claim 8, wherein R6 is in position 3 or 4.
10. The compound according to claim 9, wherein R6 is ($C_0$-$C_3$)alkyl-heterocycle, said heterocycle being optionally substituted with one or more substituents selected from ($C_1$-$C_3$)alkyl, halogen and alkoxy.
11. The compound according to claim 1, wherein aryl and heteroaryl are each independently chosen from phenyl, pyridyl, indolyl, benzimidazolyl, pyrazolyl, thienyl and pyrrolyl, optionally substituted.
12. The compound according to claim 1, selected from the group consisting of:

5-(N'-Phenylhydrazinocarbonyl)-1H-thieno[2,3-c]pyrazol-3-yl]-4-methoxybenzamide;
5-(N'-Methyl-N'-phenylhydrazinocarbonyl)-1H-thieno[2,3-c]pyrazol-3-yl]-4-methoxybenzamide;
N-[5-(N'-Cyclohexylhydrazinocarbonyl)-1H-thieno[2,3-c]pyrazol-3-yl]-4-methoxybenzamide;
N-[5-(N'-Benzyl-N'-phenylhydrazinocarbonyl)-1H-thieno[2,3-c]pyrazol-3-yl]-4-methoxybenzamide;
N-{5-[N'-(2-Ethylphenyl)hydrazinocarbonyl]-1H-thieno[2,3-c]pyrazol-3-yl}-4-methoxybenzamide;
N-{5-[N'-(2-Fluorophenyl)hydrazinocarbonyl]-1H-thieno[2,3-c]pyrazol-3-yl}-4-methoxybenzamide;
4-Methoxy-N-[5-(N'-o-tolylhydrazinocarbonyl)-1H-thieno[2,3-c]pyrazol-3-yl]benzamide;
N-[5-(N'-Methyl-N'-phenylhydrazinocarbonyl)-1H-thieno[2,3-c]pyrazol-3-yl]-4-morpholin-4-ylmethylbenzamide;
4-Bromo-N-[5-(N'-methyl-N'-phenylhydrazinocarbonyl)-1H-thieno[2,3-c]pyrazol-3-yl]benzamide;

N-[5-(N'-Methyl-N'-phenylhydrazinocarbonyl)-1H-thieno[2,3-c]pyrazol-3-yl]-4-(4-methylpiperazin-1-ylmethyl)benzamide;

4-(3,5-Dimethylpiperazin-1-ylmethyl)-N-[5-(N'-methyl-N'-phenylhydrazinocarbonyl)-1H-thieno[2,3-c]pyrazol-3-yl]benzamide;

4-(3,5-Dimethylpiperazin-1-ylmethyl)-N-[5-(N'-(4-chlorophenyl)-N'-methylhydrazinocarbonyl)-1H-thieno[2,3-c]pyrazol-3-yl]benzamide;

4-(4-Methylperhydro-1,4-diazepin-1-ylmethyl)-N-[5-(N'-methyl-N'-phenylhydrazinocarbonyl)-1H-thieno[2,3-c]pyrazol-3-yl]benzamide;

4-(4-Methylperhydro-1,4-diazepin-1-ylmethyl)-N-[5-(N'-(4-chlorophenyl)-N'-methylhydrazinocarbonyl)-1H-thieno[2,3-c]pyrazol-3-yl]benzamide;

N-[5-(N'-Methyl-N'-phenylhydrazinocarbonyl)-1H-thieno[2,3-c]pyrazol-3-yl]-4-piperazin-1-ylmethylbenzamide;

N-{5-[N'-(4-Chlorophenyl)-N'-methylhydrazinocarbonyl]-1H-thieno[2,3-c]pyrazol-3-yl}-4-piperazin-1-ylmethylbenzamide;

N-[5-(N'-Methyl-N'-phenylhydrazinocarbonyl)-1H-thieno[2,3-c]pyrazol-3-yl]-4-(3-methylpiperazin-1-ylmethyl)benzamide;

N-{5-[N'-(4-Chlorophenyl)-N'-methylhydrazinocarbonyl]-1H-thieno[2,3-c]pyrazol-3-yl}-4-(3-methylpiperazin-1-ylmethyl)benzamide;

4-Diethylaminomethyl-N-[5-(N'-methyl-N'-phenylhydrazinocarbonyl)-1H-thieno[2,3-c]pyrazol-3-yl]benzamide trifluoroacetate;

N-{5-[N'-(4-Chlorophenyl)-N'-methylhydrazinocarbonyl]-1H-thieno[2,3-c]pyrazol-3-yl}-4-diethylaminomethylbenzamide;

N-[5-(N'-Methyl-N'-phenylhydrazinocarbonyl)-1H-thieno[2,3-c]pyrazol-3-yl]-3-(4-methylpiperazin-1-ylmethyl)benzamide;

N-[5-(N'-(4-Chlorophenyl)-N'-methylhydrazinocarbonyl)-1H-thieno[2,3-c]pyrazol-3-yl]-3-(4-methylpiperazin-1-ylmethyl)benzamide;

N-[5-(N'-Methyl-N'-phenylhydrazinocarbonyl)-1H-thieno[2,3-c]pyrazol-3-yl]-4-piperid-1-ylmethylbenzamide;

N-[5-(N'-(4-Chlorophenyl)-N'-methylhydrazinocarbonyl)-1H-thieno[2,3-c]pyrazol-3-yl]-4-piperid-1-ylmethylbenzamide;

N-[5-(N'-Methyl-N'-phenylhydrazinocarbonyl)-1H-thieno[2,3-c]pyrazol-3-yl]-4-pyrrolidin-1-ylmethylbenzamide;

N-[5-(N'-(4-Chlorophenyl)-N'-methylhydrazinocarbonyl)-1H-thieno[2,3-c]pyrazol-3-yl]-4-pyrrolidin-1-ylmethylbenzamide;

4-Azetidin-1-ylmethyl-N-[5-(N'-methyl-N'-phenylhydrazinocarbonyl)-1H-thieno[2,3-c]pyrazol-3-yl]benzamide;

4-{[(2-Dimethylaminoethyl)methylamino]methyl}-N-[5-(N'-methyl-N'-phenylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-{[(2-dimethylaminoethyl)methylamino]methyl}benzamide;

N-[5-(N'-Methyl-N'-phenylhydrazinocarbonyl)-1H-thieno[2,3-c]pyrazol-3-yl]-4-perhydro-1,4-oxazepin-4-ylmethylbenzamide;

N-{5-[N'-(4-Chlorophenyl)-N'-methylhydrazinocarbonyl]-1H-thieno[2,3-c]pyrazol-3-yl}-4-perhydro-1,4-oxazepin-4-ylmethylbenzamide;

N-[5-(N'-Methyl-N'-phenylhydrazinocarbonyl)-1H-thieno[2,3-c]pyrazol-3-yl]-3-morpholin-4-ylmethylbenzamide;

N-{5-[N'-(4-Chlorophenyl)-N'-methylhydrazinocarbonyl]-1H-thieno[2,3-c]pyrazol-3-yl}-3-morpholin-4-ylmethylbenzamide;

4-[(2-Diethylaminoethylamino)methyl]-N-[5-(N'-methyl-N'-phenylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-[(2-diethylaminoethylamino)methyl]benzamide;

4-[(Methylphenylamino)methyl]-N-[5-(N'-methyl-N'-phenylhydrazinocarbonyl)-1H-thieno[2,3-c]pyrazol-3-yl]benzamide;

4-[(Diisopropylamino)methyl]-N-[5-(N'-methyl-N'-phenylhydrazinocarbonyl)-1H-thieno[2,3-c]pyrazol-3-yl]benzamide trifluoroacetate;

N-[5-(N'-Benzylhydrazinocarbonyl)-1H-thieno[2,3-c]pyrazol-3-yl]-4-methoxybenzamide;

4-Methoxy-N-[5-(N'-pyrid-2-ylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-(4-methylpiperazin-1-yl)benzamide;

N-[5-(N'-Benzyl-N'-methylhydrazinocarbonyl)-1H-thieno[2,3-c]pyrazol-3-yl]-4-(4-methylpiperazin-1-yl)benzamide;

N-(Piperid-1-yl)-3-[4-(4-methylpiperazin-1-yl)benzoylamino]-1H-thieno[2,3-c]-pyrazole-5-carboxamide;

N-[5-(N'-Benzylhydrazinocarbonyl)-1H-thieno[2,3-c]pyrazol-3-yl]-4-(4-methylpiperazin-1-yl)benzamide;

N-[5-(N'-Ethyl-N'-phenylhydrazinocarbonyl)-1H-thieno[2,3-c]pyrazol-3-yl]-4-(4-methylpiperazin-1-yl)benzamide;

N-[5-(N'-Benzyl-N'-phenylhydrazinocarbonyl)-1H-thieno[2,3-c]pyrazol-3-yl]-4-(4-methylpiperazin-1-yl)benzamide;

N-[5-(N'-Methyl-N'-phenylhydrazinocarbonyl)-1H-thieno[2,3-c]pyrazol-3-yl]-4-(4-methylpiperazin-1-yl)benzamide;

N-{5-[N'-(4-Chlorophenyl)-N'-cyclobutylmethylhydrazinocarbonyl]-1H-thieno[2,3-c]pyrazol-3-yl}-4-(4-methylpiperazin-1-yl)benzamide;

N-{5-[N'-Ethyl-N'-(4-fluorophenyl)hydrazinocarbonyl]-1H-thieno[2,3-c]pyrazol-3-yl}-4-(4-methylpiperazin-1-yl)benzamide;

N-{5-[N'-(4-Fluorophenyl)-N'-(2-methoxyethyl)hydrazinocarbonyl]-1H-thieno[2,3-c]pyrazol-3-yl}-4-(4-methylpiperazin-1-yl)benzamide;

N-[5-(N'-Ethyl-N'-o-tolylhydrazinocarbonyl)-1H-thieno[2,3-c]pyrazol-3-yl]-4-(4-methylpiperazin-1-yl)benzamide;

N-[5-(N'-Ethyl-N'-m-tolylhydrazinocarbonyl)-1H-thieno[2,3-c]pyrazol-3-yl]-4-(4-methylpiperazin-1-yl)benzamide;

N-[5-(N'-Ethyl-N'-m-tolylhydrazinocarbonyl)-1H-thieno[2,3-c]pyrazol-3-yl]-4-(4-methylpiperazin-1-yl)benzamide;

N-{5-[N'-(4-Fluorophenyl)-N'-isobutylhydrazinocarbonyl]-1H-thieno[2,3-c]pyrazol-3-yl}-4-(4-methylpiperazin-1-yl)benzamide;

N-{5-[N'-(3-Bromophenyl)-N'-ethylhydrazinocarbonyl]-1H-thieno[2,3-c]pyrazol-3-yl}-4-(4-methylpiperazin-1-yl)benzamide;

6-(4-Methyl[1,4]diazepan-1-yl)-N-[5-(N'-methyl-N'-phenylhydrazinocarbonyl)-1H-thieno[2,3-c]pyrazol-3-yl]nicotinamide;

N-[5-(Benzylidenehydrazinocarbonyl)-1H-thieno[2,3-c]pyrazol-3-yl]-4-(4-methylpiperazin-1-yl)benzamide;

N-[5-(N'-Methyl-N'-phenylhydrazinocarbonyl)-1H-thieno[2,3-c]pyrazol-3-yl]-4-(2-morpholin-4-ylethoxy)benzamide; and 4-(4-Methyl[1,4]diazepan-1-yl)-N-[5-(N'-methyl-N'-phenylhydrazinocarbonyl)-1H-thieno[2,3-c]pyrazol-3-yl]benzamide;

or a pharmaceutically acceptable salt thereof.

13. A process for preparing a compound of formula (I):

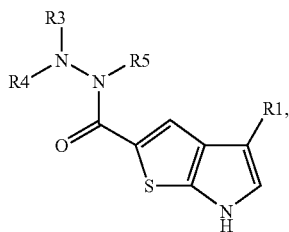

(I)

wherein R1 is NHCO(R2), and in which each R3, R4 and R5 is independently selected from the group consisting of —H, —(C$_1$-C$_6$)alkyl, —(C$_1$-C$_6$)alkyl-aryl, —(C$_1$-C$_6$)alkyl-heteroaryl, -aryl and -heteroaryl, optionally substituted, or alternatively [(R3 and R4) or (R3 and R5)] are linked together to form a saturated or unsaturated, 2- to 10-membered monocyclic or bicyclic carbon heterocycle containing from 1 to 5 heteroatoms chosen from N, O and S, optionally substituted, or to form a group N=CH-aryl, said aryl being optionally substituted;
said compound of formula (I) being obtained by:
(i) coupling between (i-a) an acid of formula (X):

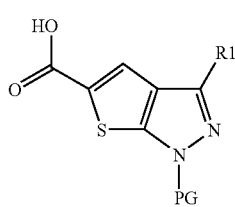

(X)

wherein R1 is as defined above, and in which PG is a protecting group for the free endocyclic NH function of the thieno[2,3-c]pyrazole nucleus, and
(i-b) a hydrazine (R3)(R4)N—NH(R5) in which R3, R4 and R5 are as defined above, in the presence of a coupling agent and in the presence of a base; followed by:
(ii) cleavage of PG.

14. A pharmaceutical composition comprising a pharmaceutically acceptable excipient in combination with a compound of formula (I):

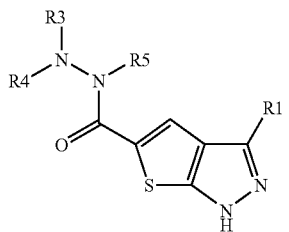

(I)

wherein:
(i) R1 is independently selected from the group consisting of —NHCO(R2), —NHCONH(R2) and —NHCOO(R2), in which R2 is independently selected from the group consisting of —H, —(C$_1$-C$_{24}$)alkyl, —(C$_3$-C$_9$)cycloalkyl, —(C$_3$-C$_9$)cycloalkylene, heterocycloalkyl, heterocycloalkylene, aryl, heteroaryl, —(C$_1$-C$_6$)alkyl-aryl, —(C$_1$-C$_6$)alkyl-heteroaryl, -aryl-(C$_1$-C$_6$)alkyl and heteroaryl-(C$_1$-C$_6$)alkyl, optionally substituted;
(ii) each of the R3, R4 and R5 is independently selected from the group consisting of —H, —(C$_1$-C$_6$)alkyl, —(C$_1$-C$_6$)alkyl-aryl, —(C$_1$-C$_6$)alkyl-heteroaryl, -aryl and -heteroaryl, optionally substituted, or alternatively [(R3 and R4) or (R3 and R5)] are linked together to form a saturated or unsaturated, 2- to 10-membered monocyclic or bicyclic carbon heterocycle containing from 1 to 5 heteroatoms chosen from N, O and S, optionally substituted, or to form a group N=CH-aryl, said aryl being optionally substituted;
or a pharmaceutically acceptable salt thereof.

15. The pharmaceutical composition according to claim 14, wherein the compound is selected from the group consisting of:
5-(N'-Phenylhydrazinocarbonyl)-1H-thieno[2,3-c]pyrazol-3-yl]-4-methoxybenzamide;
5-(N'-Methyl-N'-phenylhydrazinocarbonyl)-1H-thieno[2,3-c]pyrazol-3-yl]-4-methoxybenzamide;
N-[5-(N'-Cyclohexylhydrazinocarbonyl)-1H-thieno[2,3-c]pyrazol-3-yl]-4-methoxybenzamide;
N-[5-(N'-Benzyl-N'-phenylhydrazinocarbonyl)-1H-thieno[2,3-c]pyrazol-3-yl]-4-methoxybenzamide;
N-{5-[N'-(2-Ethylphenyl)hydrazinocarbonyl]-1H-thieno[2,3-c]pyrazol-3-yl}-4-methoxybenzamide;
N-{5-[N'-(2-Fluorophenyl)hydrazinocarbonyl]-1H-thieno[2,3-c]pyrazol-3-yl}-4-methoxybenzamide;
4-Methoxy-N-[5-(N'-o-tolylhydrazinocarbonyl)-1H-thieno[2,3-c]pyrazol-3-yl]benzamide;
N-[5-(N'-Methyl-N'-phenylhydrazinocarbonyl)-1H-thieno[2,3-c]pyrazol-3-yl]-4-morpholin-4-ylmethylbenzamide;
4-Bromo-N-[5-(N'-methyl-N'-phenylhydrazinocarbonyl)-1H-thieno[2,3-c]pyrazol-3-yl]benzamide;
N-[5-(N'-Methyl-N'-phenylhydrazinocarbonyl)-1H-thieno[2,3-c]pyrazol-3-yl]-4-(4-methylpiperazin-1-ylmethyl)benzamide;
4-(3,5-Dimethylpiperazin-1-ylmethyl)-N-[5-(N'-methyl-N'-phenylhydrazinocarbonyl)-1H-thieno[2,3-c]pyrazol-3-yl]benzamide;
4-(3,5-Dimethylpiperazin-1-ylmethyl)-N-[5-(N'-(4-chlorophenyl)-N'-methylhydrazinocarbonyl)-1H-thieno[2,3-c]pyrazol-3-yl]benzamide;
4-(4-Methylperhydro-1,4-diazepin-1-ylmethyl)-N-[5-(N'-methyl-N'-phenylhydrazinocarbonyl)-1H-thieno[2,3-c]pyrazol-3-yl]benzamide;
4-(4-Methylperhydro-1,4-diazepin-1-ylmethyl)-N-[5-(N'-(4-chlorophenyl)-N'-methylhydrazinocarbonyl)-1H-thieno[2,3-c]pyrazol-3-yl]benzamide;
N-[5-(N'-Methyl-N'-phenylhydrazinocarbonyl)-1H-thieno[2,3-c]pyrazol-3-yl]-4-piperazin-1-ylmethylbenzamide;
N-{5-[N'-(4-Chlorophenyl)-N'-methylhydrazinocarbonyl]-1H-thieno[2,3-c]pyrazol-3-yl}-4-piperazin-1-ylmethylbenzamide;
N-[5-(N'-Methyl-N'-phenylhydrazinocarbonyl)-1H-thieno[2,3-c]pyrazol-3-yl]-4-(3-methylpiperazin-1-ylmethyl)benzamide;
N-{5-[N'-(4-Chlorophenyl)-N'-methylhydrazinocarbonyl]-1H-thieno[2,3-c]pyrazol-3-yl}-4-(3-methylpiperazin-1-ylmethyl)benzamide;
4-Diethylaminomethyl-N-[5-(N'-methyl-N'-phenylhydrazinocarbonyl)-1H-thieno[2,3-c]pyrazol-3-yl]benzamide trifluoroacetate;
N-{5-[N'-(4-Chlorophenyl)-N'-methylhydrazinocarbonyl]-1H-thieno[2,3-c]pyrazol-3-yl}-4-diethylaminomethylbenzamide;

N-[5-(N'-Methyl-N'-phenylhydrazinocarbonyl)-1H-thieno[2,3-c]pyrazol-3-yl]-3-(4-methylpiperazin-1-ylmethyl)benzamide;

N-[5-(N'-(4-Chlorophenyl)-N'-methylhydrazinocarbonyl)-1H-thieno[2,3-c]pyrazol-3-yl]-3-(4-methylpiperazin-1-ylmethyl)benzamide;

N-[5-(N'-Methyl-N'-phenylhydrazinocarbonyl)-1H-thieno[2,3-c]pyrazol-3-yl]-4-piperid-1-ylmethylbenzamide;

N-[5-(N'-(4-Chlorophenyl)-N'-methylhydrazinocarbonyl)-1H-thieno[2,3-c]pyrazol-3-yl]-4-piperid-1-ylmethylbenzamide;

N-[5-(N'-Methyl-N'-phenylhydrazinocarbonyl)-1H-thieno[2,3-c]pyrazol-3-yl]-4-pyrrolidin-1-ylmethylbenzamide;

N-[5-(N'-(4-Chlorophenyl)-N'-methylhydrazinocarbonyl)-1H-thieno[2,3-c]pyrazol-3-yl]-4-pyrrolidin-1-ylmethylbenzamide;

4-Azetidin-1-ylmethyl-N-[5-(N'-methyl-N'-phenylhydrazinocarbonyl)-1H-thieno[2,3-c]pyrazol-3-yl]benzamide;

4-{[(2-Dimethylaminoethyl)methylamino]methyl}-N-[5-(N'-methyl-N'-phenylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-{[(2-dimethylaminoethyl)methylamino]methyl}benzamide;

N-[5-(N'-Methyl-N'-phenylhydrazinocarbonyl)-1H-thieno[2,3-c]pyrazol-3-yl]-4-perhydro-1,4-oxazepin-4-ylmethylbenzamide;

N-{5-[N'-(4-Chlorophenyl)-N'-methylhydrazinocarbonyl]-1H-thieno[2,3-c]pyrazol-3-yl}-4-perhydro-1,4-oxazepin-4-ylmethylbenzamide;

N-[5-(N'-Methyl-N'-phenylhydrazinocarbonyl)-1H-thieno[2,3-c]pyrazol-3-yl]-3-morpholin-4-ylmethylbenzamide;

N-{5-[N'-(4-Chlorophenyl)-N'-methylhydrazinocarbonyl]-1H-thieno[2,3-c]pyrazol-3-yl}-3-morpholin-4-ylmethylbenzamide;

4-[(2-Diethylaminoethylamino)methyl]-N-[5-(N'-methyl-N'-phenylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-[(2-diethylaminoethylamino)methyl]benzamide;

4-[(Methylphenylamino)methyl]-N-[5-(N'-methyl-N'-phenylhydrazinocarbonyl)-1H-thieno[2,3-c]pyrazol-3-yl]benzamide;

4-[(Diisopropylamino)methyl]-N-[5-(N'-methyl-N'-phenylhydrazinocarbonyl)-1H-thieno[2,3-c]pyrazol-3-yl]benzamide trifluoroacetate;

N-[5-(N'-Benzylhydrazinocarbonyl)-1H-thieno[2,3-c]pyrazol-3-yl]-4-methoxybenzamide;

4-Methoxy-N-[5-(N'-pyrid-2-ylhydrazinocarbonyl)-1H-thieno[2,3-c]pyrazol-3-yl]benzamide;

N-{5-[N'-(4-Chlorophenyl)-N'-methylhydrazinocarbonyl]-1H-thieno[2,3-c]pyrazol-3-yl}-4-(4-methylpiperazin-1-yl)benzamide;

N-[5-(N'-Benzyl-N'-methylhydrazinocarbonyl)-1H-thieno[2,3-c]pyrazol-3-yl]-4-(4-methylpiperazin-1-yl)benzamide;

N-(Piperid-1-yl)-3-[4-(4-methylpiperazin-1-yl)benzoylamino]-1H-thieno[2,3-c]-pyrazole-5-carboxamide;

N-[5-(N'-Benzylhydrazinocarbonyl)-1H-thieno[2,3-c]pyrazol-3-yl]-4-(4-methylpiperazin-1-yl)benzamide;

N-[5-(N'-Ethyl-N'-phenylhydrazinocarbonyl)-1H-thieno[2,3-c]pyrazol-3-yl]-4-(4-methylpiperazin-1-yl)benzamide;

N-[5-(N'-Benzyl-N'-phenylhydrazinocarbonyl)-1H-thieno[2,3-c]pyrazol-3-yl]-4-(4-methylpiperazin-1-yl)benzamide;

N-[5-(N'-Methyl-N'-phenylhydrazinocarbonyl)-1H-thieno[2,3-c]pyrazol-3-yl]-4-(4-methylpiperazin-1-yl)benzamide;

N-{5-[N'-(4-Chlorophenyl)-N'-cyclobutylmethylhydrazinocarbonyl]-1H-thieno[2,3-c]pyrazol-3-yl}-4-(4-methylpiperazin-1-yl)benzamide;

N-{5-[N'-Ethyl-N'-(4-fluorophenyl)hydrazinocarbonyl]-1H-thieno[2,3-c]pyrazol-3-yl}-4-(4-methylpiperazin-1-yl)benzamide;

N-{5-[N'-(4-Fluorophenyl)-N'-(2-methoxyethyl)hydrazinocarbonyl]-1H-thieno[2,3-c]pyrazol-3-yl}-4-(4-methylpiperazin-1-yl)benzamide;

N-[5-(N'-Ethyl-N'-o-tolylhydrazinocarbonyl)-1H-thieno[2,3-c]pyrazol-3-yl]-4-(4-methylpiperazin-1-yl)benzamide;

N-[5-(N'-Ethyl-N'-m-tolylhydrazinocarbonyl)-1H-thieno[2,3-c]pyrazol-3-yl]-4-(4-methylpiperazin-1-yl)benzamide;

N-[5-(N'-Ethyl-N'-m-tolylhydrazinocarbonyl)-1H-thieno[2,3-c]pyrazol-3-yl]-4-(4-methylpiperazin-1-yl)benzamide;

N-{5-[N'-(4-Fluorophenyl)-N'-isobutylhydrazinocarbonyl]-1H-thieno[2,3-c]pyrazol-3-yl}-4-(4-methylpiperazin-1-yl)benzamide;

N-{5-[N'-(3-Bromophenyl)-N'-ethylhydrazinocarbonyl]-1H-thieno[2,3-c]pyrazol-3-yl}-4-(4-methylpiperazin-1-yl)benzamide;

6-(4-Methyl[1,4]diazepan-1-yl)-N-[5-(N'-methyl-N'-phenylhydrazinocarbonyl)-1H-thieno[2,3-c]pyrazol-3-yl]nicotinamide;

N-[5-(Benzylidenehydrazinocarbonyl)-1H-thieno[2,3-c]pyrazol-3-yl]-4-(4-methylpiperazin-1-yl)benzamide;

N-[5-(N'-Methyl-N'-phenylhydrazinocarbonyl)-1H-thieno[2,3-c]pyrazol-3-yl]-4-(2-morpholin-4-ylethoxy)benzamide; and 4-(4-Methyl[1,4]diazepan-1-yl)-N-[5-(N'-methyl-N'-phenylhydrazinocarbonyl)-1H-thieno[2,3-c]pyrazol-3-yl]benzamide;

or a pharmaceutically acceptable salt thereof.

* * * * *

UNITED STATES PATENT AND TRADEMARK OFFICE
CERTIFICATE OF CORRECTION

PATENT NO.       : 7,595,320 B2
APPLICATION NO.  : 11/846669
DATED            : September 29, 2009
INVENTOR(S)      : Claude Barberis et al.

It is certified that error appears in the above-identified patent and that said Letters Patent is hereby corrected as shown below:

In column 3, line 10, delete "–(CO–C$_6$)" and insert -- –(C$_0$–C$_6$) --, therefor.

In column 3, line 25-34, delete "  " and insert -- --, therefor.

In column 28, line 11-25, delete " 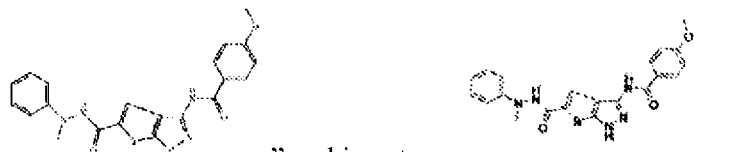 " and insert -- --, therefor.

In column 28, line 45-60, delete " 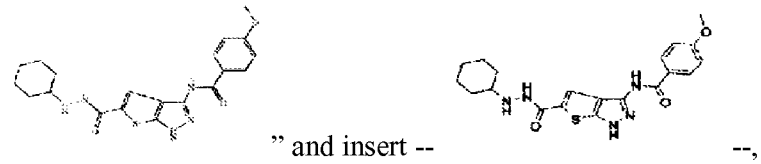 " and insert -- --, therefor.

In column 29, line 11-27, delete "  " and insert -- --, therefor.

Signed and Sealed this
Fifteenth Day of May, 2012

David J. Kappos
*Director of the United States Patent and Trademark Office*

CERTIFICATE OF CORRECTION (continued)
U.S. Pat. No. 7,595,320 B2

In column 29, line 48-63, delete " 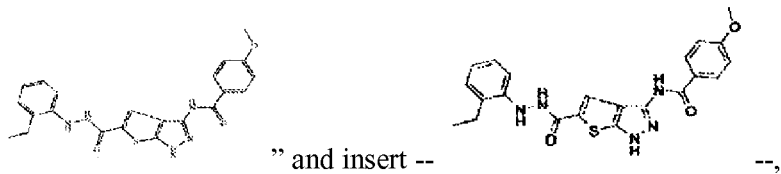 " and insert -- --, therefor.

In column 30, line 16-32, delete " 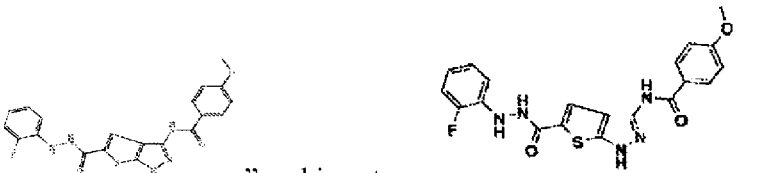 " and insert -- --, therefor.

In column 30, line 51-65, delete " 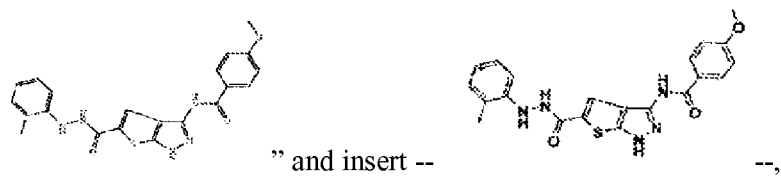 " and insert -- --, therefor.